United States Patent
Jackson et al.

(10) Patent No.: US 11,103,526 B2
(45) Date of Patent: Aug. 31, 2021

(54) METHODS FOR TREATMENT USING SMALL MOLECULE POTASSIUM-SPARING DIURETICS AND NATRIURETICS

(71) Applicant: University of Pittsburgh—Of the Commonwealth System of Higher Education, Pittsburgh, PA (US)

(72) Inventors: Edwin K. Jackson, Pittsburgh, PA (US); Stevan P. Tofovic, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/909,927

(22) Filed: Jun. 23, 2020

(65) Prior Publication Data

US 2020/0323892 A1 Oct. 15, 2020

Related U.S. Application Data

(63) Continuation of application No. 16/329,126, filed as application No. PCT/US2017/049402 on Aug. 30, 2017, now Pat. No. 10,729,711.

(60) Provisional application No. 62/381,514, filed on Aug. 30, 2016.

(51) Int. Cl.
| | |
|---|---|
| A61K 31/708 | (2006.01) |
| A61K 31/522 | (2006.01) |
| A61P 7/00 | (2006.01) |
| A61P 3/10 | (2006.01) |
| A61P 11/00 | (2006.01) |
| A61P 7/02 | (2006.01) |
| A61K 45/06 | (2006.01) |
| A61P 25/28 | (2006.01) |
| A61K 31/4965 | (2006.01) |
| A61P 31/18 | (2006.01) |
| A61P 9/12 | (2006.01) |
| A61P 9/04 | (2006.01) |
| A61P 13/00 | (2006.01) |

(52) U.S. Cl.
CPC ........ *A61K 31/708* (2013.01); *A61K 31/4965* (2013.01); *A61K 31/522* (2013.01); *A61K 45/06* (2013.01); *A61P 3/10* (2018.01); *A61P 7/00* (2018.01); *A61P 7/02* (2018.01); *A61P 9/04* (2018.01); *A61P 9/12* (2018.01); *A61P 11/00* (2018.01); *A61P 13/00* (2018.01); *A61P 25/28* (2018.01); *A61P 31/18* (2018.01)

(58) Field of Classification Search
None
See application file for complete search history.

(56) References Cited

U.S. PATENT DOCUMENTS

2012/0134979 A1* 5/2012 Xia .................. A61K 31/52
424/94.6

FOREIGN PATENT DOCUMENTS

| EP | 0374096 B1 | 6/1990 |
|---|---|---|
| WO | WO 2009/152453 | 12/2009 |
| WO | WO 2010/011860 | 1/2010 |

OTHER PUBLICATIONS

Tuttle, The Journal of Biological Chemistry, vol. 269, No. 7, 1984, Apr. 10, pp. 4065-4069. (Year: 1984).*
Claster, Risk of altitude exposure in sickle cell disease. West J. Med 135:364-367, Nov. 1981. (Year: 1981).*
DeBellis et al., "Inhibition of sickling in vitro by three purine-based antiviral agents: An approach to the treatment of sickle cell disease." *Blood Cells, Molecules, and Diseases* 31(2): 286-290 (2003).
International Search Report and Written Opinion for App. No. PCT/US2017/049402, dated Dec. 28, 2017, by the Israel Patent Office acting as ISA (14 pages).
Jackson et al., "Guanosine regulates adenosine levels in the kidney." *Physiological Reports* 2(5): e12028 (9 pages) (2014).
Kavianipour et al., "8'-Aminoguanosine inclusion results in enhanced efflux of taurine in preconditioned ischemic myocardium." *Journal of Cardiovascular Pharmacology* 41(2): 240-248 (2003).
Krenitsky et al., "Nucleotide analogue inhibitors of purine nucleoside phosphorylase." *Journal of Biological Chemistry* 265(6): 3066-3069 (1990).
Morris and Montgomery, "Inhibitors of the enzyme purine nucleoside phosphorylase." *Expert Opinion on Therapeutic Patents* 8(3): 283-299 (1998).
Osborne et al., "A canine model of induced purine nucleoside phosphoryase deficiency," *Clin. Exp. Immunol.* 66: 166-172 (1986).
Zamzow et al., "Adenosine produced by neurons is metabolized to hypoxanthine by astrocytes," *Journal of Neuroscience Research* 86(15): 3447-3455 (2008).

* cited by examiner

*Primary Examiner* — Layla D Berry
(74) *Attorney, Agent, or Firm* — Klarquist Sparkman, LLP

(57) ABSTRACT

PNPase inhibitors (such as 8-substituted guanine and/or 8-substituted guanosine) and/or PNPase purine nucleoside substrates (such as guanosine and/or inosine) can also be used in methods of treating SCD or reducing sickling of red blood cells (RBCs). Herein, 8-substituted guanine and/or 8-substituted guanosine compounds are used in methods to treat hypertension (such as systemic or pulmonary hypertension), stroke, diabetes, and/or patients in need of a diuretic. In addition, 8-substituted guanine and/or 8-substituted guanosine compounds are included in a beverage composition. Further, purine nucleoside phosphorylase (PNPase) inhibitors (such as 8-substituted guanine and/or 8-substituted guanosine) and/or PNPase purine nucleoside substrates (such as guanosine and/or inosine) can be used in methods of treating or reducing the risk of pulmonary hypertension (PH), such as PH associated with HIV or sickle cell disease (SCD).

23 Claims, 50 Drawing Sheets

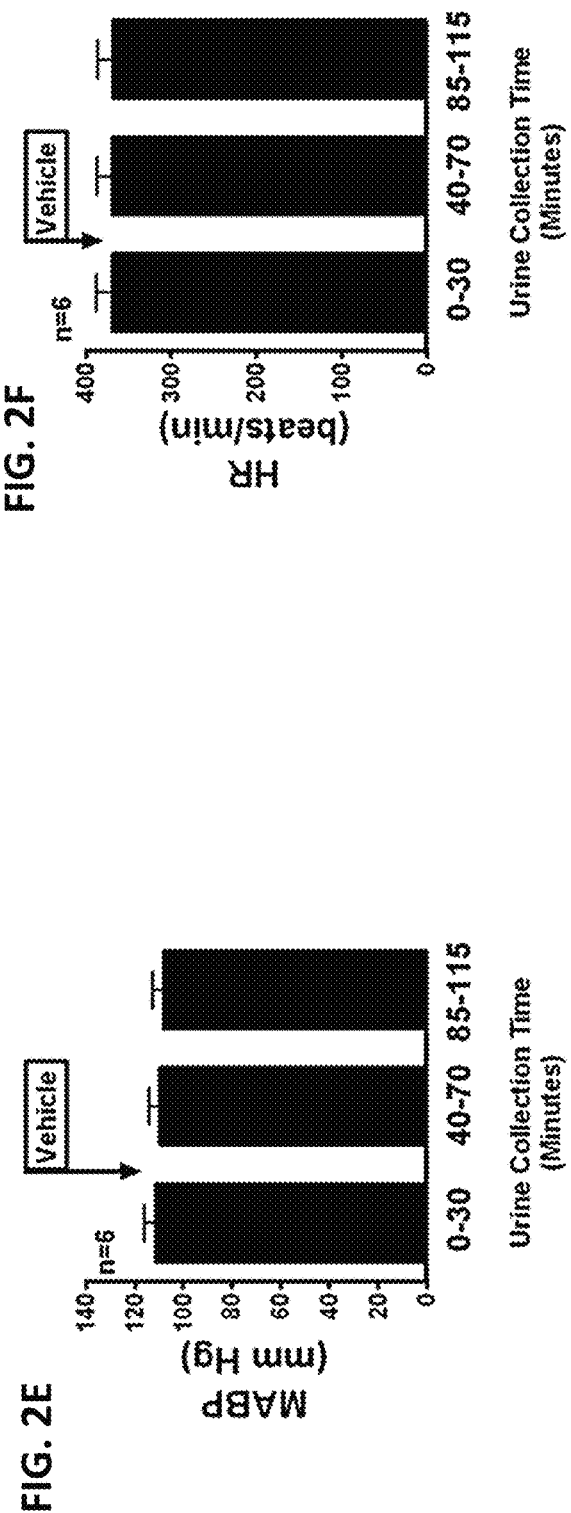
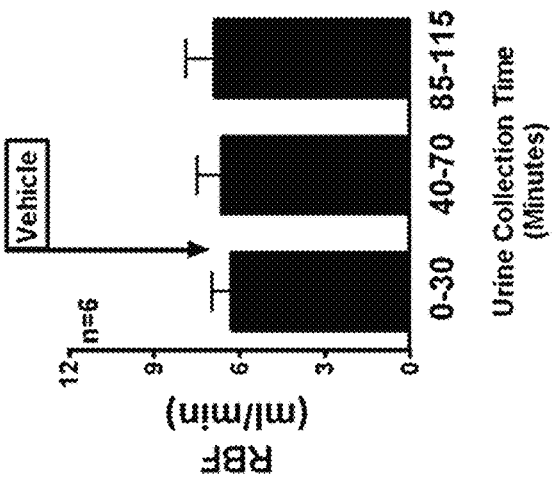
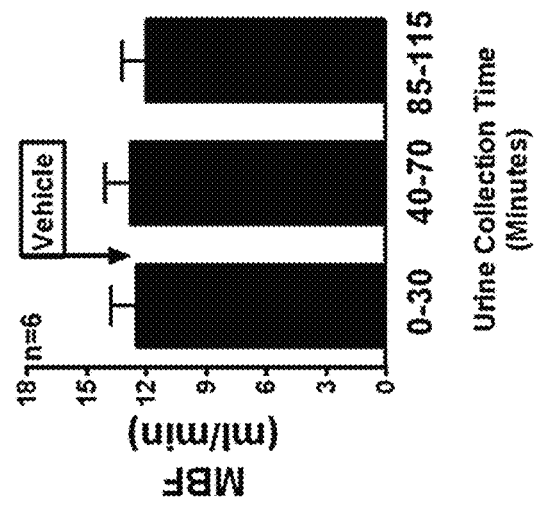

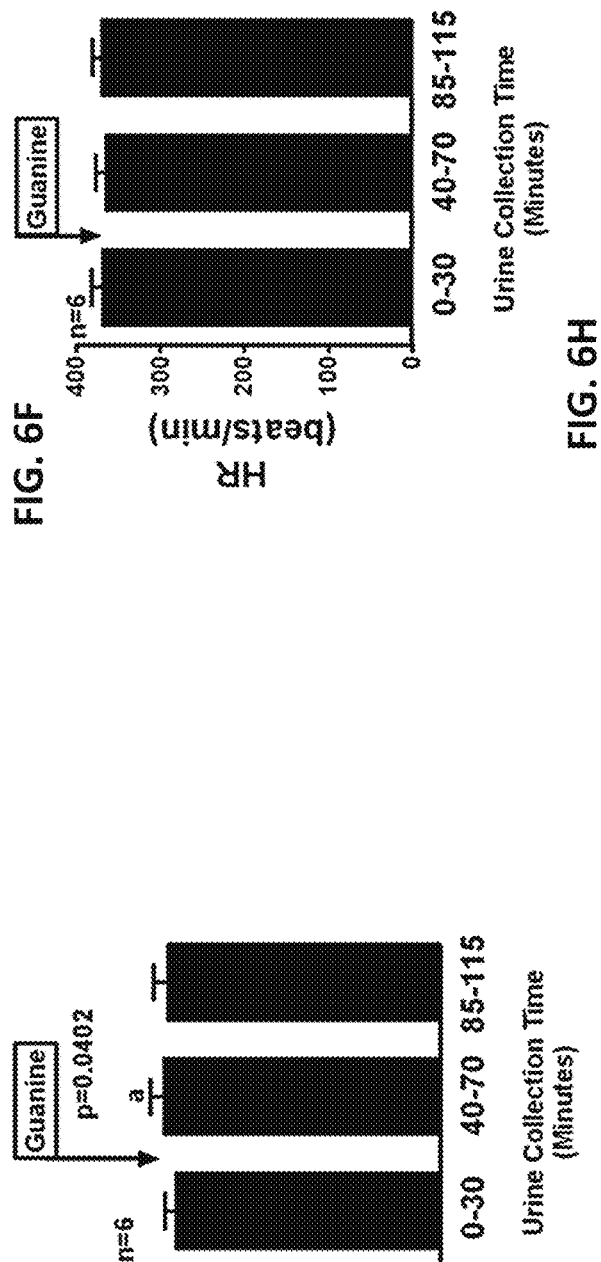
FIG. 6E
FIG. 6F
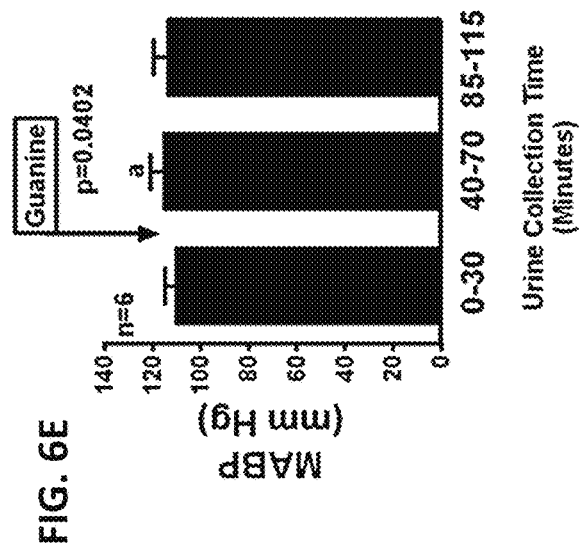
FIG. 6G
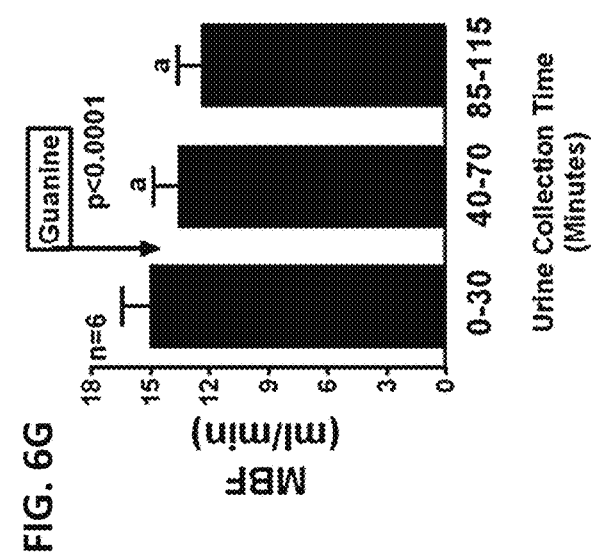

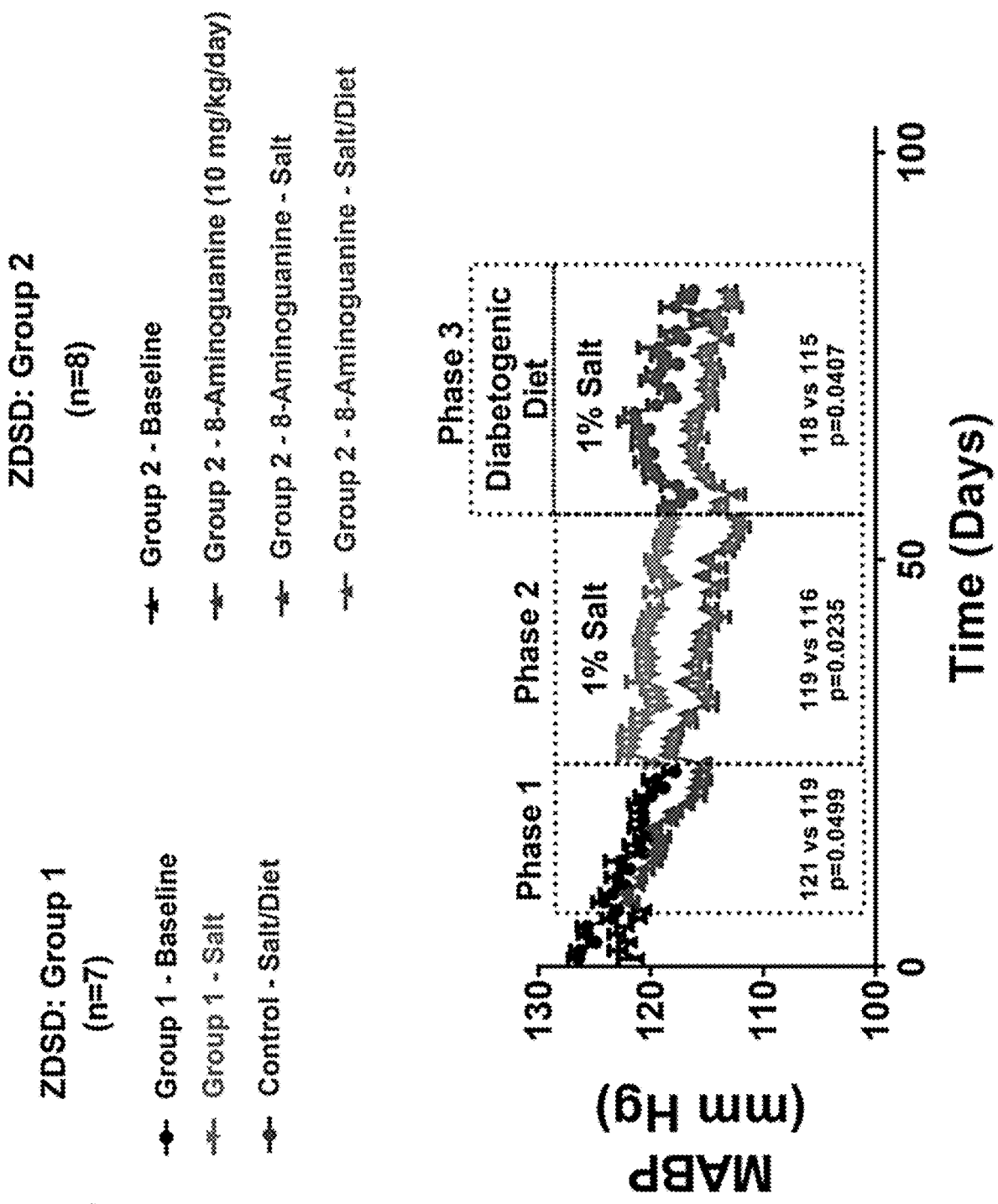

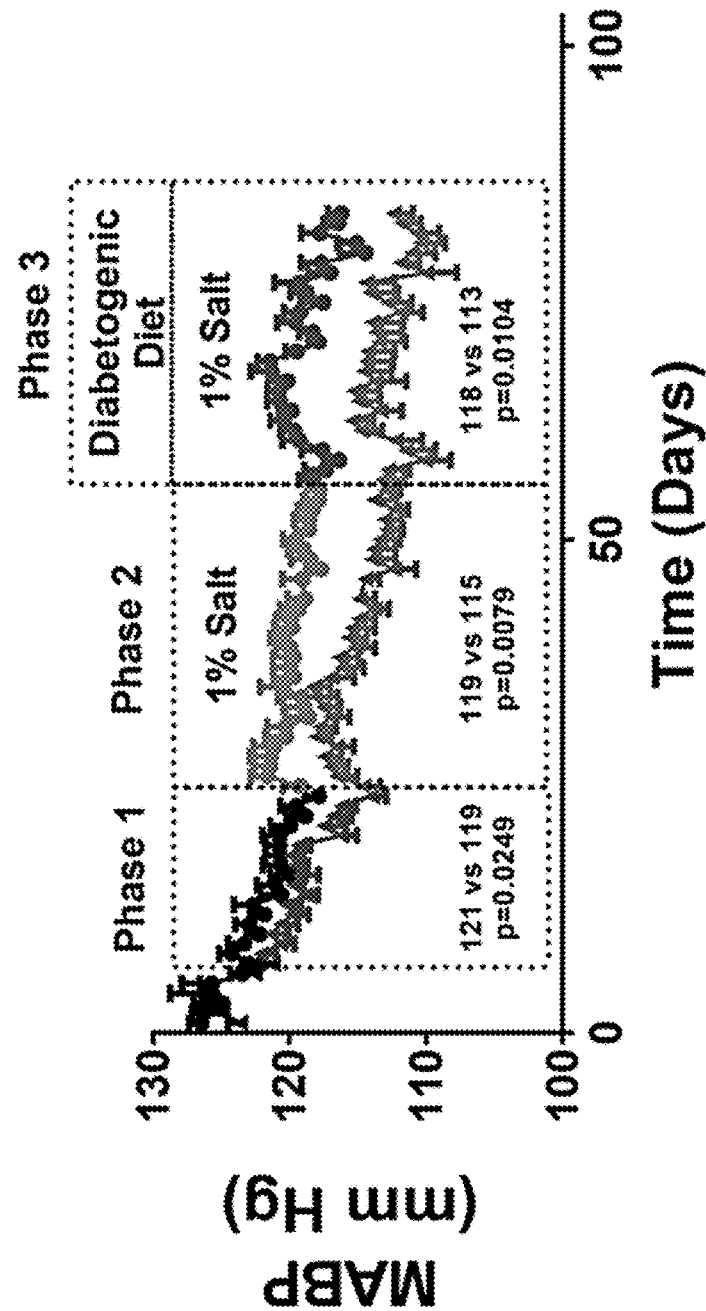

FIG. 16

High-salt (8%) diet with no treatment (evidence of large strokes)

low-salt (0.3%) diet with no treatment (brain is normal)

High-salt (8%) diet with 8-aminoguanosine (brain is normal)

High-salt (8%) diet with 8-aminoguanine (brain is normal)

MRI T2-weighted images in live Dahl SS rats
FOV 25.6mm×25.6mm; Matrix 256×256; slice thickness: 0.5mm.
White area indicates large cortical stroke
White area indicates large subcortical stroke

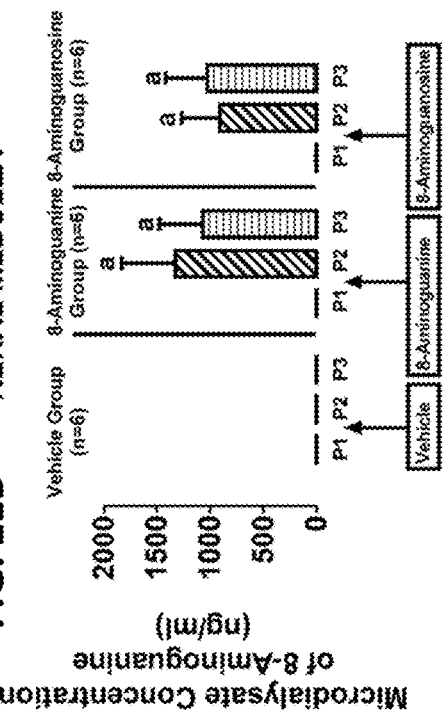
FIG. 21B RENAL MEDULLA
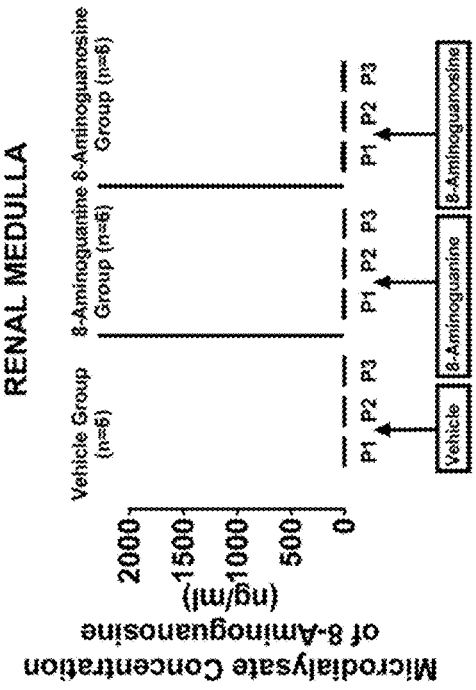
FIG. 21D RENAL MEDULLA
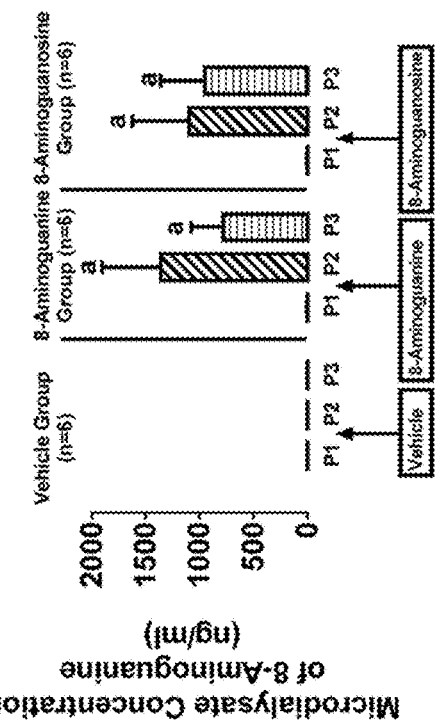
FIG. 21A RENAL CORTEX
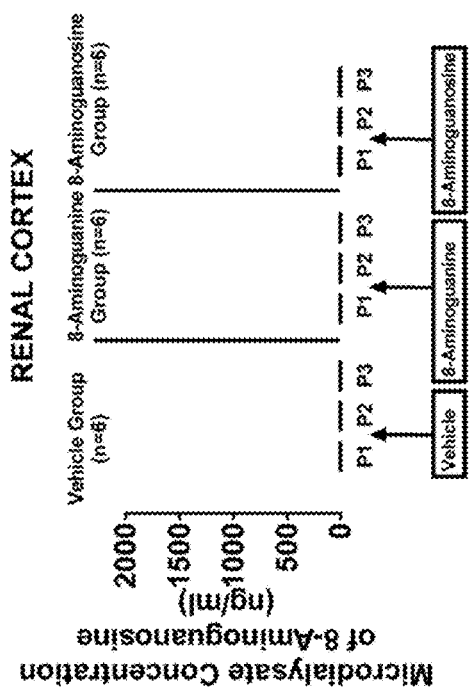
FIG. 21C RENAL CORTEX

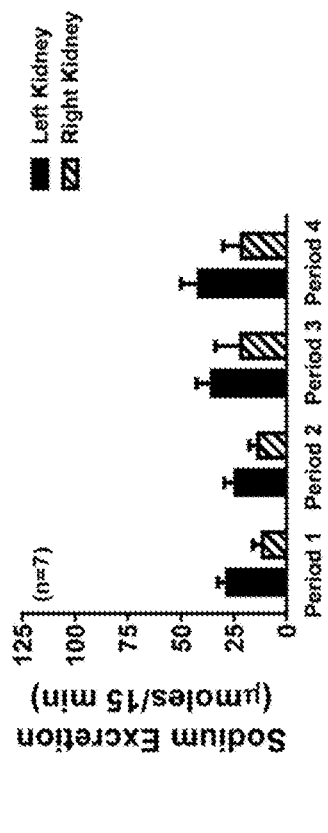
FIG. 24A  Effects of Time/Vehicle on Urine Volume
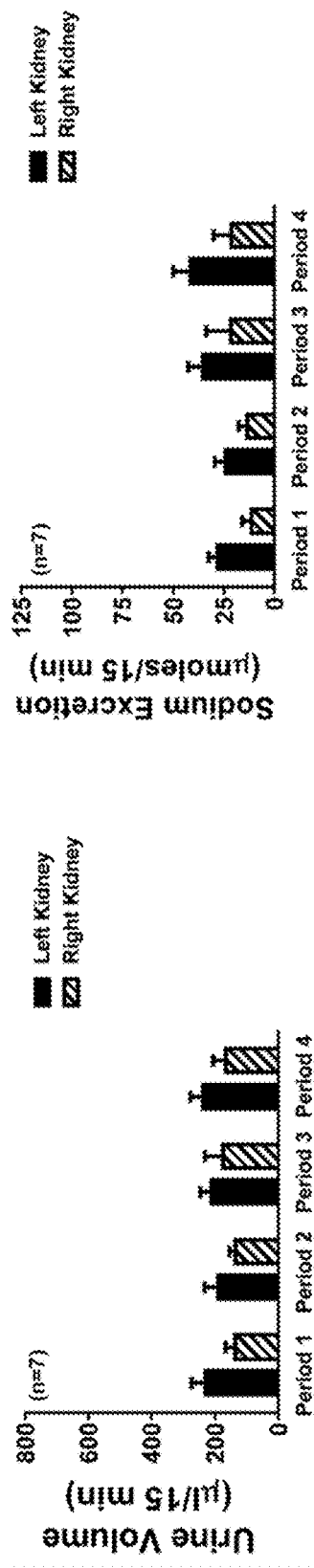
FIG. 24B  Effects of Time/Vehicle on Sodium Excretion
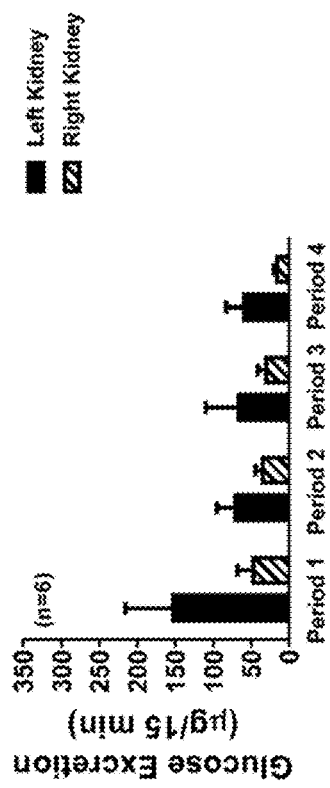
FIG. 24D  Effects of Time/Vehicle on Glucose Excretion
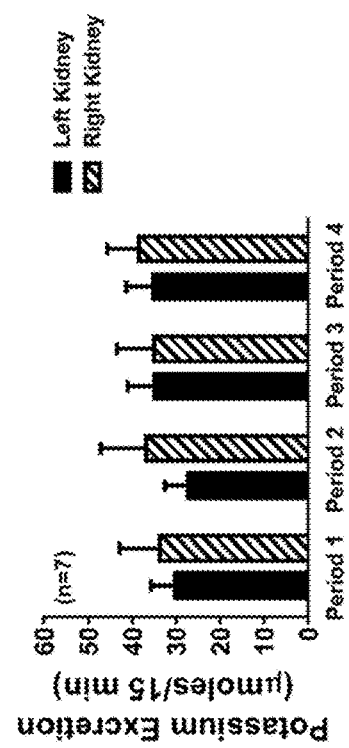
FIG. 24C  Effects of Time/Vehicle on Potassium Excretion

FIG. 25A
FIG. 25B
FIG. 25C
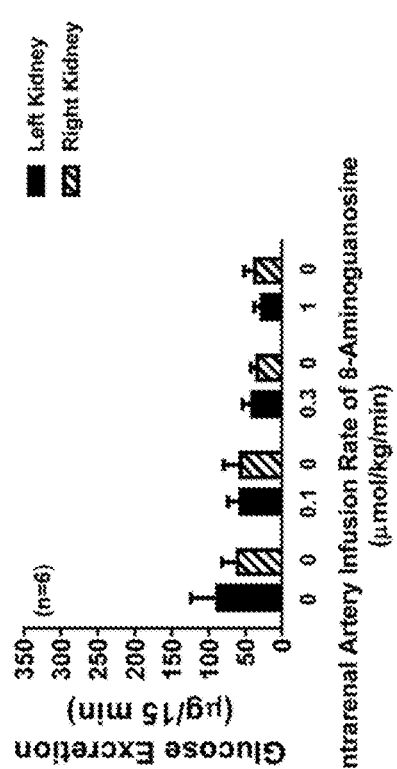
FIG. 25D
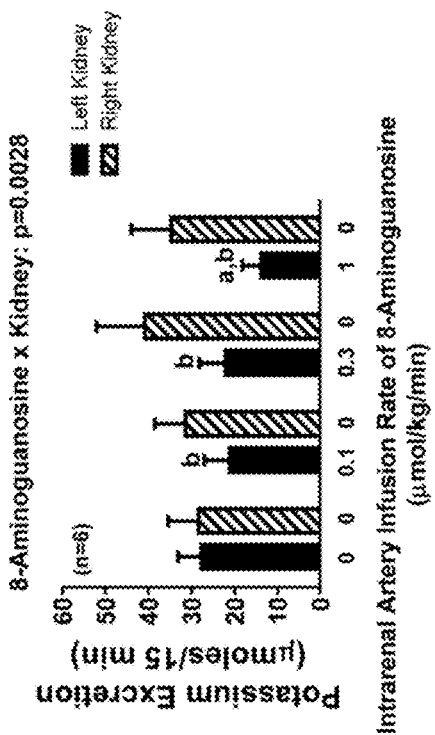

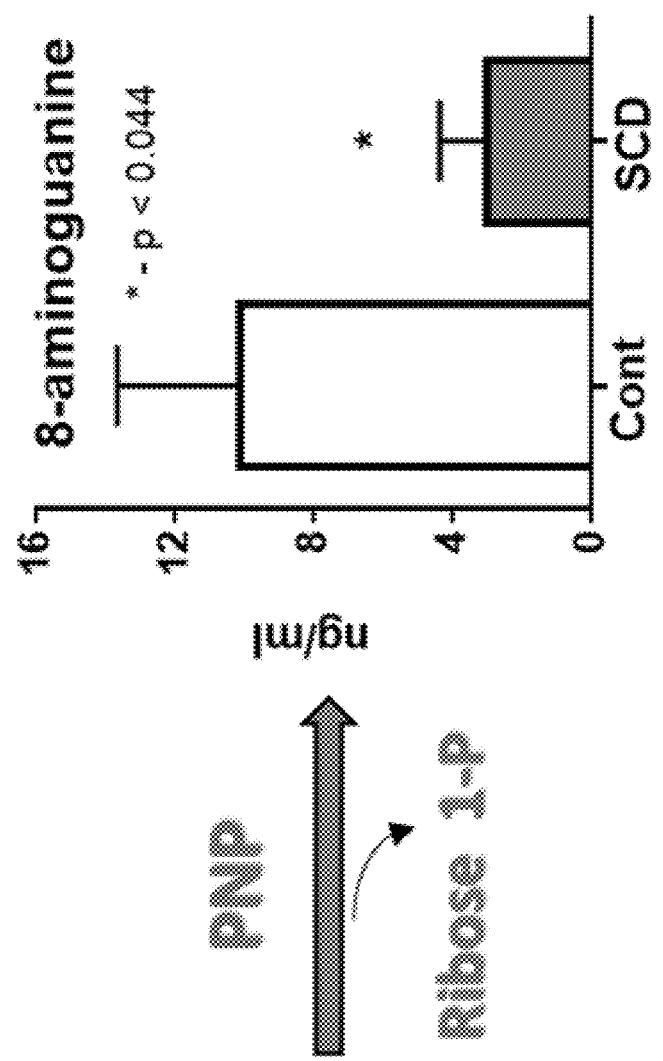
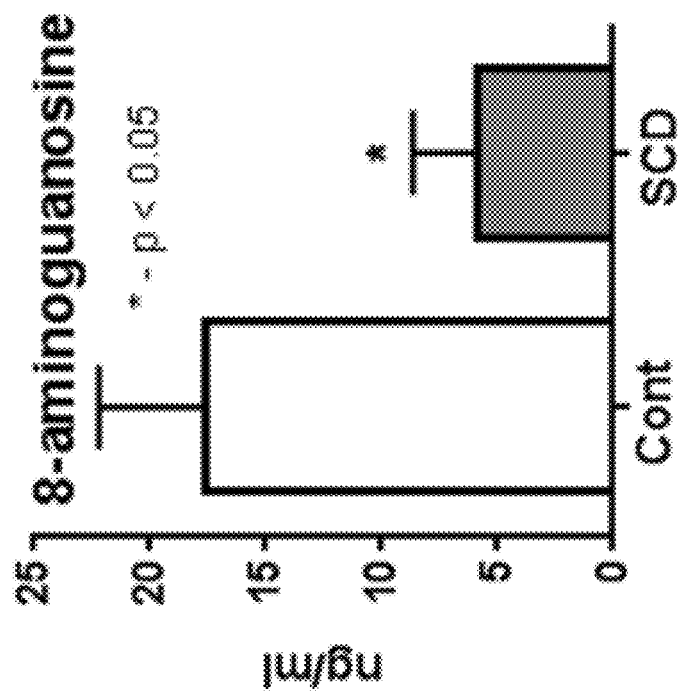
FIG. 28A
FIG. 28B

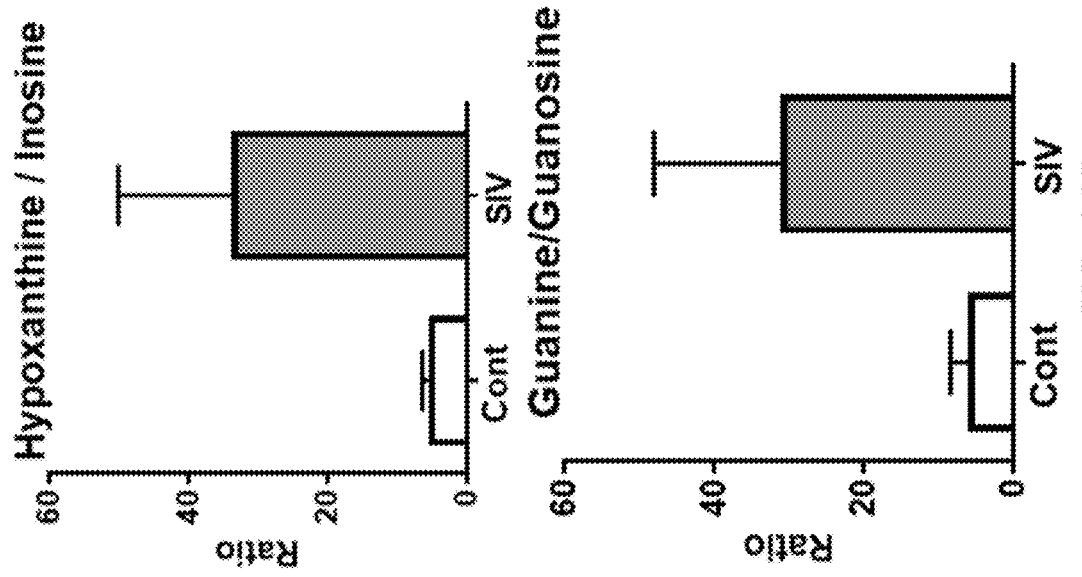

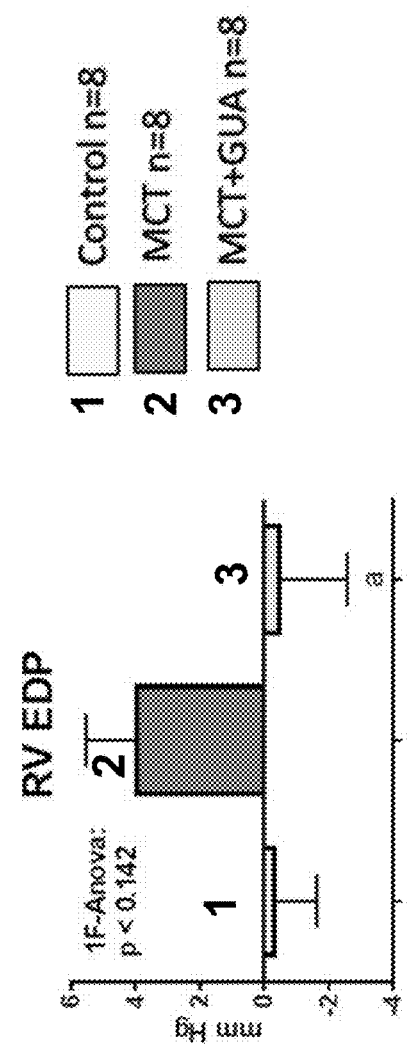
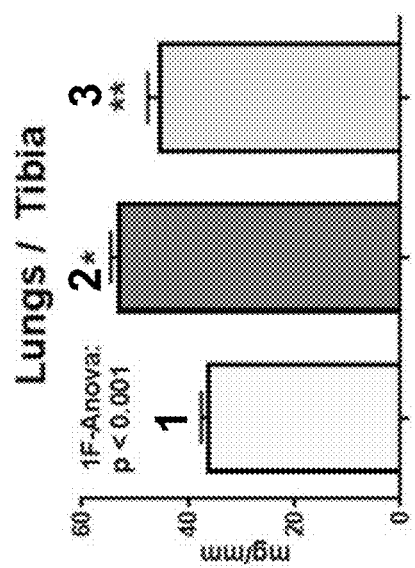
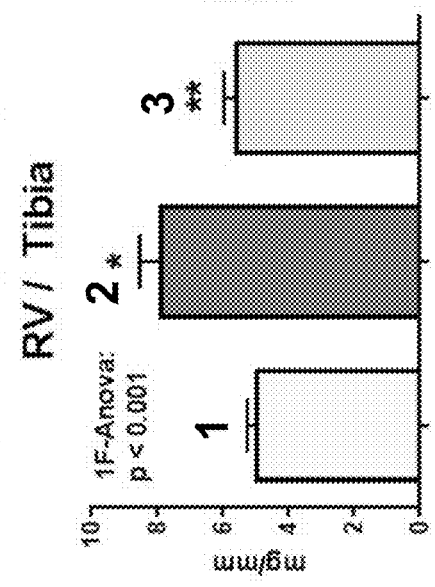
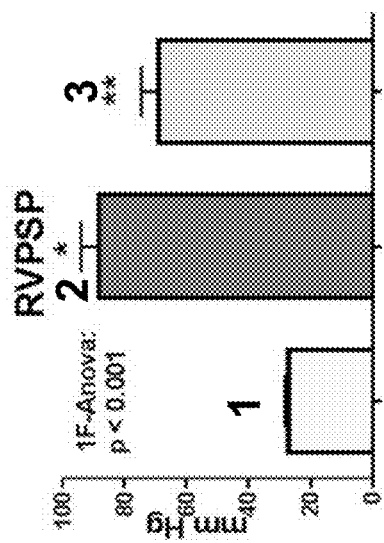
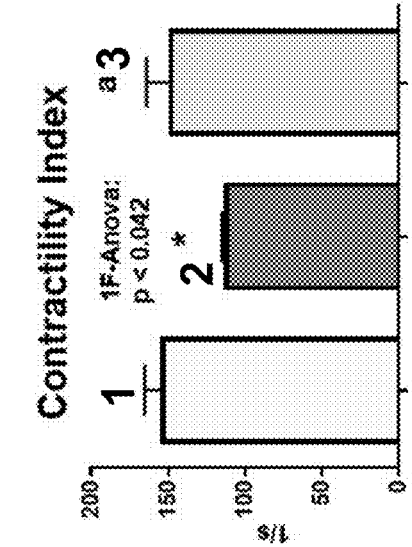
FIG. 31A
FIG. 31B
FIG. 31C
FIG. 31D
FIG. 31E

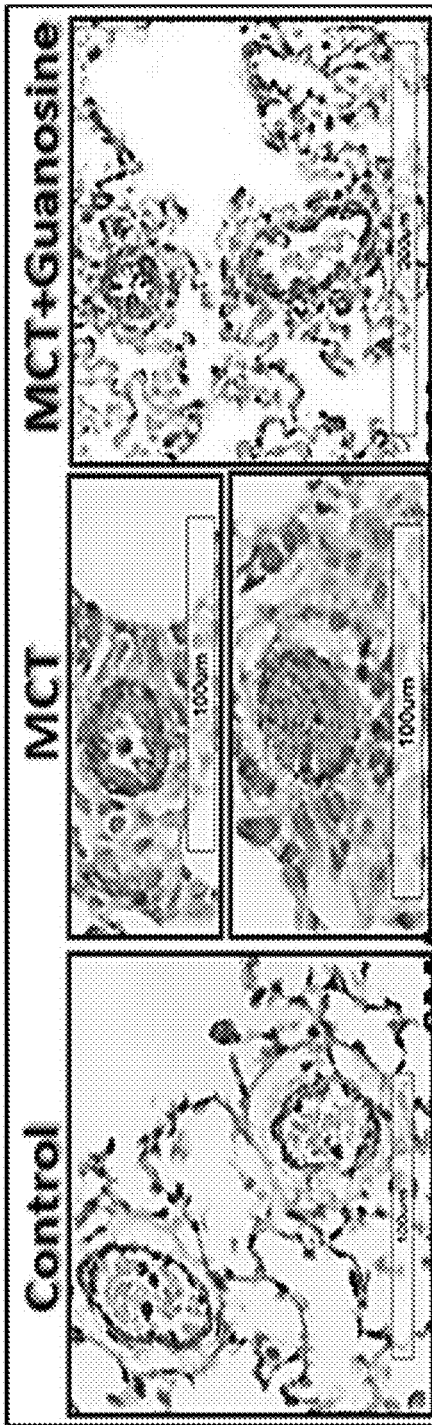
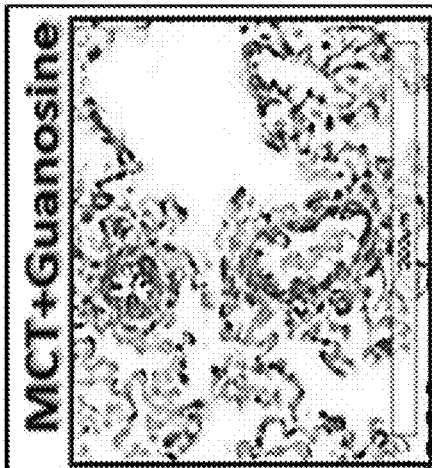
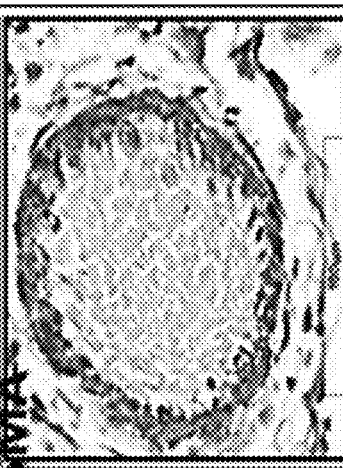
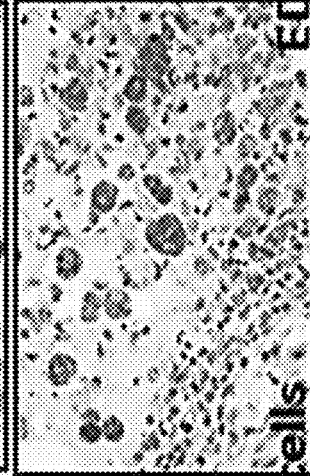
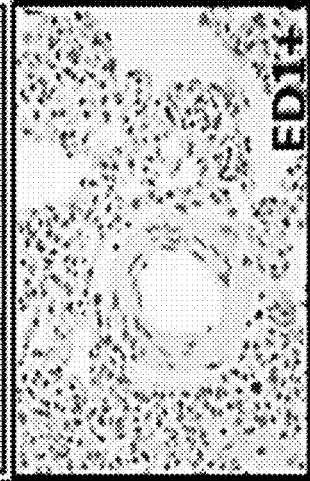
FIG. 32A Control  FIG. 32B MCT  FIG. 32C MCT+Guanosine
FIG. 32D  FIG. 32E  FIG. 32F α-SMA
FIG. 32G  FIG. 32H  FIG. 32I ED1+ cells

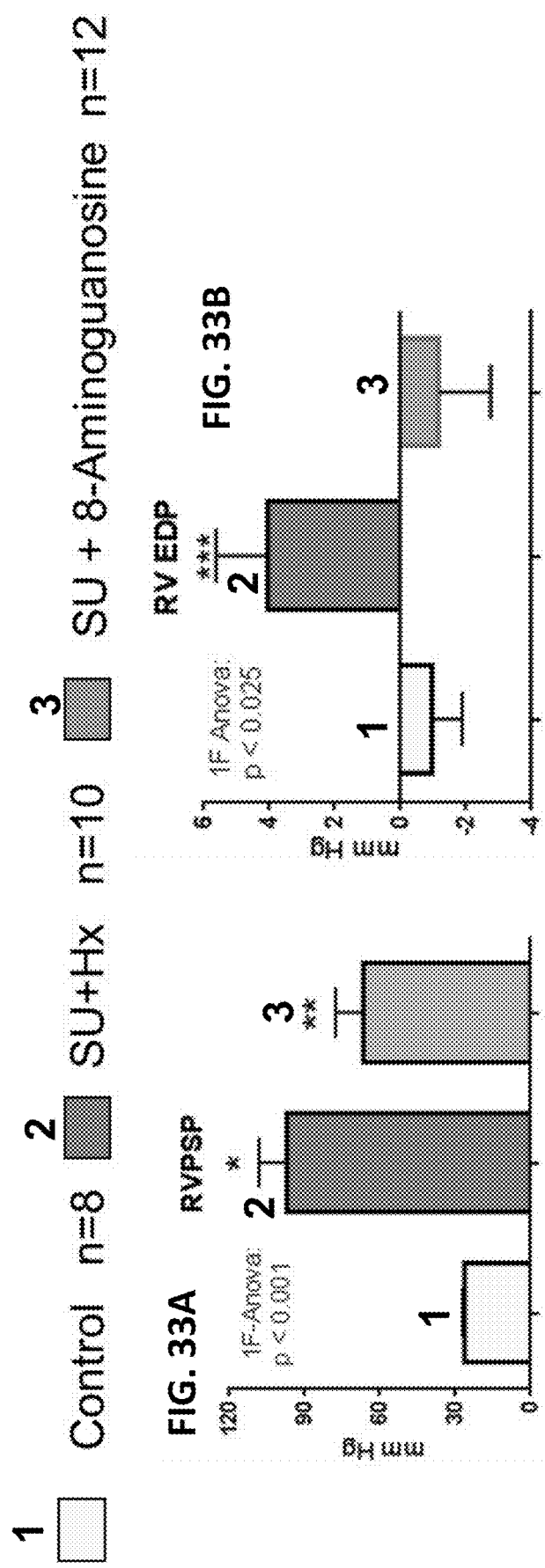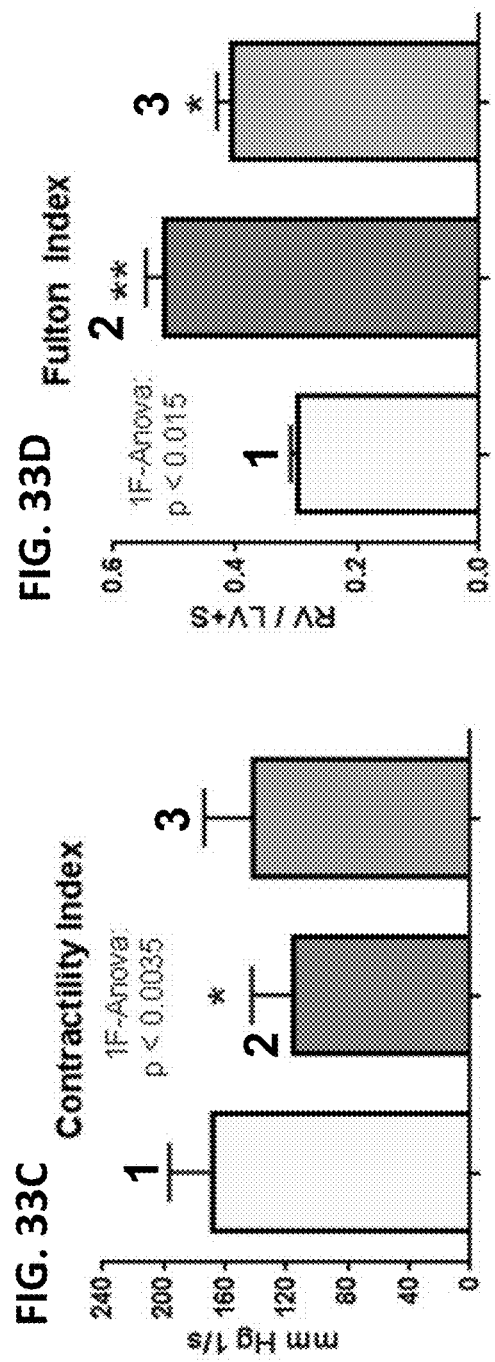
FIG. 33A  FIG. 33B  FIG. 33C  FIG. 33D

FIG. 34A  FIG. 34B
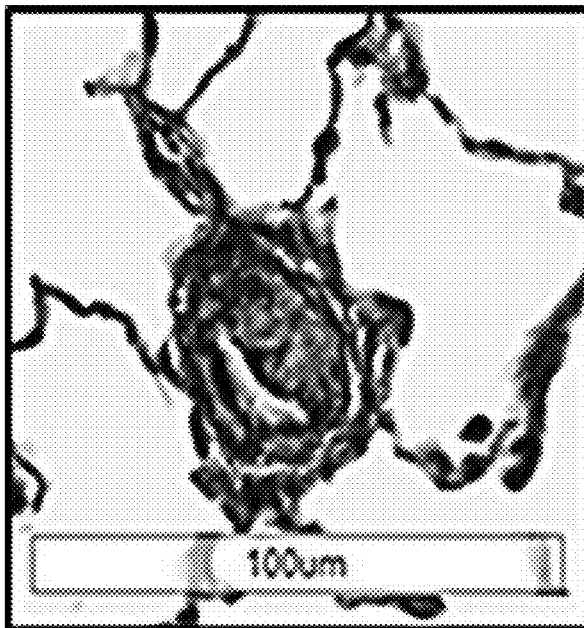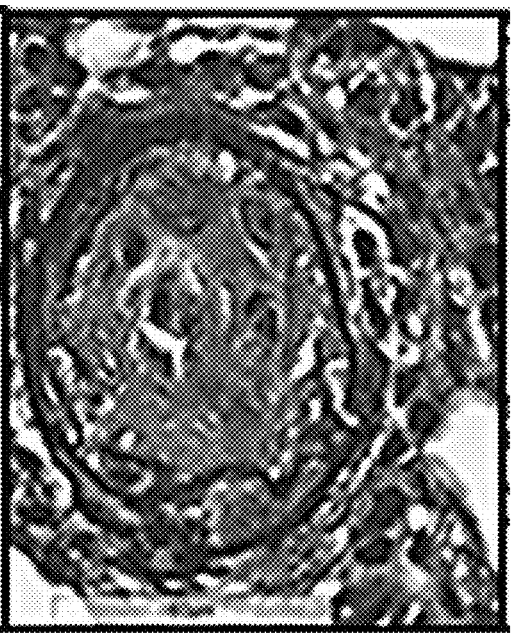
FIG. 34C  FIG. 34D
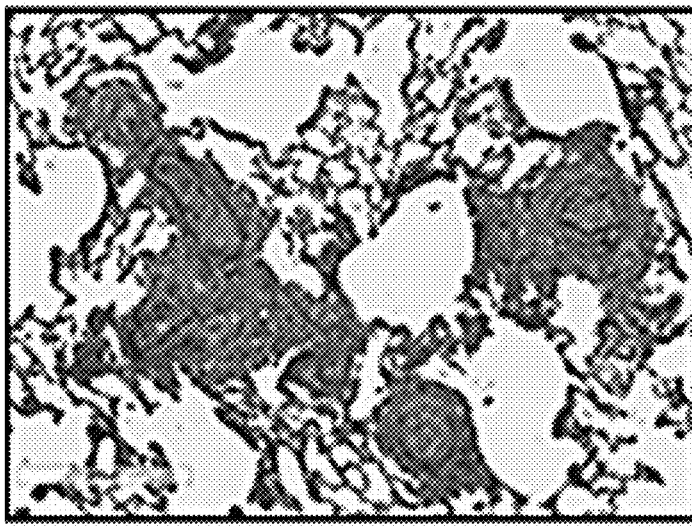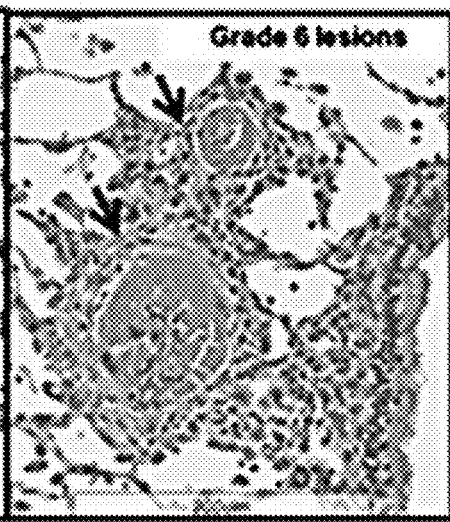

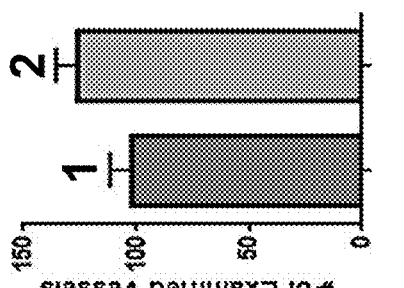
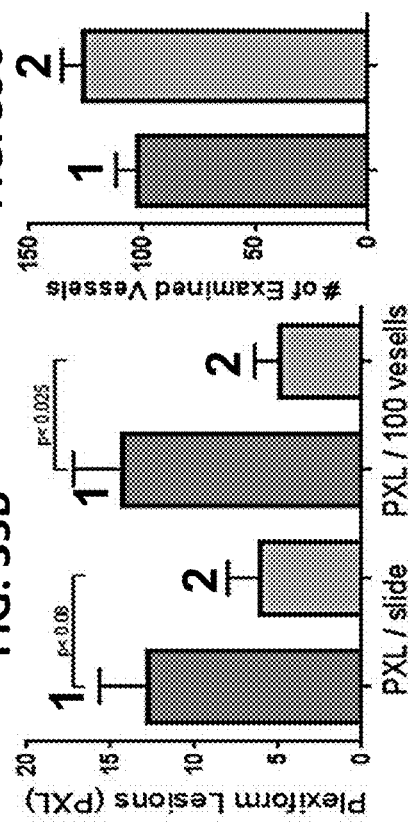
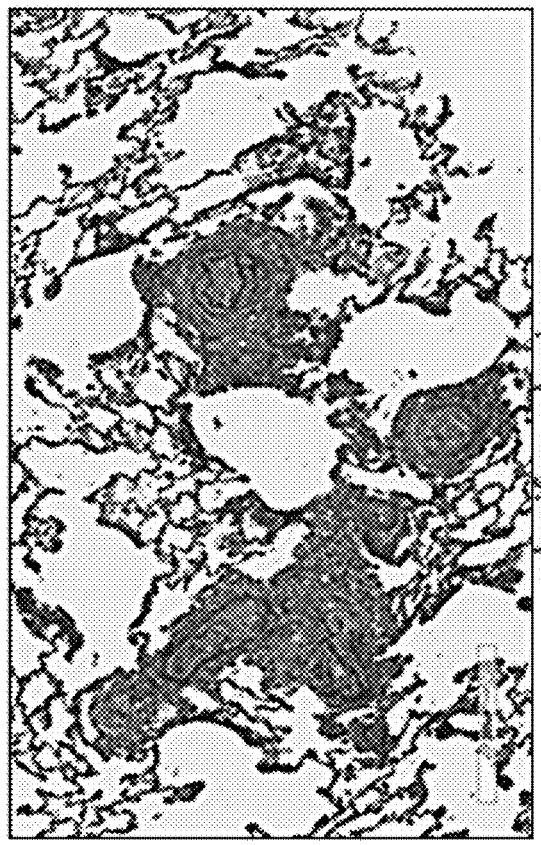
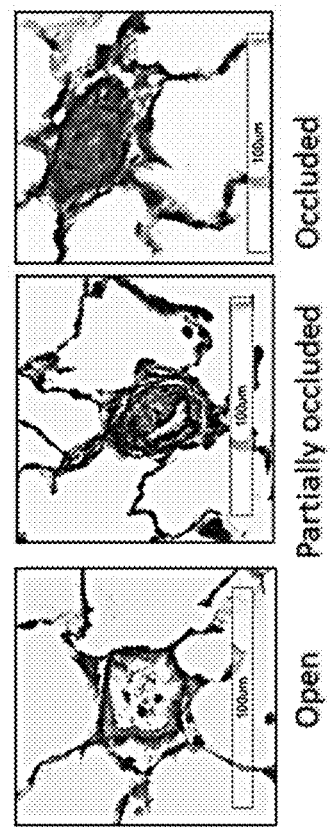
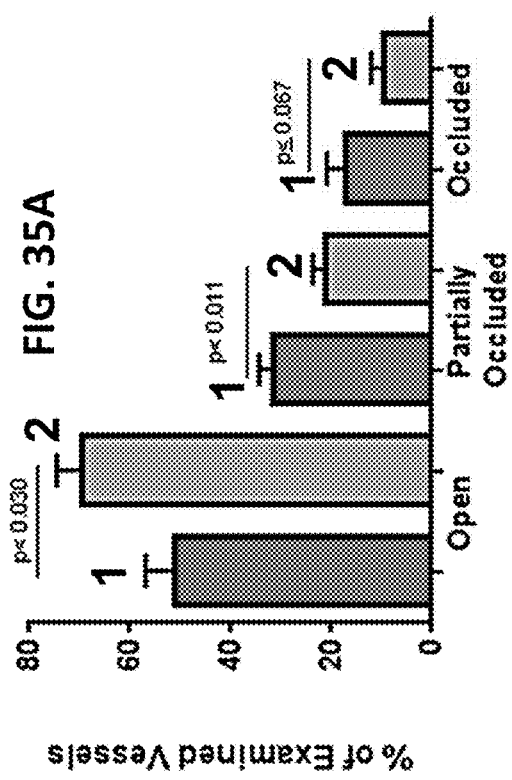

METHODS FOR TREATMENT USING SMALL MOLECULE POTASSIUM-SPARING DIURETICS AND NATRIURETICS

CROSS REFERENCE TO RELATED APPLICATIONS

This application is a continuation of U.S. patent application Ser. No. 16/329,126, filed Feb. 27, 2019, which is the U.S. National Stage of International Application No. PCT/US2017/049402, filed Aug. 30, 2017, which was published in English under PCT Article 21(2), and claims the benefit of U.S. Provisional Application No. 62/381,514, filed Aug. 30, 2016. The prior applications are incorporated by reference herein in their entirety.

ACKNOWLEDGMENT OF GOVERNMENT SUPPORT

This invention was made with government support under HL109002 awarded by the National Institutes of Health. The government has certain rights in the invention.

FIELD

This relates to the field of small molecule PNPase substrates and inhibitors as well as potassium-sparing diuretics and natriuretics and methods of their use.

BACKGROUND

With the notable exceptions of mineralocorticoid antagonists and epithelial sodium channel (ENaC) inhibitors, most clinically useful diuretics/natriuretics (for example, thiazide-type, thiazide-like, and loop diuretics) increase potassium excretion, leading to increased risk of hypokalemia (Reilly R F et al., Goodman & Gilman's the pharmacological basis of therapeutics, 671-719, 2011). In addition, the tendency of thiazide-like/type diuretics to increase plasma glucose has been widely discussed and remains a concern (Palmer B F et al., Seminars in Nephrology, 31:542-552, 2011; Gilbertsen R B et al., Annals of the New York Academy of Sciences, 451:313-314, 1985). As diabetics frequently also suffer from hypertension, such patients would benefit from diuretics that do not increase glucose levels (Sowers J R et al., Hypertension, 37:1053-1059, 2001). Thus, a need exists for a diuretic/natriuretic that does not lead to increased potassium excretion and/or an increase in plasma glucose.

Peroxynitrite ($ONOO^-$) is formed in vivo from the diffusion-controlled reaction between superoxide anion ($O2^{--}$) and nitric oxide (NO) (Carballal S et al., Biochimica et Biophysica Acta, 1840:768-780, 2014). Further, $ONOO^-$ is a highly reactive nitrogen species (RNS) that can mediate nitration (i.e., insertion of $-NO_2$) of a number of endogenous compounds, including those containing a guanine moiety (Ohshima H et al., Antioxidants & Redox Signaling, 8:1033-1045, 2006; Szabo C et al., Nitric Oxide, 1:373-385, 1997; Yermilov V et al., FEBS Lett, 376:207-210, 1995). In this regard, $ONOO^-$ nitrates guanine moieties at position 8 of the purine ring to produce 8-nitroguanine units in DNA, RNA, and the guanine nucleotide pool (Ohshima H et al., Antioxidants & Redox Signaling, 8:1033-1045, 2006; Szabo C et al., Nitric Oxide, 1:373-385, 1997; Yermilov V et al., FEBS Lett, 376:207-210, 1995). It is also conceivable that free guanine per se could be subjected to nitration at the 8 position. In addition to RNS-mediated modification of guanine-containing compounds, reactive oxygen species (ROS), such as $O_2^{--}$, can also modify position 8 of guanine moieties by inserting a hydroxyl functional group (Szabo C et al., Nitric Oxide, 1:373-385, 1997; Misiaszek R et al., Journal of Biological Chemistry, 279:32106-32115, 2004).

After modification of guanine moieties by RNS or ROS, subsequent catabolism of RNA, DNA, and the guanine nucleotide pool will release 8-nitroguanosine, 8-nitro-2-deoxyguanosine, 8-hydroxyguanosine, and 8-hydroxy-2-deoxyguanosine. Theoretically, reduction of 8-nitro groups could yield 8-aminoguanosine and 8-amino-2-deoxyguanosine, and purine nucleoside phosphorylase (PNPase) can convert such compounds into 8-aminoguanine (Osborne W R et al., Immunology, 59:63-67, 1986). In addition, PNPase might convert 8-nitroguanosine and 8-nitro-2-deoxyguanosine into 8-nitroguanine, and reduction of 8-nitroguanine would yield 8-aminoguanine. Similarly, PNPase might produce 8-hydroxyguanine from 8-hydroxyguanosine or 8-hydroxy-2-deoxyguanosine. Taken together, these considerations suggest the metabolic framework summarized in FIG. 1. Consistent with this framework are studies confirming the presence of 8-nitroguanosine, 8-aminoguanosine, 8-aminoguanine, 8-hydroxyguanosine, 8-nitroguanine, 8-hydroxyguanine, and 8-hydroxy-2-deoxyguanosine in tissues or urine (Akaike T et al., Proc Natl Acad Sci USA, 100:685-690, 2003; Sodum R S et al., Chem Res Toxicol, 6:269-276, 1993; Park E M et al., Proc Natl Acad Sci USA, 89:3375-3379, 1992; Ohshima H et al., Antioxid Redox Signal, 8:1033-1045, 2006; Fraga C G et al., Proc Natl Acad Sci USA, 87:4533-4537, 1990; Lam P M et al., Free Radic Biol Med, 52:2057-2063, 2012).

SUMMARY

Methods are disclosed for promoting natriuresis in a subject. In some examples, the methods include administering to the subject a therapeutically effective amount of a composition including guanine with a substituent at the 8-position and/or a guanosine comprising a substituent at the 8-position, wherein the 8-substituted guanine and/or 8-substituted guanosine promotes sodium excretion and maintains or suppresses potassium excretion, thereby promoting natriuresis in the subject.

In additional embodiments, methods are disclosed for lowering arterial pressure in a subject. The methods include administering to the subject a therapeutically effective amount of a composition including guanine with a substituent at the 8-position and/or a guanosine comprising a substituent at the 8-position, wherein the 8-substituted guanine and/or 8-substituted guanosine promotes sodium excretion and maintains or suppresses potassium excretion, thereby lowering arterial pressure in the subject.

In further embodiments, methods are disclosed for treating a subject with type 2 diabetes. The methods include administering to the subject a therapeutically effective amount of a composition including guanine with a substituent at the 8-position and/or a guanosine comprising a substituent at the 8-position, wherein the 8-substituted guanine and/or 8-substituted guanosine promotes sodium excretion and maintains or suppresses potassium excretion, thereby treating type 2 diabetes in the subject.

In yet other embodiments, methods are disclosed for reducing the likelihood of stroke and/or reducing stroke mortality in a subject. The methods include administering to the subject a therapeutically effective amount of a composition including guanine with a substituent at the 8-position and/or a guanosine comprising a substituent at the 8-position, wherein the 8-substituted guanine and/or 8-substituted guanosine promotes sodium excretion and maintains or suppresses potassium excretion, thereby reducing the likelihood of stroke and/or reducing stroke mortality in the subject.

In some embodiments, in any of the above methods, the substituent is amine, hydroxyl, nitro, nitroso, alkoxy, carbonyl, halogen, carboxyl, ester, carbonate, amide, or haloaliphatic. In specific non-limiting examples of all of these methods, the subject is administered a therapeutically effective amount of 8-aminoguanine and/or 8-aminoguanosine.

A fermented beverage is also disclosed that includes exogenous 8-aminoguanine and/or 8-aminoguanosine such that the total amount of the 8-aminoguanine and/or 8-aminoguanosine in the fermented beverage is greater than 500 ng/ml.

Methods are further disclosed for treating a subject with pulmonary hypertension (PH) or reducing the risk of PH in a subject, such as a human or mammalian subject. In some examples, the methods include administering to the subject a therapeutically effective amount of a purine nucleoside phosphorylase (PNPase) inhibitor and/or a PNPase purine nucleoside substrate. In some non-limiting examples, the methods can include administering a therapeutically effective amount of both a PNPase inhibitor and/or a PNPase purine nucleoside substrate. In other non-limiting examples, the PNPase inhibitor can be 8-substituted guanine and/or 8-substituted guanosine. In further non-limiting examples, the 8-substituted guanine is 8-aminoguanine and/or the 8-substituted guanosine is 8-aminoguanosine. In still further examples, the PNPase purine nucleoside substrate can be inosine or guanosine.

The methods can include treating a subject under conditions associated with PH. For example, the subject can exposed to hypoxic conditions, such as by living or working at high elevations. In other examples, the subject exhibits physiology associated with PH. For example, the subject can have body fluids with an increased ratio of guanine to guanosine, body fluids with an increased ratio of inosine to hypoxanthine, elevated right ventricular peak systolic pressure, elevated right ventricular end diastolic pressure, reduced contractility of the right cardiac ventricle, necrotizing arteritis, plexiform lesions in the lung, and/or occlusive lesions in the lung. The subject can also have a condition associated with PH, including HIV, SIV, and/or sickle cell disease.

Methods are also disclosed for treating sickle cell disease or reducing sickling of red blood cells (RBCs). The methods can include administering to the subject a therapeutically effective amount of a purine nucleoside phosphorylase (PNPase) inhibitor and/or a PNPase purine nucleoside substrate, thereby treating the sickle cell disease or reducing sickling of red blood cells (RBCs). In some examples, the PNPase inhibitor is a guanine comprising a substituent at the 8-position and/or a guanosine comprising a substituent at the 8-position. In some non-limiting examples, the 8-substituted guanine is 8-aminoguanine and/or the 8-substituted guanosine is 8-aminoguanosine. In further non-limiting examples, PNPase substrate is inosine and/or guanosine. In some embodiments, either the PNPase inhibitor or the PNPase substrate is administered. In other embodiments, both the PNPase inhibitor and the PNPase substrate are administered.

In some examples, the subject has increased sickling of red blood cells, and administering the composition decreases the sickling of red blood cells. In other examples, the subject is exposed to hypoxic and/or hypoxemic conditions, such as a subject that lives or works at high elevations. The methods can further include administering additional therapy to treat the SCD, such as hydroxyurea therapy, penicillin prophylaxis therapy, bone marrow or stem cell transplantation, immunization, pain medication, blood transfusion, anti-inflammatory therapy, anti-adhesive therapy, anti-sickling therapy, altered hemoglobin expression therapy, anti-coagulant and anti-platelet therapy, nitric oxide (NO) therapy, and/or patient measures to relieve SCD symptoms.

The foregoing and other features of this disclosure will become more apparent from the following detailed description of several embodiments, which proceeds with reference to the accompanying figures.

BRIEF DESCRIPTION OF THE FIGURES

FIG. 2A-2H: Bar graphs depict the (A) urine volume, (B) urinary sodium excretion, (C) urinary potassium excretion, D) urinary glucose excretion, E) mean arterial blood pressure (MABP), F) heart rate (HR), G) mesenteric blood flow (MBF), and H) renal blood flow (RBF) in anesthetized rats before (0-30 minutes) and after (40-70 minutes and 85-115 minutes) administration of the vehicle used in subsequent experiments. These results confirm that the vehicle has no effect and that the preparation is stable for the duration of the experiment. The values are means and SEMs (n=6).

FIG. 6A-6H: Bar graphs depict the (A) urine volume, (B) urinary sodium excretion, (C) urinary potassium excretion, D) urinary glucose excretion, E) mean arterial blood pressure (MABP), F) heart rate (HR), G) mesenteric blood flow (MBF), and H) renal blood flow (RBF) in anesthetized rats before (0-30 minutes) and after (40-70 minutes and 85-115 minutes) administration of guanine (33.5 µmoles/kg, intravenous bolus). P-values are from 1-factor analysis of variance. "a" indicates a significant difference (P<0.05; Fisher's LSD test) between the basal period (0-30 minutes) and designated treatment period. The values are means and SEMs (n=6).

FIGS. 14A-14B: The long-term effects of 8-aminoguanine (A) and 8-aminoguanosine (B) on mean arterial blood pressure (MABP) in obese Zucker Diabetic Sprague Dawley rats (ZDSD).

FIG. 16: MRI analysis of strokes in four groups of Dahl SS: Dahl SS maintained on a 8% salt diet, Dahl SS maintained on a 0.3% salt diet, Dahl SS maintained on a 8% salt diet and 10 mg/kg/day of 8-aminoguanosine, Dahl SS maintained on a 8% salt diet and 10 mg/kg/day of 8-aminoguanine.

FIGS. 21A-21D: Bar graphs depict the concentrations of 8-aminoguanine (FIGS. 21A-21B) and 8-aminoguanosine (FIG. 21C-21D) in the microdialysate obtained from the renal cortex (FIG. 21A and FIG. 21C) and renal medulla (FIG. 21B and FIG. 21D) before treatments (P1) and after intravenous administration (P2 and P3) of either vehicle (1 ml/kg), 8-aminoguanine (33.5 µmoles/kg; 1 ml/kg) or 8-aminoguanosine (33.5 µmoles/kg; 1 ml/kg). $^{a}$: Significantly different from control (P1). Values are means and SEMs.

FIGS. 24A-24D: Bar graphs depict the (FIG. 24A) urine excretion, (FIG. 24B) urinary sodium excretion, (FIG. 24C) urinary potassium excretion, and (FIG. 24D) urinary glucose excretion by the left and right kidneys during direct infusions into the left renal artery of the vehicle for 8-aminoguanosine and 8-aminoguanine during four 15-minute periods. Values are means and SEMs.

FIGS. 25A-25D: Bar graphs depict the (FIG. 25A) urine excretion, (FIG. 25B) urinary sodium excretion, (FIG. 25C) urinary potassium excretion, or (FIG. 25D) urinary glucose excretion by the left and right kidneys during direct infusions into the left renal artery of increasing doses of 8-aminoguanosine (0.1, 0.3, and 1 μmoles/kg/min) during four 15-minute periods. The p-value given for treatment×period is the interaction term in a repeated measures, 2-factor-ANOVA. $^a$: Significantly different from control (0) period for left kidney. $^b$: Significantly different from corresponding period in right kidney. Values are means and SEMs.

FIGS. 28A-28B: Decreased urinary levels of 8-aminoguanosine and 8-aminoguanine, a potent endogenous inhibitors of PNPase in adult patient with SCD. Control subjects and sickle cell disease (SCD) patients exhibited differences in urinary levels of endogenous 8-aminoguanosine (FIG. 28A) and 8-aminoguanine (FIG. 28B).

FIGS. 29A-29F: Increased PNPase activity in primates with HIV-associated associated pulmonary hypertension. Control and simian immunodeficiency virus (SIV)-infected macaques exhibited differences in urinary levels of inosine (FIG. 29A), hypoxanthine (FIG. 29B), guanosine (FIG. 29D), and guanine (FIG. 29E) as well as in urinary ratios of hypoxanthine/inosine (FIG. 29C) and guanine/guanosine (FIG. 29F).

FIGS. 31A-31E: Guanosine attenuates development of monocrotaline (MCT)-induced pulmonary hypertension (PH). Compared with control subjects, rats with MCT-induced PH exhibited differences with and without the addition of guanosine (GUA) in right ventricular peak systolic pressure (RVPSP; FIG. 31A), right ventricular end diastolic pressure (RV EDP; FIG. 31B), contractility index (FIG. 31C), right ventricular (RV) mass (FIG. 31D), and lung mass (FIG. 31E). The RV mass and lung mass were normalized to tibia length.

FIGS. 32A-32I: Guanosine inhibits MCT-induced pulmonary vascular remodeling and inflammation. Compared with control rats (FIG. 32A, FIG. 32D, and FIG. 32G), rats with monocrotaline (MCT)-induced pulmonary hypertension (PH) with (FIG. 32B, FIG. 32E, and FIG. 32H) or without the addition of 8-aminoguanosine (FIG. 32C, FIG. 32F, and FIG. 32) exhibited differences in remodeling (thickening) of the pulmonary vasculature (FIG. 32A-32F) as well as infiltration of the lungs by inflammatory ED1+ cells (FIG. 32G-32I).

FIGS. 33A-33D: PNPase inhibitor 8-aminoguanosine retards the progression of pulmonary hypertension and right ventricle dysfunction in female rats with severe angioproliferative PH. Compared with control rats, Sugen 5416+ hypoxia-induced PH rats with and without the addition of 8-aminoguanosine exhibited differences in right ventricular peak systolic pressure (RVPSP; FIG. 33A), right ventricular end diastolic pressure (RV EDP; FIG. 33B), contractility index (FIG. 33C), and the Fulton index (FIG. 33D).

FIGS. 34A-34D: Female sugen+hypoxia-treated rats develop severe angioproliferative PH with numerous occlusive (FIGS. 34A-34B) and plexiform lesions (FIG. 34C) and sporadic presence of grade-6 (necrotizing arteritis) lesions (FIG. 34D).

FIGS. 35A-35H: PNPase inhibitor 8-aminoguanosine reduces formation of occlusive (FIGS. 35A and 35D-35F) and plexiform lesions (FIGS. 35E-35F and 35G) and prevents the sporadic occurrence of necrotizing arteritis (Grade VI lesion; FIG. 35H) in female rats with severe angioproliferative pulmonary hypertension.

DETAILED DESCRIPTION

Figure 1:
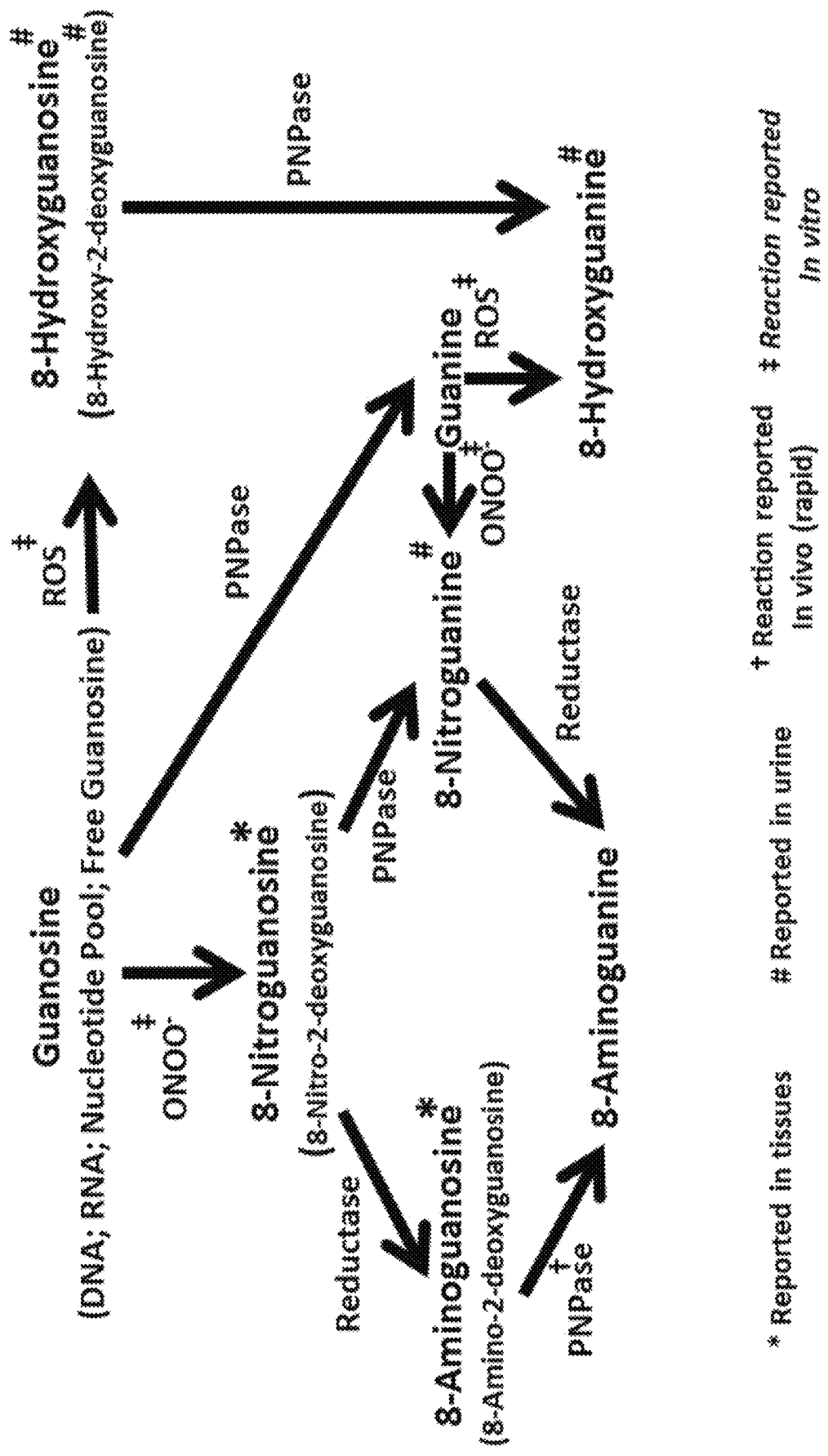
FIG. 1: Potential biochemical pathways for the formation of endogenous 8-substituted guanine and guanosine compounds.
Figure 2A:
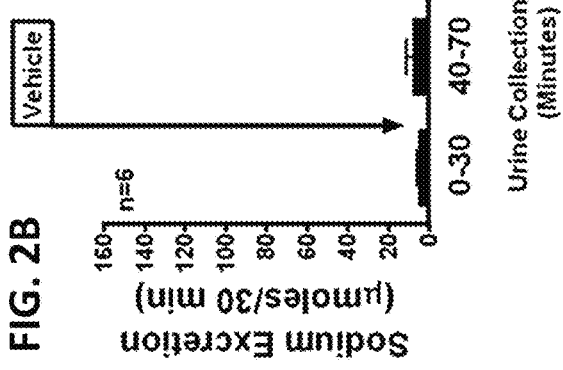
Figure 2C:
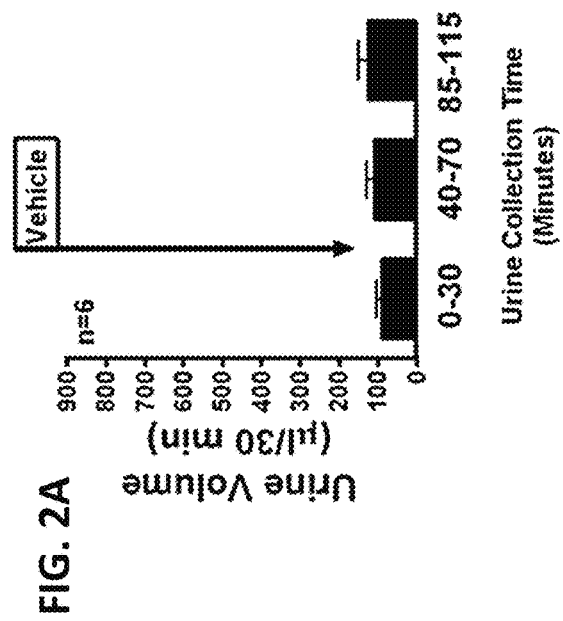
Figure 2B:
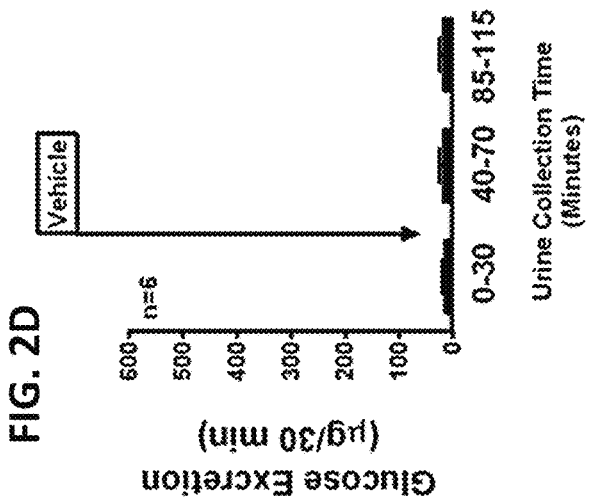
Figure 2D:
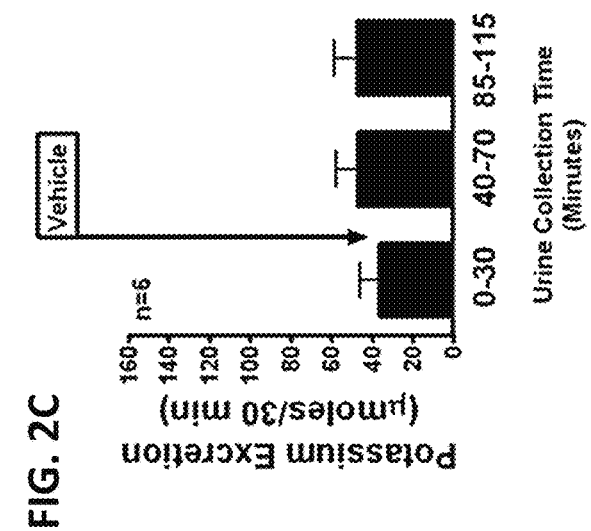
Figure 3B:
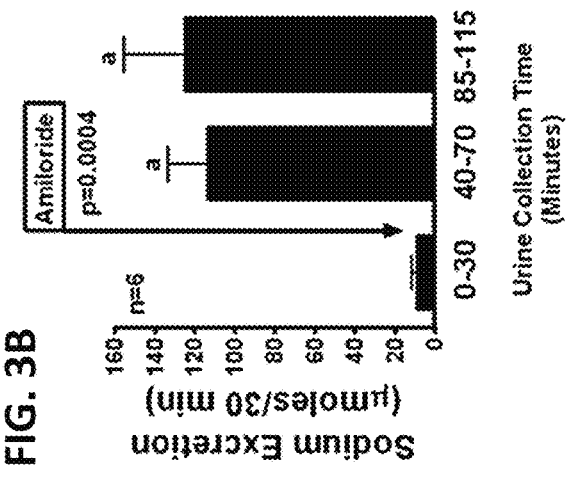
FIG. 3A-3H: Bar graphs depict the (A) urine volume, (B) urinary sodium excretion, (C) urinary potassium excretion, D) urinary glucose excretion, E) mean arterial blood pressure (MABP), F) heart rate (HR), G) mesenteric blood flow (MBF), and H) renal blood flow (RBF) in anesthetized rats before (0-30 minutes) and after (40-70 minutes and 85-115 minutes) administration of amiloride (33.5 µmoles/kg, intravenous bolus). These results confirm that the preparation is responsive to a known potassium-sparing diuretic. P-values are from 1-factor analysis of variance. "a" indicates a significant difference (P<0.05; Fisher's LSD test) between the basal period (0-30 minutes) and designated treatment period. The values are means and SEMs (n=6).
Figure 3D:
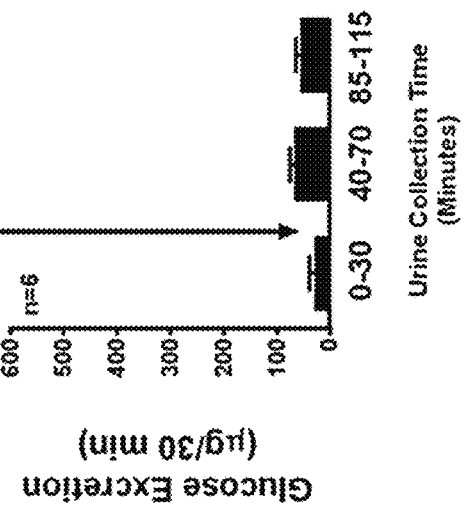
Figure 3A:
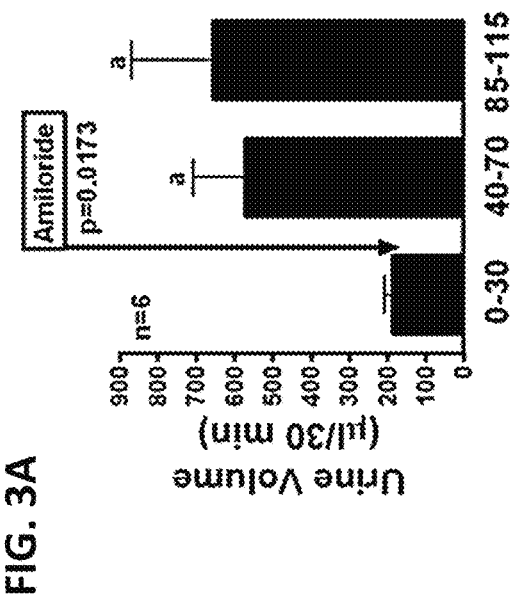
Figure 3C:
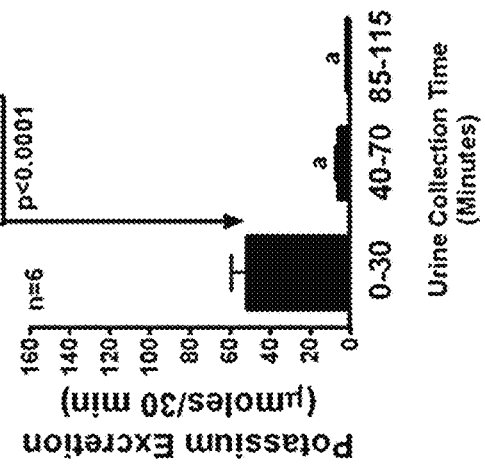
Figure 3F:
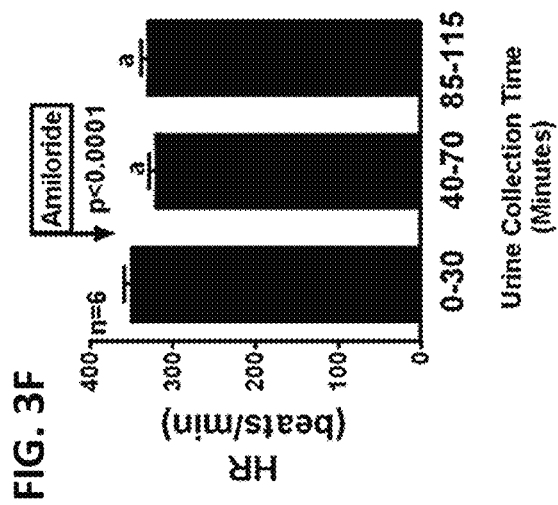
Figure 3H:
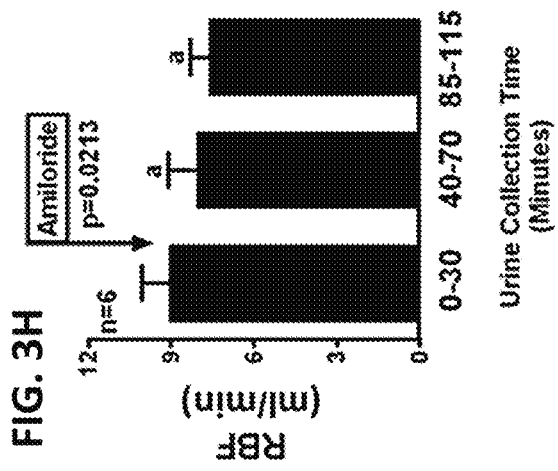
Figure 3E:
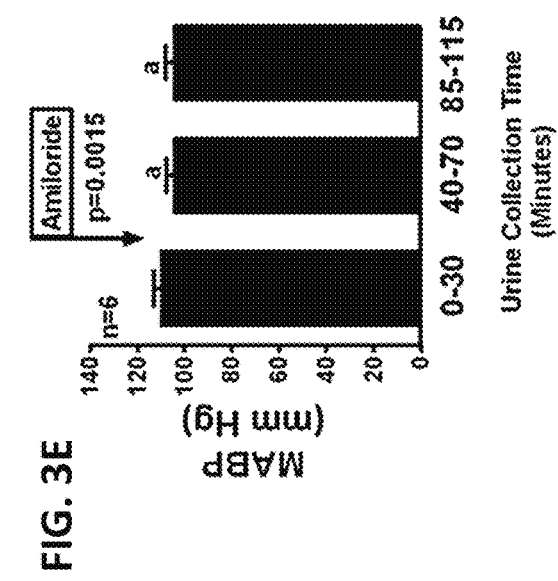
Figure 3G:
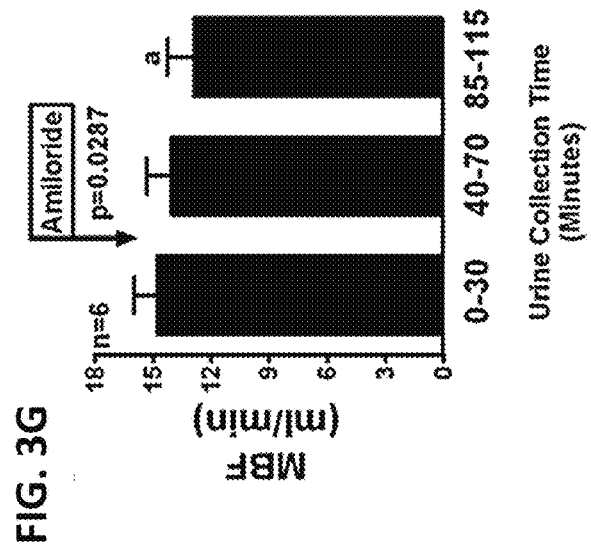
Figure 4B:
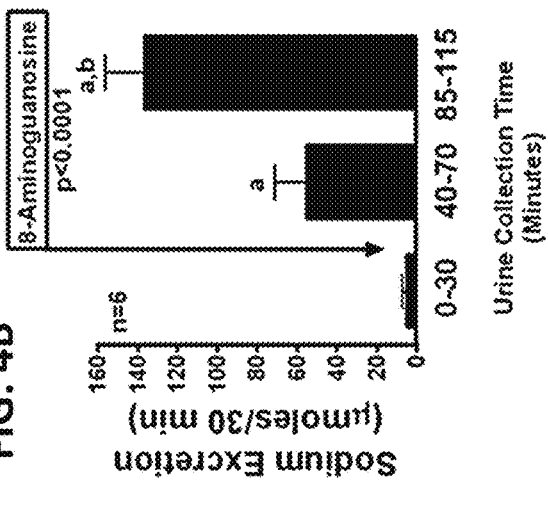
FIGS. 4A-4H: Bar graphs depict the (A) urine volume, (B) urinary sodium excretion, (C) urinary potassium excretion, D) urinary glucose excretion, E) mean arterial blood pressure (MABP), F) heart rate (HR), G) mesenteric blood flow (MBF), and H) renal blood flow (RBF) in anesthetized rats before (0-30 minutes) and after (40-70 minutes and 85-115 minutes) administration of 8-aminoguanosine (33.5 µmoles/kg, intravenous bolus). P-values are from 1-factor analysis of variance. "a" indicates a significant difference (P<0.05; Fisher's LSD test) between the basal period (0-30 minutes) and designated treatment period. The values are means and SEMs (n=6).
Figure 4D:
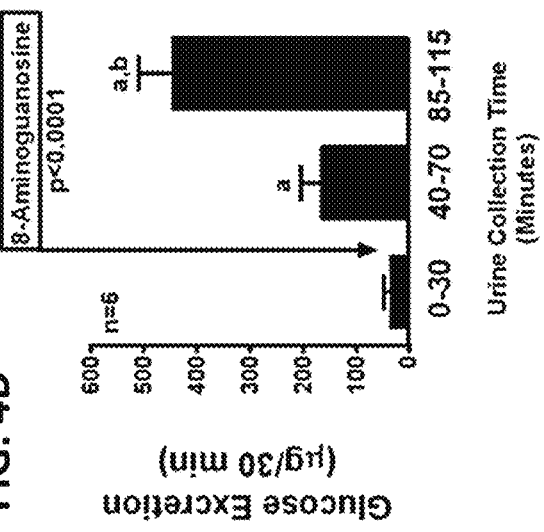
Figure 4A:
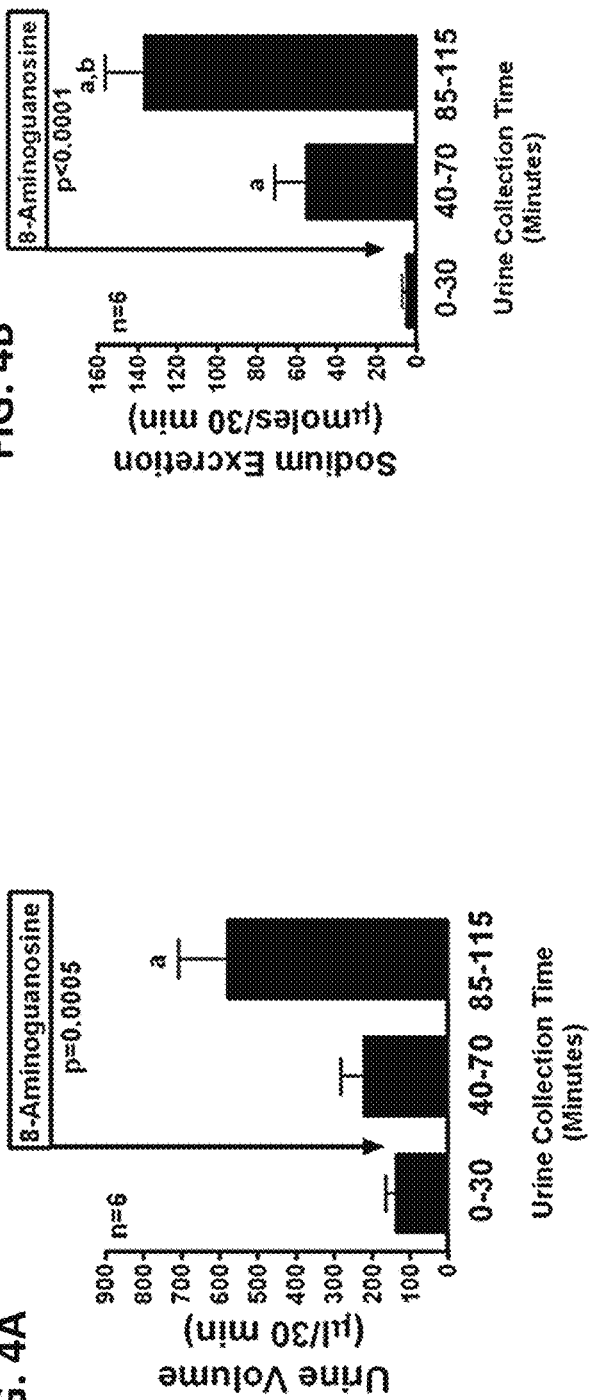
Figure 4C:
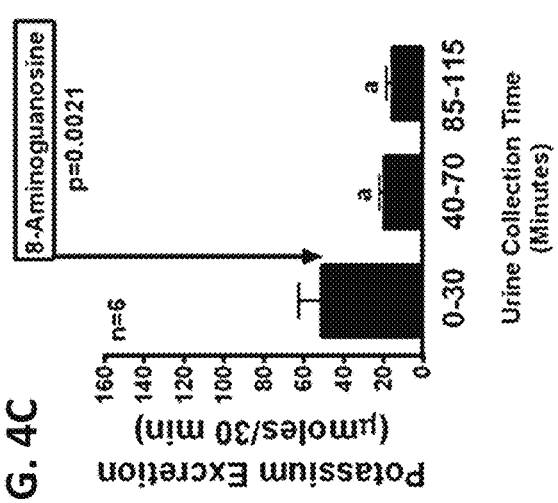
Figure 4F:
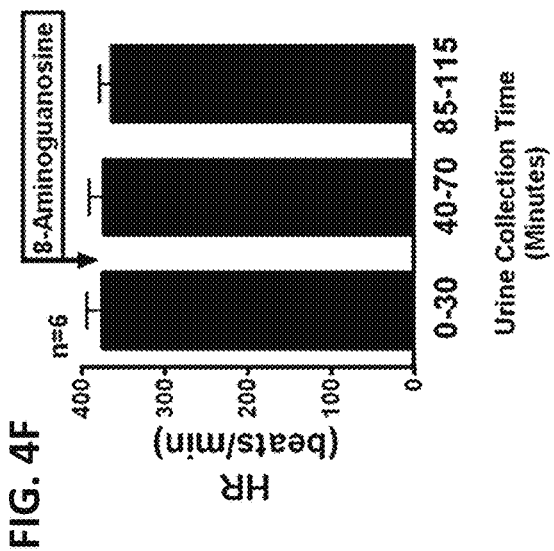
Figure 4H:
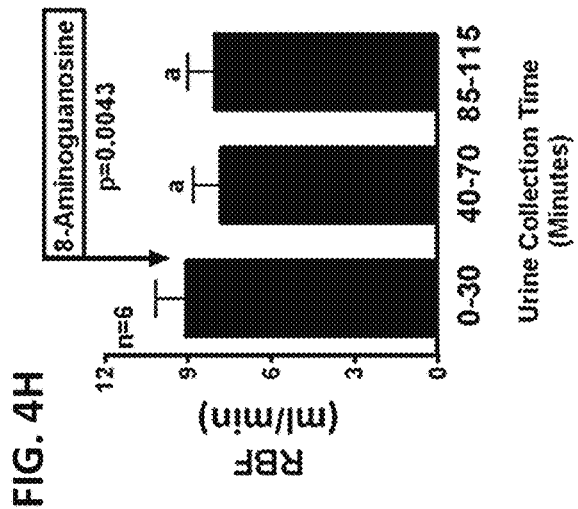
Figure 4E:
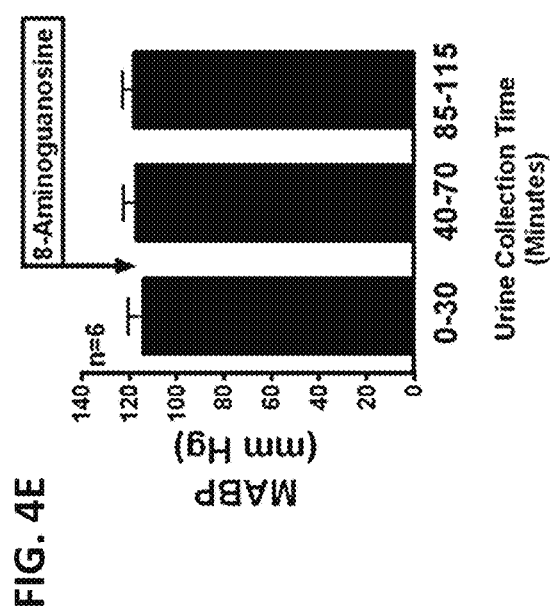
Figure 4G:
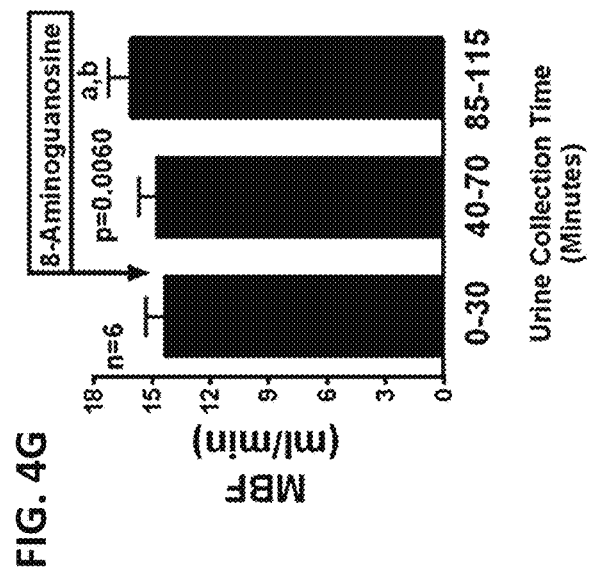
Figure 5B:
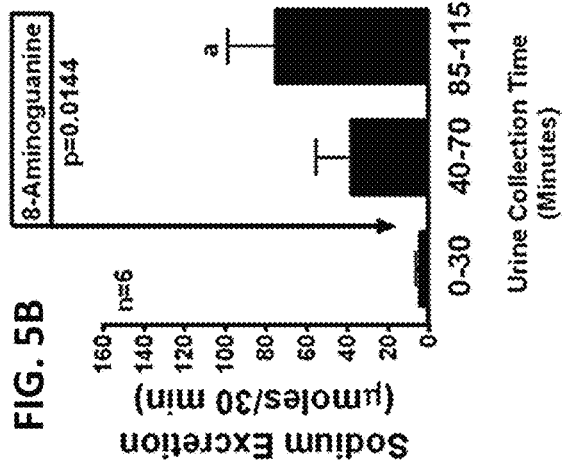
FIG. 5A-5H: Bar graphs depict the (A) urine volume, (B) urinary sodium excretion, (C) urinary potassium excretion, D) urinary glucose excretion, E) mean arterial blood pressure (MABP), F) heart rate (HR), G) mesenteric blood flow (MBF), and H) renal blood flow (RBF) in anesthetized rats before (0-30 minutes) and after (40-70 minutes and 85-115 minutes) administration of 8-aminoguanine (33.5 µmoles/kg, intravenous bolus). P-values are from 1-factor analysis of variance. "a" indicates a significant difference (P<0.05; Fisher's LSD test) between the basal period (0-30 minutes) and designated treatment period. The values are means and SEMs (n=6).
Figure 5D:
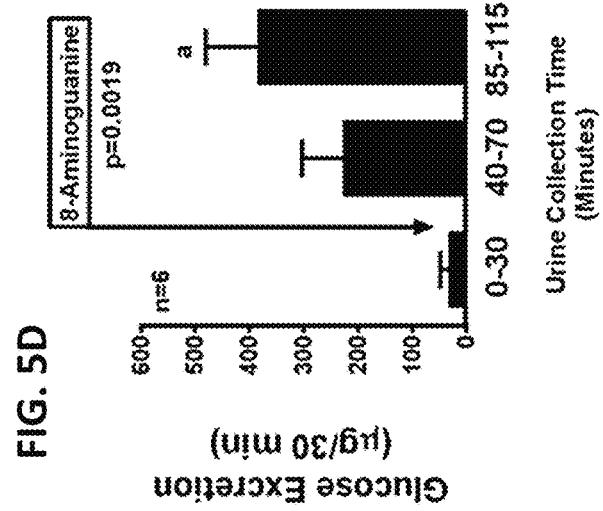
Figure 5A:
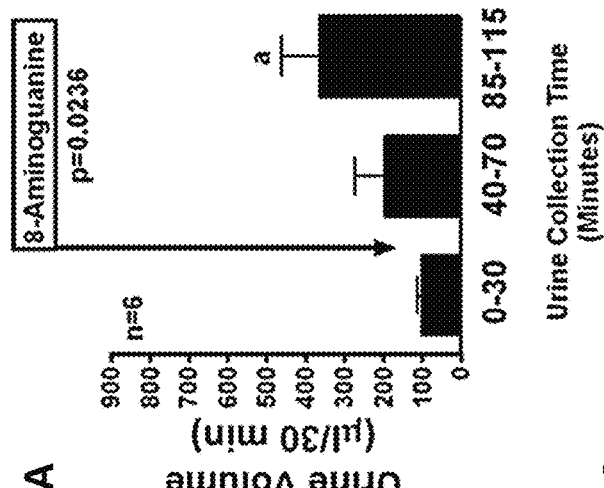
Figure 5C:
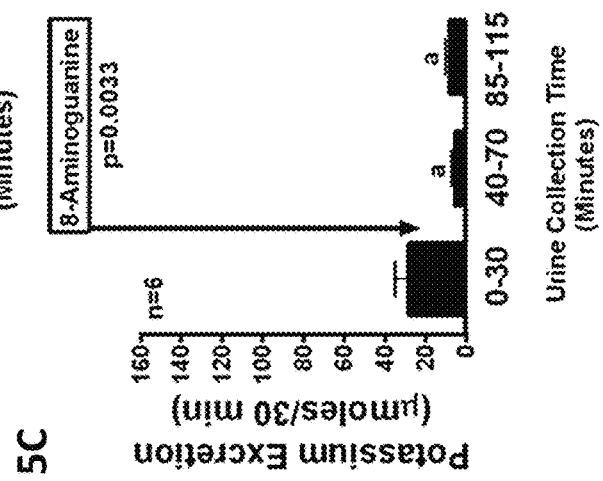
Figure 5F:
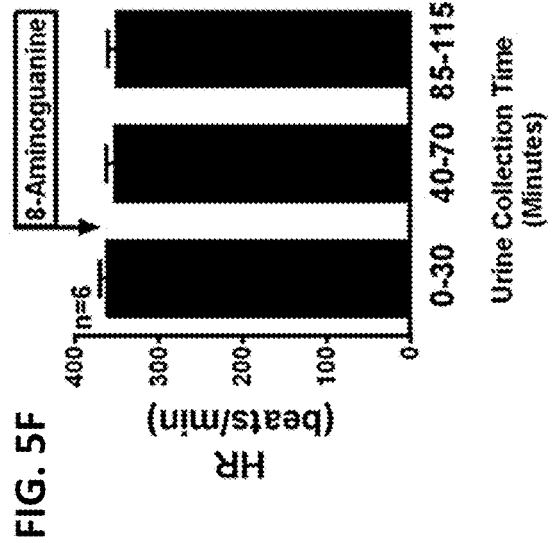
Figure 5H:
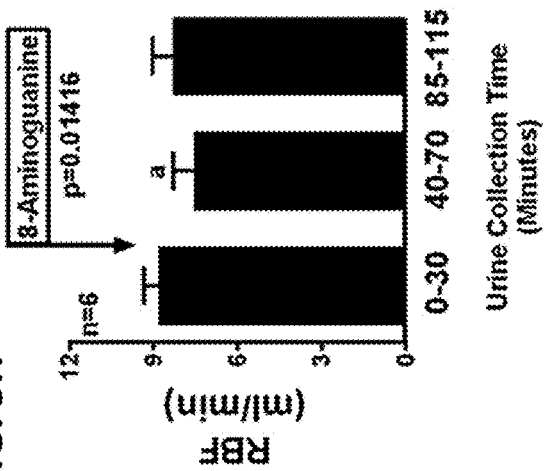
Figure 5E:
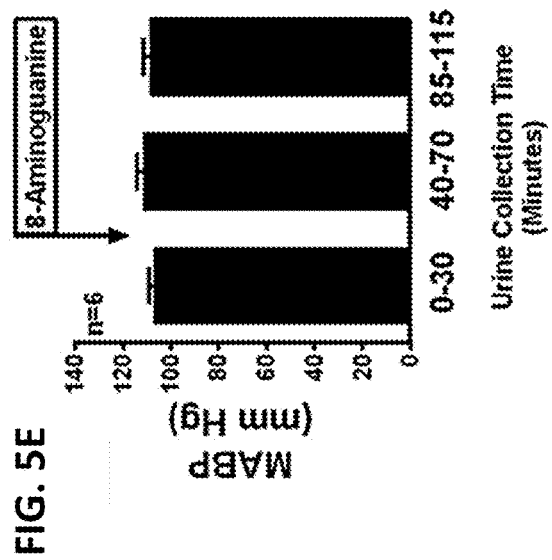
Figure 5G:
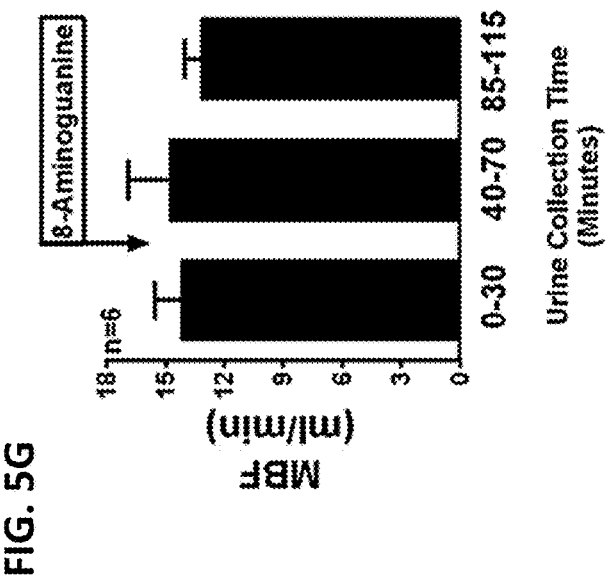
Figure 6B:
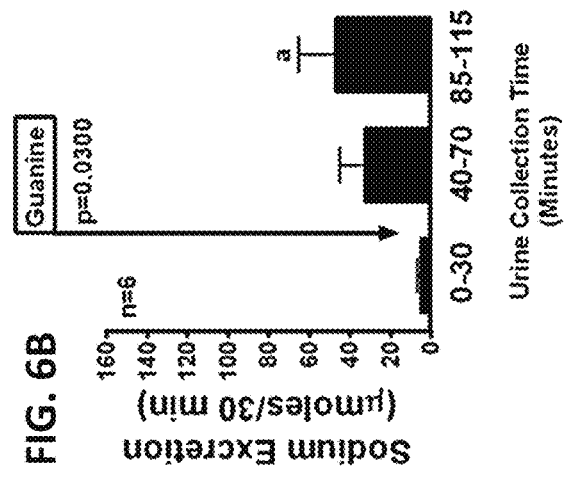
Figure 6D:
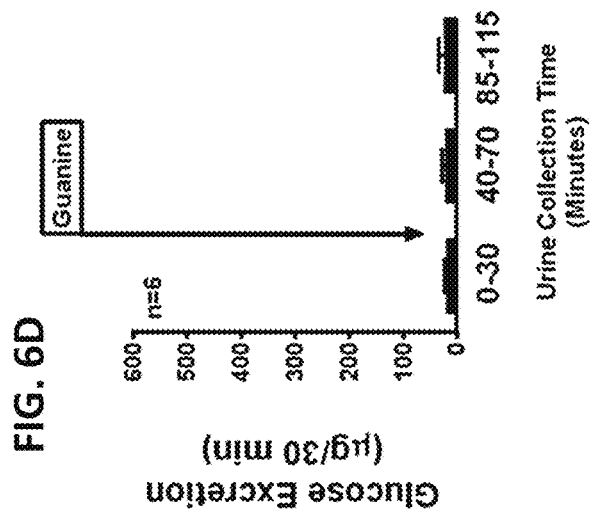
Figure 6A:
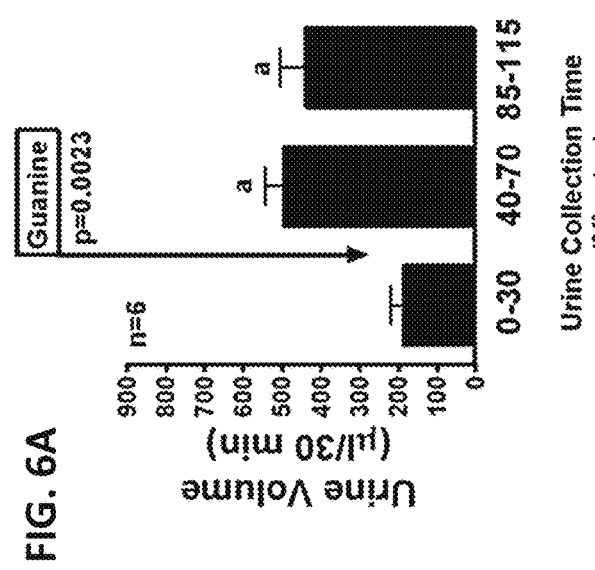
Figure 6C:
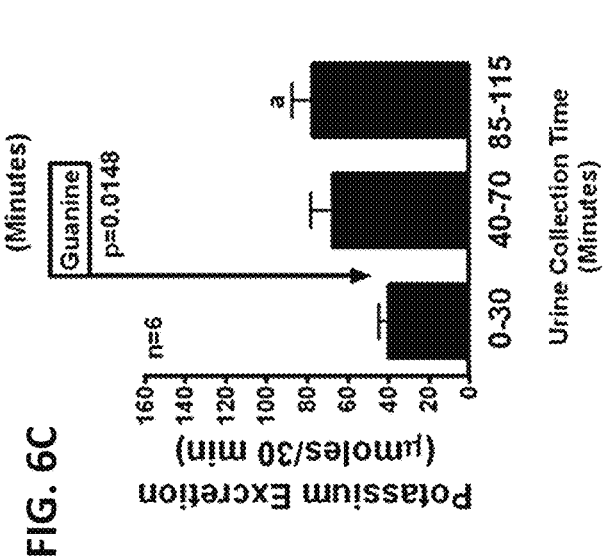
Figure 7A:
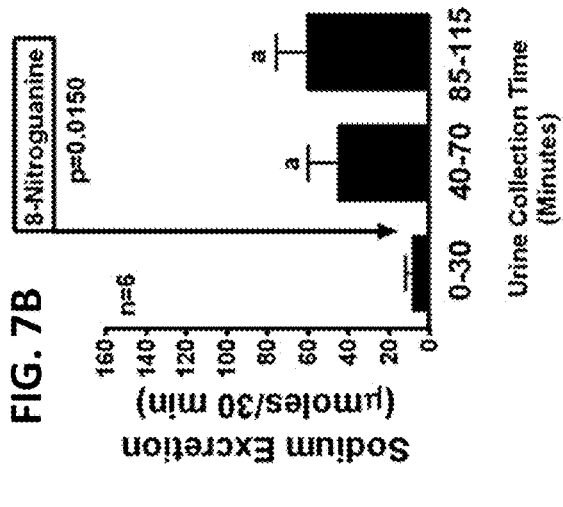
FIG. 7A-7H: Bar graphs depict the (A) urine volume, (B) urinary sodium excretion, (C) urinary potassium excretion, D) urinary glucose excretion, E) mean arterial blood pressure (MABP), F) heart rate (HR), G) mesenteric blood flow (MBF), and H) renal blood flow (RBF) in anesthetized rats before (0-30 minutes) and after (40-70 minutes and 85-115 minutes) administration of 8-nitroguanine (33.5 µmoles/kg, intravenous bolus). P-values are from 1-factor analysis of variance. "a" indicates a significant difference (P<0.05; Fisher's LSD test) between the basal period (0-30 minutes) and designated treatment period. The values are means and SEMs (n=6).
Figure 7B:
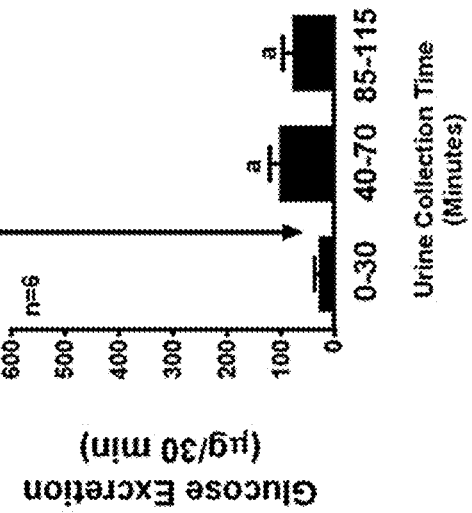
Figure 7C:
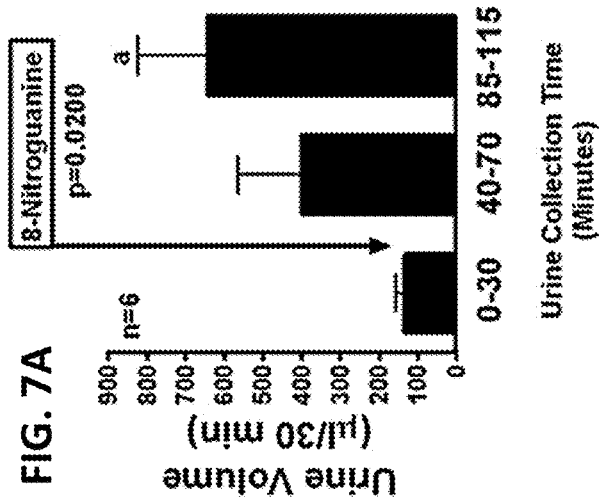
Figure 7D:
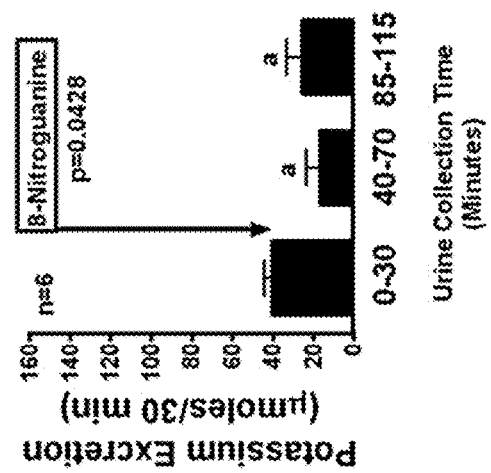
Figure 7E:
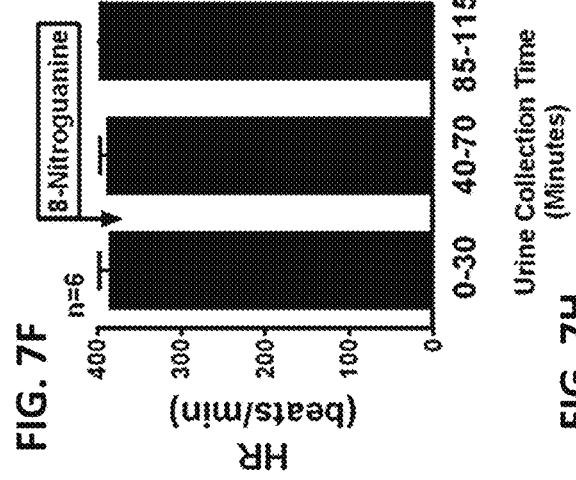
Figure 7F:
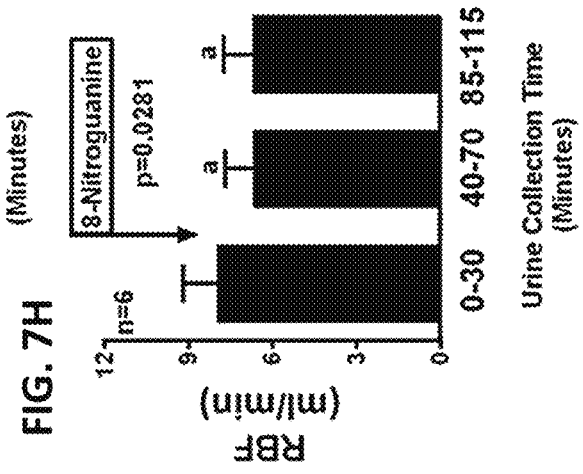
Figure 7G:
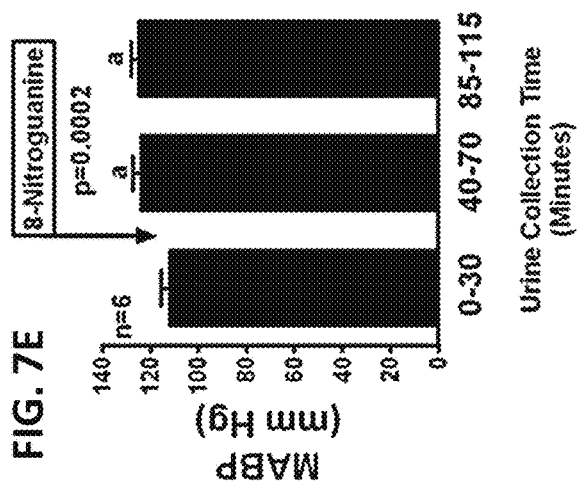
Figure 7H:
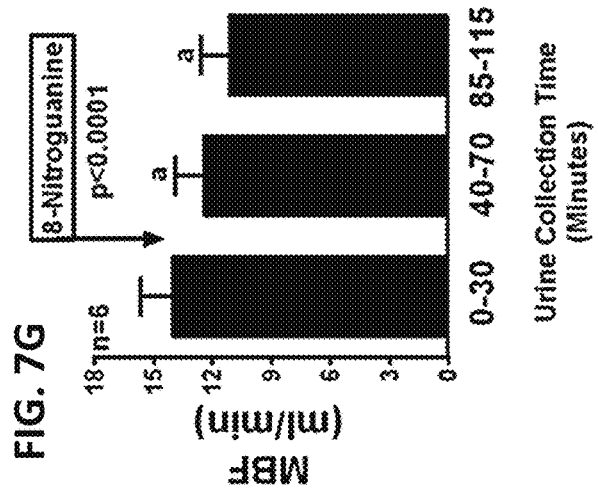
Figure 8B:
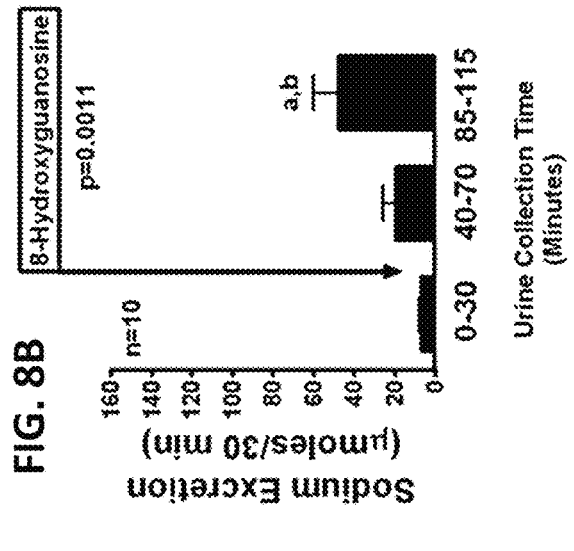
FIG. 8A-8H: Bar graphs depict the (A) urine volume, (B) urinary sodium excretion, (C) urinary potassium excretion, D) urinary glucose excretion, E) mean arterial blood pressure (MABP), F) heart rate (HR), G) mesenteric blood flow (MBF), and H) renal blood flow (RBF) in anesthetized rats before (0-30 minutes) and after (40-70 minutes and 85-115 minutes) administration of 8-hydroxyguanosine (33.5 µmoles/kg, intravenous bolus). P-values are from 1-factor analysis of variance. "a" indicates a significant difference (P<0.05; Fisher's LSD test) between the basal period (0-30 minutes) and designated treatment period. The values are means and SEMs (n=10).
Figure 8D:
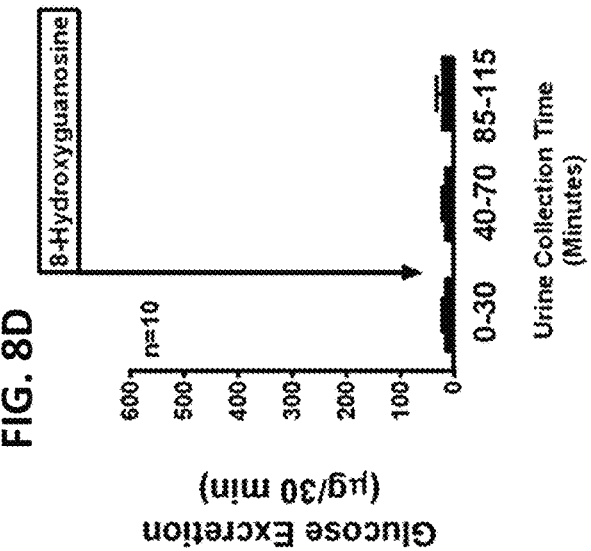
Figure 8A:
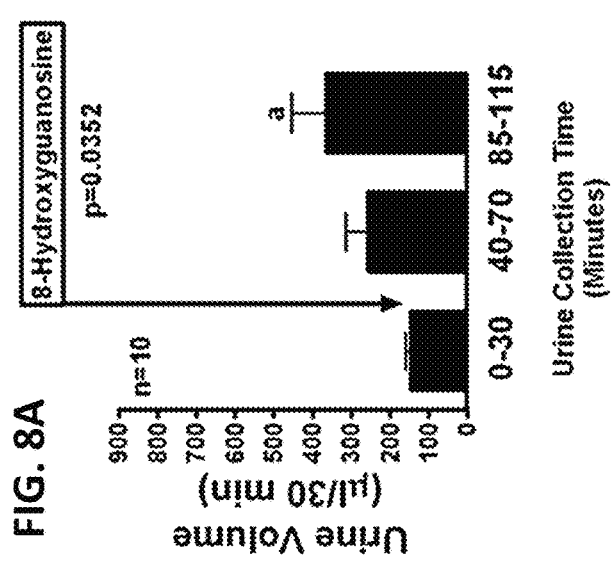
Figure 8C:
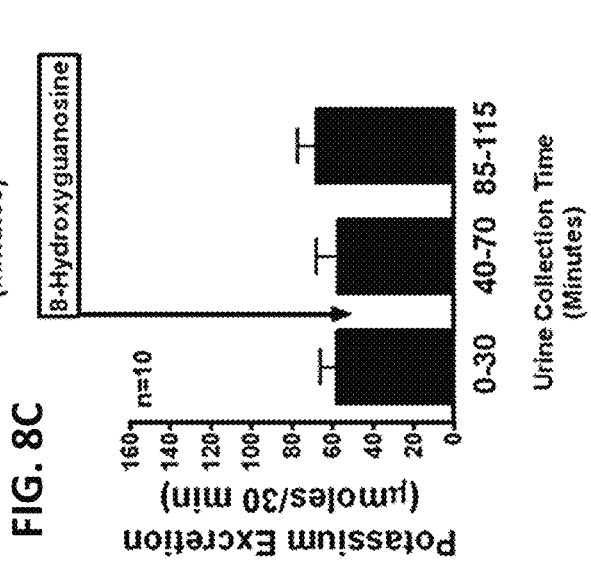
Figure 8F:
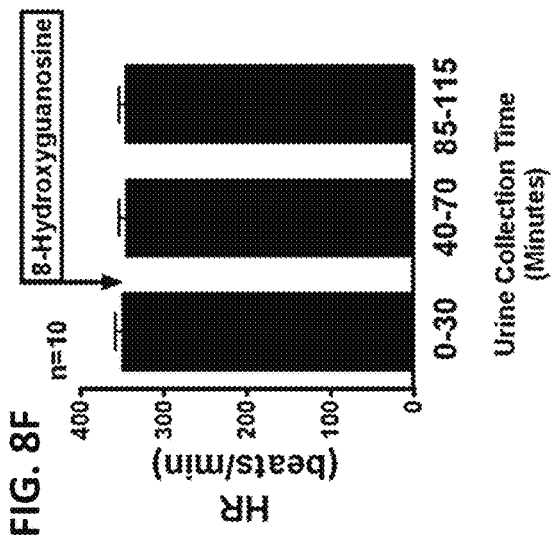
Figure 8H:
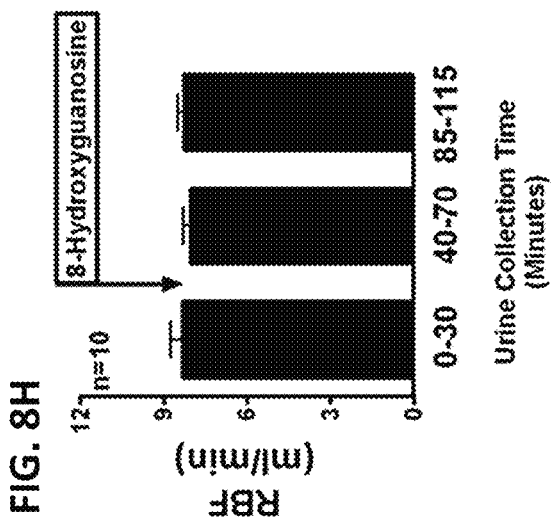
Figure 8E:
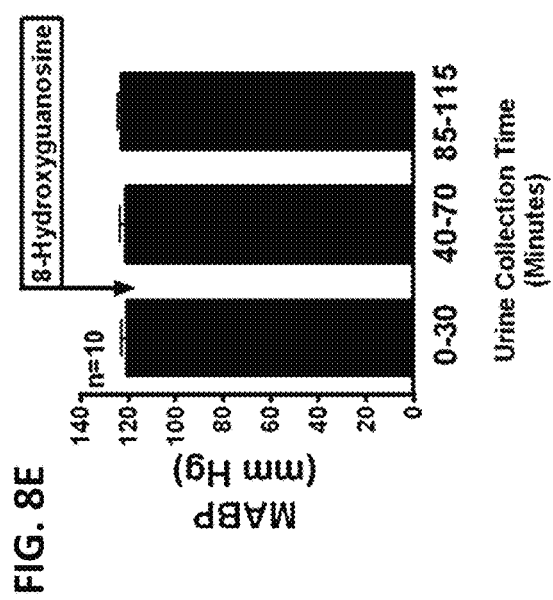
Figure 8G:
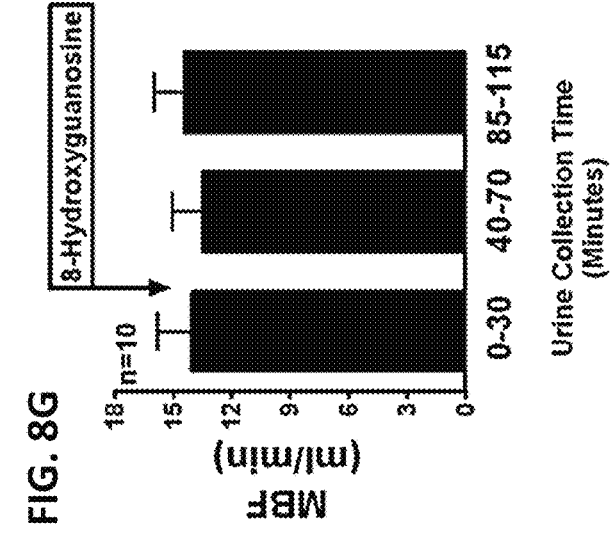
Figure 9B:
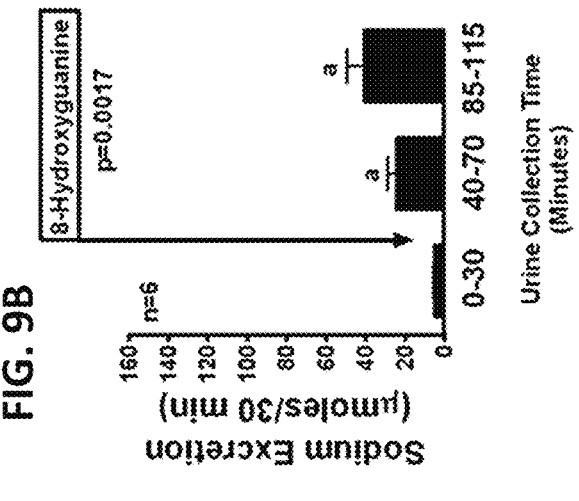
FIG. 9A-9H: Bar graphs depict the (A) urine volume, (B) urinary sodium excretion, (C) urinary potassium excretion, D) urinary glucose excretion, E) mean arterial blood pressure (MABP), F) heart rate (HR), G) mesenteric blood flow (MBF), and H) renal blood flow (RBF) in anesthetized rats before (0-30 minutes) and after (40-70 minutes and 85-115 minutes) administration of 8-hydroxyguanine (33.5 µmoles/kg, intravenous bolus). P-values are from 1-factor analysis of variance. "a" indicates a significant difference (P<0.05; Fisher's LSD test) between the basal period (0-30 minutes) and designated treatment period. The values are means and SEMs (n=6).
Figure 9D:
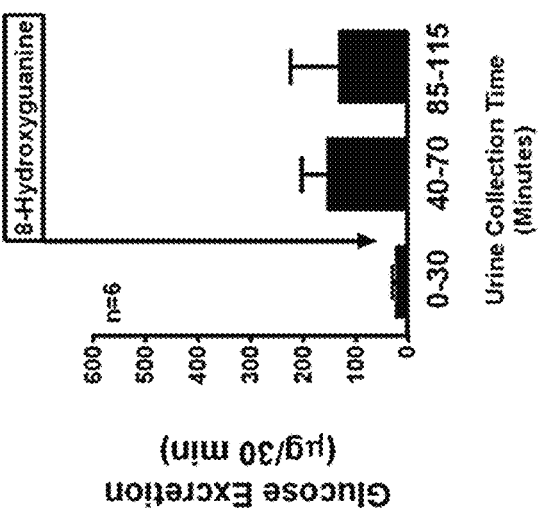
Figure 9A:
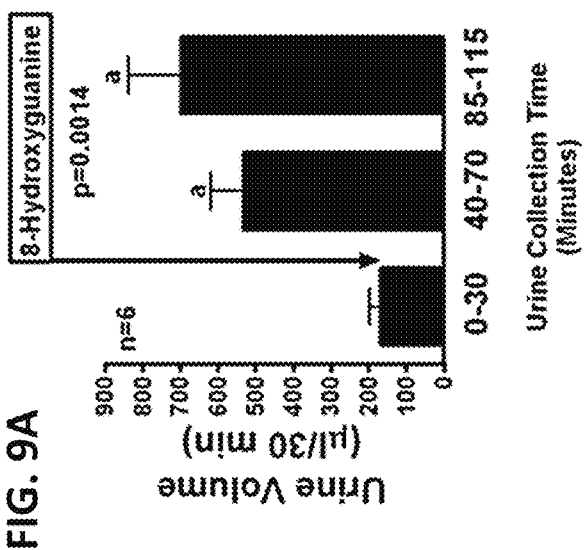
Figure 9C:
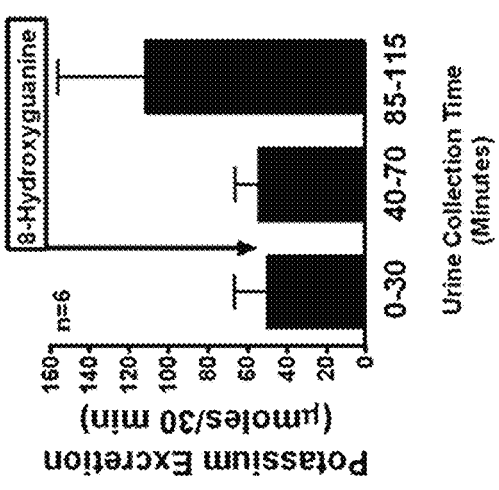
Figure 9E:
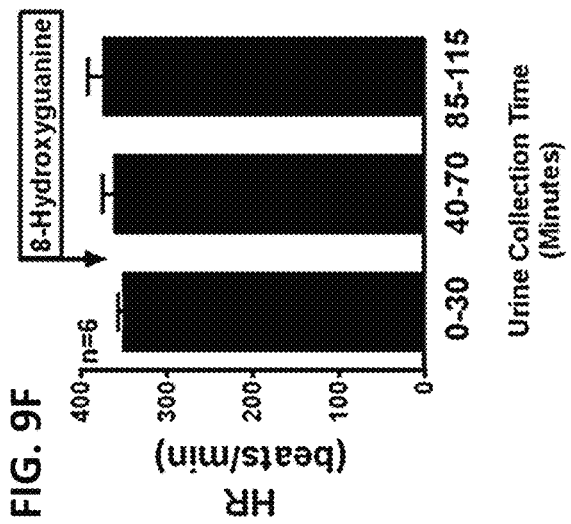
Figure 9F:
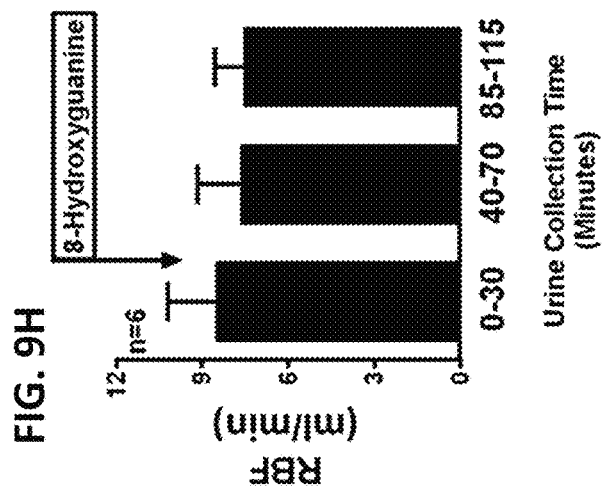
Figure 9G:
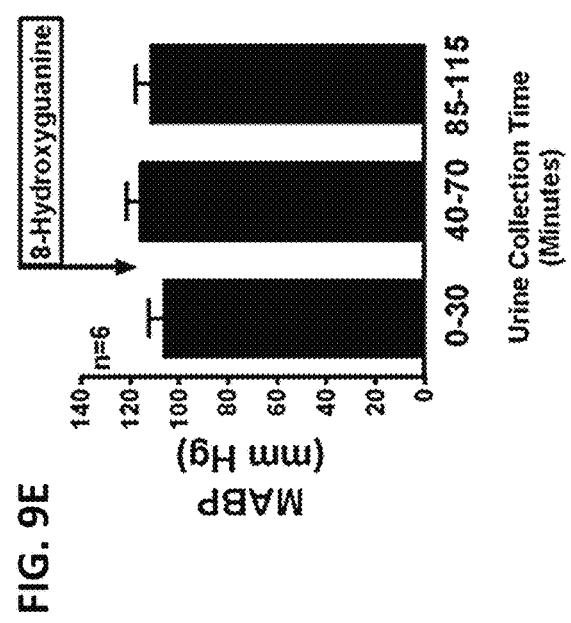
Figure 9H:
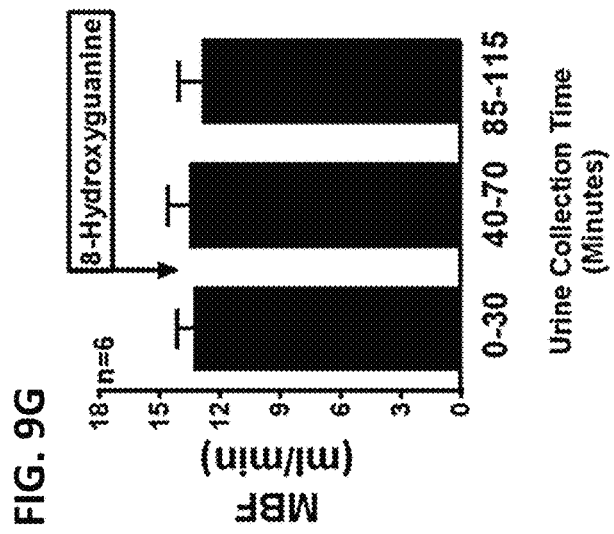
Figure 10A:
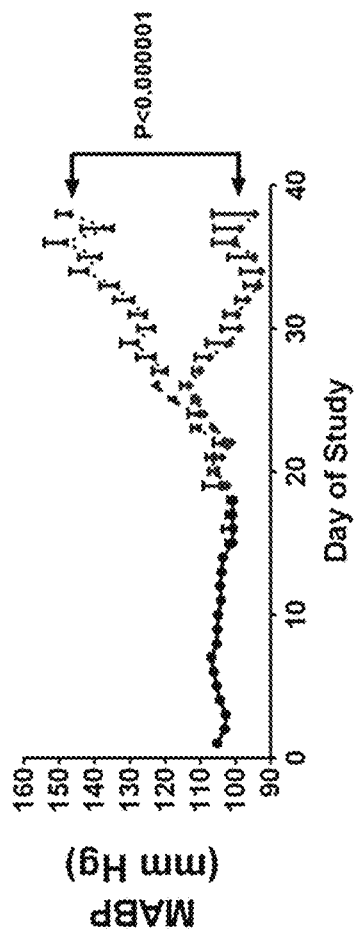
FIG. 10A-10C: Line graphs depict the long-term effects on mean arterial blood pressure (MABP) of (A) 8-aminoguanosine (10 mg/kg/day in drinking water), (B) 8-aminoguanosine (5 mg/kg/day in drinking water) and (C) 8-aminoguanine (5 mg/kg/day in drinking water) in rats made hypertension by: 1) removing one kidney, 2) administering twice weekly subcutaneous injections of deoxycorticosterone acetate, and 3) providing 1% NaCl as drinking water.
Figure 10B:
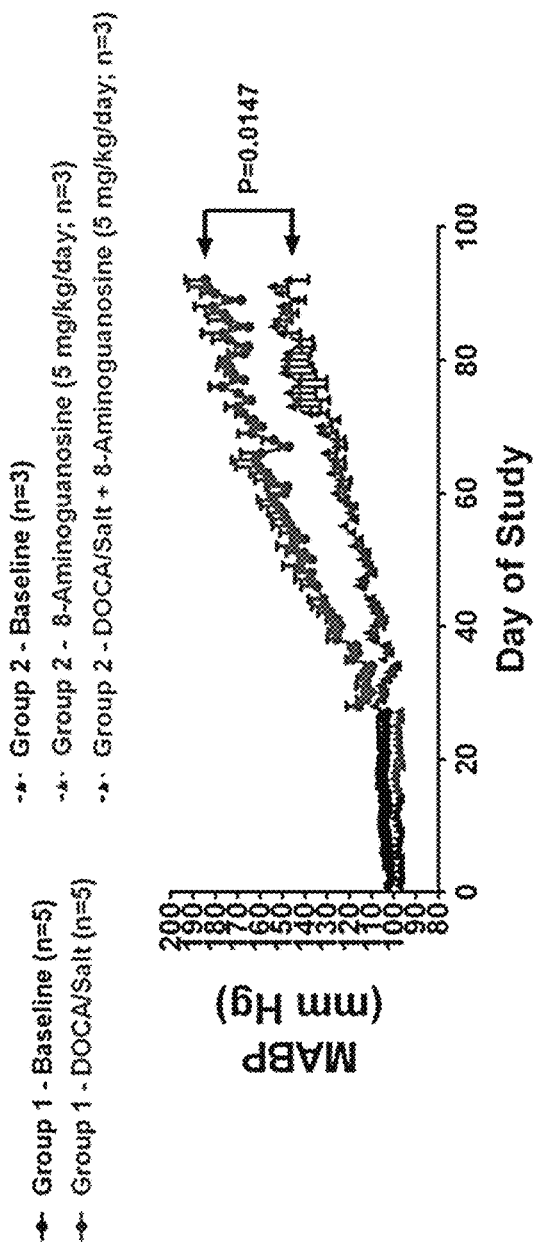
Figure 10C:
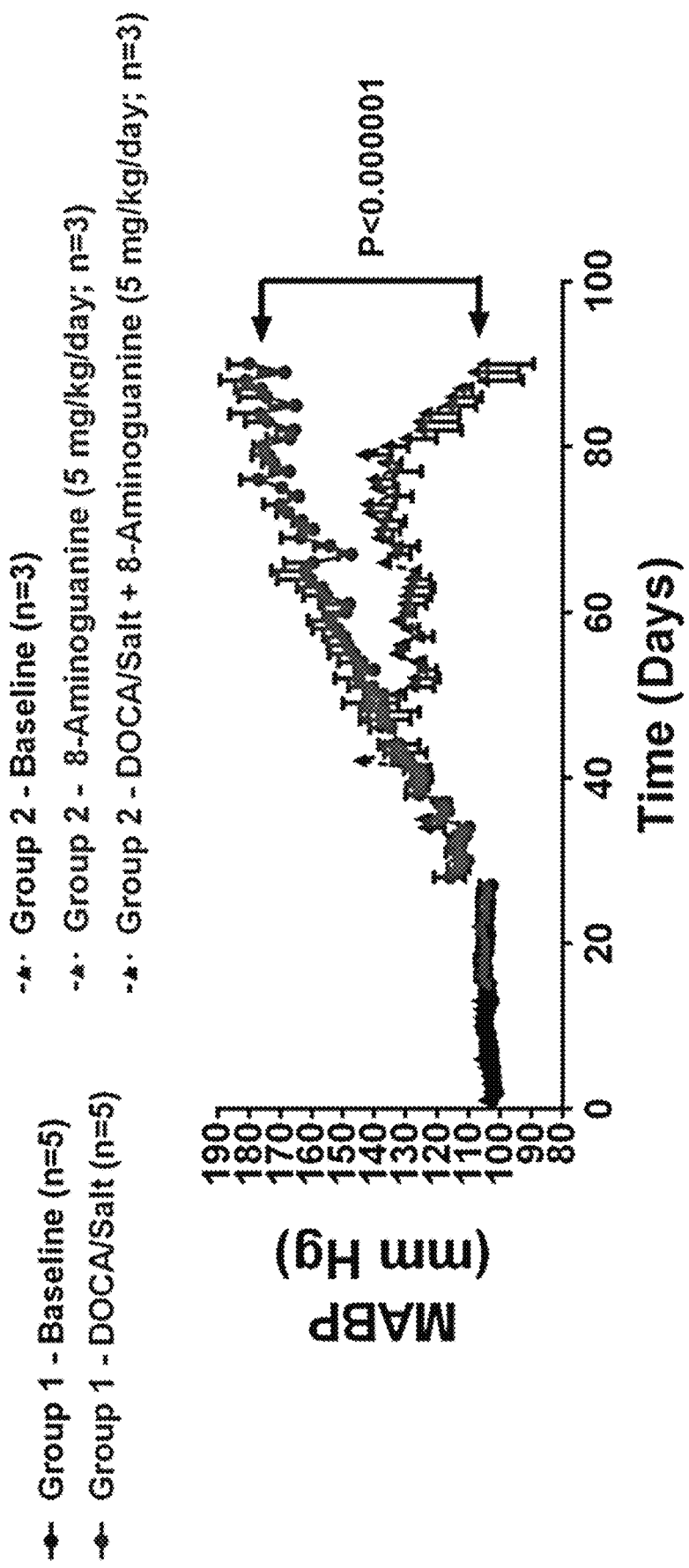

The in vivo effects of guanine comprising a substituent at the 8-position and/or a guanosine comprising a substituent at the 8-position were evaluated in several animal models. It was determined that these compounds have a variety of effects, including promoting sodium excretion, maintaining or suppressing potassium excretion, and maintaining or increasing glucose excretion. These compounds also lower arterial pressure and can be used to reduce hypertension and risk for stroke. Moreover, as the compounds promoted glucose excretion, they are of use to treat type II diabetes. It was also determined that these compounds and purine nucleoside phosphorylase (PNPase) purine nucleoside substrates can be used to treat PH, including models of sickle cell disease (SCD) and human inmmunodeficiency virus (HIV).

As these compounds are already present in red wine at low levels, fermented beverages, such as wine, can be enhanced with exogenous 8-substituted guanine and guanosine to provide a therapeutic effect.

I. TERMS

Unless otherwise noted, technical terms are used according to conventional usage. Definitions of common terms in molecular biology can be found in Lewin B, Genes VII, 1999; Kendrew et al., *The Encyclopedia of Molecular Biology*, 1994; Meyers R, *Molecular Biology and Biotechnology: a Comprehensive Desk Reference*, 1995; and other similar references.

As used herein, the singular forms "a," "an," and "the" refer to both the singular as well as plural unless the context clearly indicates otherwise.

Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

To facilitate review of the various embodiments, the following explanations of terms are provided.

Administration: To provide or give a subject an agent (such as a guanine comprising a substituent at the 8-position and/or a guanosine comprising a substituent at the 8-position) by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal, and inhalation routes.

Agent: Any polypeptide, compound, small molecule, organic compound, salt, polynucleotide, or other molecule of interest. Agent can include a therapeutic agent, a diagnostic agent or a pharmaceutical agent. A therapeutic agent is a substance that demonstrates some therapeutic effect by restoring or maintaining health, such as by alleviating the symptoms associated with a disease or physiological disorder, or delaying (including preventing) progression or onset of a disease, such as, but not limited to, hypertension or PH.

Aliphatic: A hydrocarbon, or a radical thereof, having at least one carbon atom to 50 carbon atoms, such as one to 25 carbon atoms, one to ten carbon atoms, or one to five carbon atoms, and which includes alkanes (or alkyl), alkenes (or alkenyl), alkynes (or alkynyl), including cyclic versions thereof, and further including straight- and branched-chain arrangements, and all stereo and position isomers as well.

Alkenyl: An unsaturated monovalent hydrocarbon having at least two carbon atoms to 50 carbon atoms, such as one to 25 carbon atoms, one to ten carbon atoms, or one to five carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkyl: A saturated monovalent hydrocarbon having at least one carbon atom to 50 carbon atoms, such as one to 25 carbon atoms, one to ten carbon atoms, or one to five carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkoxyl: A univalent radical R—O—, or anion R—O—, wherein R is an alkyl group.

Alkynyl: An unsaturated monovalent hydrocarbon having at least two carbon atoms to 50 carbon atoms, such as two to 25 carbon atoms, or two to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amide: —NC(O)R, wherein R is hydrogen, aliphatic, aryl, heteroaliphatic, or heteroaryl.

Amine: —NR'R, wherein each of R and R' independently are hydrogen, aliphatic, aryl, heteroaliphatic, or heteroaryl. In particular embodiments, R and R' are H, and the amine is —NH$_2$.

Animal: Living multi-cellular vertebrate organisms, a category that includes, for example, mammals and birds. The term mammal includes both human and non-human mammals. Similarly, the term "subject" includes both human and veterinary subjects.

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Blood pressure (BP): The pressure exerted by circulating blood upon the walls of blood vessels. When used without further specification, "blood pressure" usually refers to the arterial pressure in the systemic circulation ("arterial blood pressure") but can also refer to the arterial blood pressure in the pulmonary circulation. Blood pressure is usually expressed in terms of the systolic (maximum) pressure over diastolic (minimum) pressure and is measured in millimeters of mercury (mm Hg). It is one of the vital signs along with respiratory rate, heart rate, oxygen saturation, and body temperature. Mean arterial blood pressure (MABP) is a term used in medicine to describe an average blood pressure in an individual and is defined as the average arterial pressure during a single cardiac cycle. Normal resting systolic (diastolic) blood pressure in an adult is approximately 120 mm Hg (80 mm Hg), abbreviated "120/80 mm Hg". The classification of blood pressure for adults is shown below:

| Classification of blood pressure for adults[1][2] | | |
|---|---|---|
| Category | systolic, mm Hg | diastolic, mm Hg |
| Hypotension | <90 | <60 |
| Desired | 90-119 | 60-79 |
| Prehypertension | 120-139 | 80-89 |
| Stage 1 hypertension | 140-159 | 90-99 |
| Stage 2 hypertension | 160-179 | 100-109 |
| Hypertensive urgency | ≥180 | ≥110 |
| Isolated systolic hypertension | ≥160 | <90 |

Carbonate: —OC(O)OR, wherein R is hydrogen, aliphatic, aryl, heteroaliphatic, or heteroaryl.

Carbonyl: C=O, wherein the carbon located at the 8 position of guanine or guanosine forms a double bond with an oxygen atom.

Carboxyl: —C(O)OR, wherein R is hydrogen, aliphatic, aryl, heteroaliphatic, or heteroaryl.

Cardiovascular disease: Diseases of blood vessels and diseases of organs caused at least in part by diseased blood vessels. Cardiovascular disease can be one of several forms, such as systemic hypertension (also referred to as high blood pressure), pulmonary hypertension, coronary heart disease, renal vascular disease, chronic renal failure, heart failure, stroke, and rheumatic heart disease.

Control subject: A control subject is a subject that is used to provide a basis for comparison. As a comparison to subjects with or at risk for a particular condition (e.g., a subject that has diabetes, hypertension, risk for stroke, and/or pulmonary hypertension), control subjects may belong to a group of healthy subject who are studied to observe how their symptoms, traits, or behaviors compare to a group of subjects with or at risk for a particular condition.

Deoxycorticosterone acetate (DOCA)-salt hypertension rats: An art-accepted hypertensive model in which endothelium-dependent vasodilation reaction by acetylcholine and renal NO production at basal and by the stimulation of endothelin receptors (ETB) are decreased.

Diabetes mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 1 diabetes mellitus is characterized by loss of the insulin-producing 0-cells, leading to insulin deficiency. This type can be further classified as immune-mediated or idiopathic. Type 2 diabetes results from insulin resistance, a condition in which cells fail to use insulin properly, sometimes combined with an absolute insulin deficiency. This form is also called "non-insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and is diagnosed by demonstrating any one of:
  a. Fasting plasma glucose level≥7.0 mmol/l (126 mg/dl);
  b. Plasma glucose≥11.1 mmol/l (200 mg/dL) two hours after a 75 g oral glucose load as in a glucose tolerance test;
  c. Symptoms of hyperglycemia and casual plasma glucose≥11.1 mmol/l (200 mg/dl);
  d. Glycated hemoglobin (Hb A1C)≥6.5%.

Diuretic: Diuretics promote increased urine production. Thiazide diuretics inhibit sodium transport in the distal tubule; although some agents may exert some proximal tubule activity as well. Thiazide-like diuretics have the same physiological properties as thiazide-type diuretics but have different chemical properties. Loop diuretics exert their primary action on the thick ascending loop of Henle. Mineralocorticoid antagonists antagonize aldosterone at mineralocorticoid receptors. Epithelial sodium channel blockers, such as amiloride, are sodium channel blockers specific for epithelial sodium channels.

Edema: Edema is an abnormal accumulation of fluid in the tissue spaces, cavities, or joint capsules of the body, which causes swelling of the area. Edema can occur in the tissues or body spaces such as the plural cavities or the peritoneal space.

Ester: —OC(O)R, wherein R is hydrogen, aliphatic, aryl, heteroaliphatic, or heteroaryl.

Glucosuretic: Glucosuretics cause an increase in the excretion of glucose through urine.

Haloaliphatic: —CH$_2$X, —CHX$_2$, or —CX$_3$, wherein each X independently is halogen (Cl, Br, F, or I).

Halogen: bromo, fluoro, iodo, or chloro.

Heart (cardiovascular) disease: Heart disease describes a range of conditions that affect your heart. Diseases under the heart disease umbrella include blood vessel diseases, such as coronary artery disease, heart rhythm problems (arrhythmias), and heart defects you are born with (congenital heart defects), among others. Other heart conditions, such as those that affect your heart's muscle, valves, or rhythm, also are considered forms of heart disease.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, selenium, phosphorous, and oxidized forms thereof within the group.

Heteroaryl: An aryl group comprising at least one heteroatom to six heteroatoms, such as one to four heteroatoms, which can be selected from, but not limited to oxygen, nitrogen, sulfur, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group.

High altitude: An altitude that affects human or mammalian physiology. The percentage oxygen saturation of hemoglobin determines the content of oxygen in blood. After the human body reaches around 2,100 meters above sea level, the saturation of oxyhemoglobin begins to decrease. Although the human body has both short-term and long-term adaptations to altitude that allow it to partially compensate for the lack of oxygen, there is a limit to the level of adaptation. Altitudes above 8,000 meters are referred to as the "death zone," where it is generally believed that no human body can acclimatize.

Human immunodeficiency virus (HIV): A retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by HIV, as determined by antibody or western blot studies. Laboratory findings associated with this disease include a progressive decline in T cells. HIV includes HIV type 1 (HIV-1) and HIV type 2 (HIV-2). Related viruses that are used as animal models include simian immunodeficiency virus (SIV), and feline immunodeficiency virus (FIV). Treatment of HIV-1 with highly active antiretroviral therapy (HAART) has been effective in reducing the viral burden and ameliorating the effects of HIV-1 infection in infected individuals.

Hydroxyl: —OH.

Hypertension: Hypertension is a chronic cardiovascular disease in which the arterial blood pressure is elevated and is associated with an increased risk of pathological effects. Hypertension makes it harder for the heart to pump blood because of the increased pressure in the arteries, which, over time, leads to heart failure. Continuous hypertension is one of the risk factors for stroke, heart attack, heart failure, chronic renal failure, and others. In fact, hypertension is the single most important risk factor for stroke. It causes about 50 percent of ischemic strokes and increases the risk of hemorrhagic stroke. For example, sustained systolic blood pressure of greater than 140 and sustained diastolic blood pressure of greater than 90 are associated with adverse long-term cardiovascular sequelae. Mild to moderate hypertension is usually asymptomatic, but accelerated hypertension is associated with headache, confusion, nausea, vomiting, and others. The best way to control hypertension is to change one's lifestyle. Some of the changes include weight and stress reduction, reducing salt, sugar, fat intake, and others. For chronic problems, antihypertensive drugs are prescribed. Commonly prescribed drugs include ACE inhibitors, such as fosinopril and captopril; calcium channel blockers, such as amlodipine and diltiazem; and diuretics, such as chlortalidone. However, none of these drugs offer cure from disease.

Both systemic and pulmonary hypertension are included. Systemic hypertension is hypertension that affects the systemic circulation. Systemic circulation is the part of the cardiovascular system that carries oxygenated blood away from the heart to the body and returns deoxygenated blood back to the heart. Pulmonary hypertension (further described below) is hypertension that affects the pulmonary circulation. Pulmonary circulation is the portion of the circulatory system that carries deoxygenated blood away from the right ventricle of the heart to the lungs and returns oxygenated blood to the left atrium and ventricle of the heart.

Hypokalemia: A lower than normal potassium level in the bloodstream. Potassium is important for proper function of nerve and muscles cells, particularly heart muscle cells.

Inhibiting or treating a disease: Inhibiting the full development of a disease or condition, for example, in a subject who is at risk for a disease, such as hypertension (including pulmonary and systemic), stroke, diabetes, sickle cell disease (SCD), and human inmmunodeficiency virus (HIV). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, reduced tumor burden, reduce metastases, a slower progression of the disease, an improvement in the overall health or well-being of the subject, or by other parameters well known in the art that are specific to the particular disease. "Prophylaxis" is a treatment administered to a subject who does not exhibit signs of a disease or exhibits only early signs for the purpose of decreasing the risk of developing pathology.

Kidney disease: Kidney damage leading to pathological changes in kidney structure or function as a result of a pathological condition intrinsic to (originating within) the kidney or a pathological condition extrinsic to (originating outside) the kidney that nonetheless damages the kidney and causes dysfunction of a kidney. Kidney disease includes nephritis and nephrosis. Nephritis is inflammatory kidney disease, while nephrosis is non-inflammatory nephropathy. Kidney disease usually causes kidney failure (renal failure), with the amount depending on the type of disease. Generally, in kidney disease there are structural changes to the kidney that result in changes in the function of the organ. Kidney disease includes acute and chronic renal failure, such as a result of diabetes and/or hypertension Lung Disease: Pathological conditions affecting the organs and tissues that make gas exchange possible in higher organisms, including conditions of the upper respiratory tract, trachea, bronchi, bronchioles, alveoli, and pleura and pleural cavity. Lung disease includes pulmonary hypertension, chronic obstructive pulmonary disease, asthma, pulmonary vascular disease, pleural effusion, and lung cancer.

Natriuresis: The process of sodium excretion in the urine through the action of the kidneys. It is promoted by ventricular and atrial natriuretic peptides and inhibited by aldosterone. Natriuresis lowers the amount of sodium in extracellular compartments of the body and thereby lowers the volume of these extracellular compartments as homestatic mechanisms remove water to maintain sodium concentrations constant. By decreasing extracellular fluid volumes, diuretic drugs can be used to treat medical conditions such as hypertension and edema associated with heart, kidney, and liver diseases.

Natriuretic: Natriuretics cause an increase in the excretion of sodium through urine.

Nitro: —$NO_2$.

Nitroso: —NO.

Pharmaceutically acceptable carrier: As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, e.g., *Remington's Pharmaceutical Sciences*, 1289-1329, 1990, incorporated herein by reference). Except insofar as any conventional carrier is incompatible with the active ingredient, its use in the therapeutic or pharmaceutical compositions is contemplated.

PNPase: Purine nucleoside phosphorylase, a glycosyltransferase, is an enzyme that catalyzes a chemical reaction between purine nucleoside (e.g., inosine or guanosine) and phosphate.

Pre-diabetes: A condition in which some, but not all, of the criteria for diabetes are met. For example, as subject can be identified has having pre-diabetes if they have impaired glucose tolerance, such as measure by an oral glucose tolerance test (OGTT), alone or in combination with impaired fasting glucose regulation. In an additional example, a subject can have impaired fasting glycaemia or impaired fasting glucose (IFG). Subjects with fasting glucose levels from 110 to 125 mg/dl (6.1 to 6.9 mmol/1) are considered to have impaired fasting glucose. Subjects with plasma glucose at or above 140 mg/dL (7.8 mmol/L), but not over 200 mg/dL (11.1 mmol/L), two hours after a 75 g oral glucose load are considered to have impaired glucose tolerance.

Prodrug: A medication or compound that, after administration, is metabolized into a pharmacologically active drug or compound. For example, the prodrugs 8-amino-3',5'-cGMP; 8-amino-GTP; 8-amino-GDP; and 8-amino-GMP can be used therapeutically in the same way as 8-aminoguanosine because they are metabolized to the active form, 8-aminoguanosine, after administration.

Pulmonary hypertension (PH): A disease characterized by a mean rise in pulmonary arterial pressure>25 mmHg at rest (>30 mmHg following exercise). The physiological changes can further include formation of necrotizing arteritis as well as plexiform and occlusive lesions (see Tuder et al., JACC, 54:1, S3-S9, 2009; Moraes et al., Clin. Cardiol., 20, 676-682, 1997, both of which are incorporated herein by reference). This disease is progressive, with various origins, and is associated with a poor prognosis that results in right heart dysfunction.

Pulmonary hypertension is divided into groups based on the disease etiology. Group 1 PH encompasses diseases where increased pulmonary vascular resistance is due to pre-capillary micro-angiopathy (diagnosed as a pre-capillary wedge pressure<15 mmHg). Within this group lies idiopathic pulmonary arterial hypertension (IPAH) and familial pulmonary arterial hypertension, associated pulmonary arterial hypertension, pulmonary arterial hypertension with venous/capillary involvement, and persistent pulmonary hypertension of the newborn. Group 2 includes PH that results from left heart diseases, Group 3 encompasses PH associated with lung disease/hypoxemia (e.g., COPD), and Group 4 encompasses PH associated with chronic thromboembolic disorders. See Patent Pub. Nos. US20170088897 and US20160346280, both of which are incorporated herein by reference.

Sickle cell disease (SCD): Also known as hemoglobinopathy, SCD is a group of congenital blood disorders (e.g., sickle cell anemia) resulting from the presence of a mutated form of hemoglobin, which is referred to as sickle hemoglobin (also known as hemoglobin S, Hb type S, or HbS; see Bender, GeneReviews: Sickle Cell Disease, 2017, https://www.ncbi.nlm.nih.gov/books/NBK1377/; Kotila, Annals of Ibadan Postgraduate Medicine. 8(1): 25-29, 2010; Figueiredo, Rev Bras Hematol Hemoter, 37(3):150-152, 2015; Chaturvedi et al., American Journal of Hematology, 91:1, 5-14, 2016; Telen, F1000Research, 4(F1000 Faculty Rev):1050 L, 12 pages, 2015, all of which incorporated herein by reference). The resultant HbS is prone to polymerization with other hemoglobin molecules under low oxygen tension, which adversely affects erythrocytes (red blood cells or RBCs), such as changing the shape of the RBCs from a round shape to a sickle shape. Sickle-shaped RBCs can become trapped in small blood vessels and block blood flow to tissues. In addition to causing organ damage, the lack of oxygen in the tissues can cause attacks of sudden, severe pain, called pain crises, which can occur without warning, and a person must often go to a hospital for effective treatment.

Sickle cells also do not last as long as normal blood cells; due to a constant shortage of red blood cells, the blood cannot carry enough oxygen to the body, and patients develop anemia. Other complications from SCD include hand-foot syndrome (i.e., where sickle-shaped RBCs block blood vessels in the hands or feet), splenic sequestration (i.e., where the splenic vessels are blocked by sickle cells), delayed growth, neurological complications (e.g., ischemic stroke and silent cerebral infarcts), eye problems (including blindness and retinal damage), skin ulcers in the legs, priapism, gallstones, and sickle chest syndrome (i.e., a severe type of sickle cell crisis; also known as acute chest syndrome).

Sickle cell disease can take multiple forms, including hemoglobin SS disease (HbSS), hemoglobin SC disease (HbSC), hemoglobin Sβ+ thalassemia (HbSβ+; also known as HbSB+ and Hbβ$^S$β+), hemoglobin Sβ° thalassemia (HbSβ°; also known as HbSB0 and Hbβ$^S$β°), hemoglobin SD (HbSD), hemoglobin SE (HbSE), hemoglobin SO (HbSO), and sickle cell trait (SCT; also known as HbAS). Although most people with SCT do not typically have symptoms, they can pass the gene for abnormal hemoglobin on to their children, and in rare cases, people with SCT might experience complications of SCD, such as pain crises.

Stroke: A condition caused by loss of blood supply to the brain resulting in loss of brain functions within minutes, such as inability to move one or more limb(s), inability to understand or formulate speech, inability to see one side of the visual field, numbness, balance problem, altered breathing and heart rate, etc. Risk factors for stroke are hypertension, diabetes, obesity, high blood cholesterol levels, etc.

Subject: As used herein, the term "subject" refers to a mammal and includes, without limitation, humans and veterinary subjects, including domestic animals (e.g., dogs or cats), farm animals (e.g., cows, horses, or pigs), and laboratory animals (e.g., mice, rats, hamsters, guinea pigs, pigs, rabbits, dogs, or monkeys).

Substituent: As used herein, the term "substituent" refers to an atom or group of atoms taking the place of another atom or group or occupying a specified position in a molecule. For example, a hydrogen at the 8 position of a purine can be replaced by a substituent, such as an amine, nitro, or hydroxyl.

Therapeutically effective amount: The term "therapeutically effective amount" refers to that amount of an active ingredient (such as a 8-substituted guanine, 8-substituted guanosine, guanosine, and inosine) that is sufficient to effect treatment when administered to a mammal in need of such treatment. The therapeutically effective amount will vary depending upon the subject and disease condition being treated, the weight and age of the subject, the severity of the disease condition, the manner of administration and the like, which can readily be determined by a prescribing physician.

Treating a disease: "Treatment" refers to a therapeutic intervention that ameliorates a sign or symptom of a disease or pathological condition, such as such as hypertension (including pulmonary and systemic), stroke, diabetes, sickle cell disease (SCD), and human inmmunodeficiency virus (HIV). Treatment can also induce remission or cure of a condition or can reduce the pathological condition, such as such as hypertension (including pulmonary and systemic), stroke, or diabetes. In particular examples, treatment includes preventing a disease, for example by inhibiting the full development of a disease, such as decreasing the ability of pulmonary hypertension to generate necrotizing arteritis. Prevention of a disease does not require a total absence of disease.

II. DESCRIPTION OF SEVERAL EMBODIMENTS

It is disclosed herein that guanosine, guanine, inosine, hypoxanthine, and/or adenosine compounds with a substituent (i.e., an atom or group of atoms, such as amine, nitro, or hydroxyl, taking the place of another atom or group, such as a hydrogen, or occupying a specified position in a molecule) at the 8 position as well as inosine and guanosine can be used therapeutically. The 8-substituted guanine and guanosine compounds are referred to as Formula 1 (guanine with a substituent at the 8 position) and Formula 2 (guanosine with a substituent at the 8 position). Other 8-substituted compounds are also possible, including Formula 3 (inosine with a substituent at the 8 position), Formula 4 (hypoxanthine with a substituent at the 8 position), and Formula 5 (adenosine with a substituent at the 8 position). In other embodiments, any prodrug (i.e., a medication or compound that, after administration, is metabolized into a pharmacologically active drug) of the compounds could be used (e.g., the prodrugs 8-substituted 3',5'-cyclic guanosine monophosphate (cGMP); 8-substituted guanosine-5'-triphosphate (GTP); 8-substituted guanosine-5'-triphosphate (GDP); and 8-substituted GMP, such as 8-amino-3',5'-cGMP; 8-amino-GTP; 8-amino-GDP; and 8-amino-GMP, can be used therapeutically in the same way as 8-substituted guanosine).

The general chemical structures of these compounds are shown below and are further defined in the Terms section.

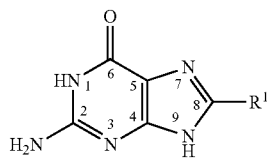

Formula 1

With reference to Formula 1, $R^1$ is selected from amine (—NR'R), hydroxyl (—OH), nitro (—NO$_2$), nitroso (—NO), alkoxy, carbonyl (C=O), halogen, carboxyl, ester, ether, carbonate, amide, alkyl, haloaliphatic, or hydrogen.

Where $R^1$ is amine (—NR'R), each of R and R' independently are hydrogen, aliphatic, aryl, heteroaliphatic, or heteroaryl. In particular embodiments, R and R' are H, and the amine is —NH$_2$.

Where $R^1$ is carbonyl (C=O), the carbon located at the 8 position of Formula 1 forms a double bond with an oxygen atom.

Where $R^1$ is halogen, the halogen is bromo, fluoro, iodo, or chloro.

Where $R^1$ is carboxyl (—C(O)OR), R is hydrogen, aliphatic, aryl, heteroaliphatic, or heteroaryl.

Where $R^1$ is ester (—OC(O)R), R is hydrogen, aliphatic, aryl, heteroaliphatic, or heteroaryl.

Where $R^1$ is ether (—OR), R is aliphatic, aryl, heteroaliphatic, or heteroaryl.

Where $R^1$ is carbonate (—OC(O)OR), R is hydrogen, aliphatic, aryl, heteroaliphatic, or heteroaryl.

Where $R^1$ is amide (—NC(O)R), R is hydrogen, aliphatic, aryl, heteroaliphatic, or heteroaryl.

Where $R^1$ is alkyl (—(CH$_2$)$_n$H).

Where $R^1$ is haloaliphatic (—CH$_2$X, —CHX$_2$, or —CX$_3$), wherein each X independently is halogen (Cl, Br, F, or I).

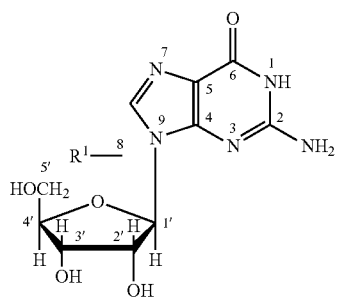

Formula 2

With reference to Formula 2, R is selected from amine (—NR'R), hydroxyl (—OH), nitro (—NO$_2$), nitroso (—NO), alkoxy, carbonyl (C=O), halogen, carboxyl, ester, ether, carbonate, amide, alkyl, haloaliphatic, or hydrogen.

Where $R^1$ is amine (—NR'R), each of R and R' independently are hydrogen, aliphatic, aryl, heteroaliphatic, or heteroaryl. In particular embodiments, R and R' are H, and the amine is —NH$_2$.

Where $R^1$ is carbonyl (C=O), the carbon located at the 8 position of Formula 1 forms a double bond with an oxygen atom.

Where $R^1$ is halogen, the halogen is bromo, fluoro, iodo, or chloro.

Where $R^1$ is carboxyl (—C(O)OR), R is hydrogen, aliphatic, aryl, heteroaliphatic, or heteroaryl.

Where $R^1$ is ester (—OC(O)R), R is hydrogen, aliphatic, aryl, heteroaliphatic, or heteroaryl.

Where $R^1$ is ether (—OR), R is aliphatic, aryl, heteroaliphatic, or heteroaryl.

Where $R^1$ is carbonate (—OC(O)OR), R is hydrogen, aliphatic, aryl, heteroaliphatic, or heteroaryl.

Where $R^1$ is amide (—NC(O)R), R is hydrogen, aliphatic, aryl, heteroaliphatic, or heteroaryl.

Where $R^1$ is alkyl (—(CH$_2$)$_n$H).

Where $R^1$ is haloaliphatic (—CH$_2$X, —CHX$_2$, or —CX$_3$), wherein each X independently is halogen (Cl, Br, F, or I).

Any of these compounds can be included in pharmaceutical compositions and used in the methods disclosed herein.

Specific compounds of use in the methods disclosed herein are shown in Table 2.

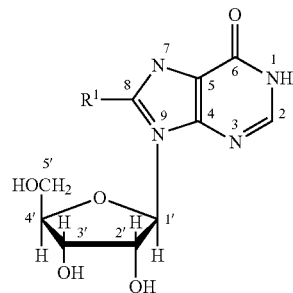

Formula 3

With reference to Formula 3, R is selected from amine (—NR'R), hydroxyl (—OH), nitro (—NO$_2$), nitroso (—NO), alkoxy, carbonyl (C=O), halogen, carboxyl, ester, ether, carbonate, amide, alkyl, haloaliphatic, or hydrogen.

Where $R^1$ is amine (—NR'R), each of R and R' independently are hydrogen, aliphatic, aryl, heteroaliphatic, or heteroaryl. In particular embodiments, R and R' are H, and the amine is —NH$_2$.

Where $R^1$ is carbonyl (C=O), the carbon located at the 8 position of Formula 1 forms a double bond with an oxygen atom.

Where $R^1$ is halogen, the halogen is bromo, fluoro, iodo, or chloro.

Where $R^1$ is carboxyl (—C(O)OR), R is hydrogen, aliphatic, aryl, heteroaliphatic, or heteroaryl.

Where $R^1$ is ester (—OC(O)R), R is hydrogen, aliphatic, aryl, heteroaliphatic, or heteroaryl.

Where $R^1$ is ether (—OR), R is aliphatic, aryl, heteroaliphatic, or heteroaryl.

Where $R^1$ is carbonate (—OC(O)OR), R is hydrogen, aliphatic, aryl, heteroaliphatic, or heteroaryl.

Where $R^1$ is amide (—NC(O)R), R is hydrogen, aliphatic, aryl, heteroaliphatic, or heteroaryl.

Where $R^1$ is alkyl (—(CH$_2$)$_n$H).

Where $R^1$ is haloaliphatic (—CH$_2$X, —CHX$_2$, or —CX$_3$), wherein each X independently is halogen (Cl, Br, F, or I).

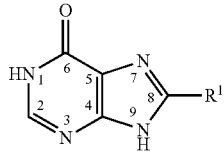

Formula 4

Formula 4, $R^1$ is selected from amine (—NR'R), hydroxyl (—OH), nitro (—NO$_2$), nitroso (—NO), alkoxy, carbonyl (C=O), halogen, carboxyl, ester, ether, carbonate, amide, alkyl, haloaliphatic, or hydrogen.

Where $R^1$ is amine (—NR'R), each of R and R' independently are hydrogen, aliphatic, aryl, heteroaliphatic, or heteroaryl. In particular embodiments, R and R' are H, and the amine is —NH$_2$.

Where $R^1$ is carbonyl (C=O), the carbon located at the 8 position of Formula 1 forms a double bond with an oxygen atom.

Where $R^1$ is halogen, the halogen is bromo, fluoro, iodo, or chloro.

Where $R^1$ is carboxyl (—C(O)OR), R is hydrogen, aliphatic, aryl, heteroaliphatic, or heteroaryl.

Where $R^1$ is ester (—OC(O)R), R is hydrogen, aliphatic, aryl, heteroaliphatic, or heteroaryl.

Where R is ether (—OR), R is aliphatic, aryl, heteroaliphatic, or heteroaryl.

Where $R^1$ is carbonate (—OC(O)OR), R is hydrogen, aliphatic, aryl, heteroaliphatic, or heteroaryl.

Where $R^1$ is amide (—NC(O)R), R is hydrogen, aliphatic, aryl, heteroaliphatic, or heteroaryl.

Where $R^1$ is alkyl (—(CH$_2$)$_n$H).

Where $R^1$ is haloaliphatic (—CH$_2$X, —CHX$_2$, or —CX$_3$), wherein each X independently is halogen (Cl, Br, F, or I).

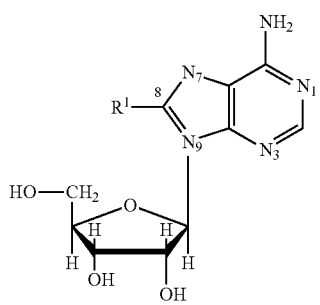

Formula 5

With reference to Formula 5, R is selected from amine (—NR'R), hydroxyl (—OH), nitro (—NO$_2$), nitroso (—NO), alkoxy, carbonyl (C=O), halogen, carboxyl, ester, ether, carbonate, amide, alkyl, haloaliphatic, or hydrogen.

Where $R^1$ is amine (—NR'R), each of R and R' independently are hydrogen, aliphatic, aryl, heteroaliphatic, or heteroaryl. In particular embodiments, R and R' are H, and the amine is —NH$_2$.

Where $R^1$ is carbonyl (C=O), the carbon located at the 8 position of Formula 1 forms a double bond with an oxygen atom.

Where $R^1$ is halogen, the halogen is bromo, fluoro, iodo, or chloro.

Where $R^1$ is carboxyl (—C(O)OR), R is hydrogen, aliphatic, aryl, heteroaliphatic, or heteroaryl.

Where $R^1$ is ester (—OC(O)R), R is hydrogen, aliphatic, aryl, heteroaliphatic, or heteroaryl.

Where $R^1$ is ether (—OR), R is aliphatic, aryl, heteroaliphatic, or heteroaryl.

Where $R^1$ is carbonate (—OC(O)OR), R is hydrogen, aliphatic, aryl, heteroaliphatic, or heteroaryl.

Where $R^1$ is amide (—NC(O)R), R is hydrogen, aliphatic, aryl, heteroaliphatic, or heteroaryl.

Where $R^1$ is alkyl (—(CH$_2$)$_n$H).

Where $R^1$ is haloaliphatic (—CH$_2$X, —CHX$_2$, or —CX$_3$), wherein each X independently is halogen (Cl, Br, F, or I).

TABLE 2

Chemical structures for compounds of use in the methods disclosed herein

| Name | Structure |
|---|---|
| Guanine | 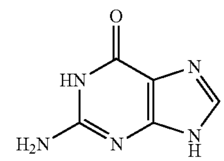 [SMILES: Nc1nc2[nH]cnc2c(=O)[nH]1] |
| Guanosine | 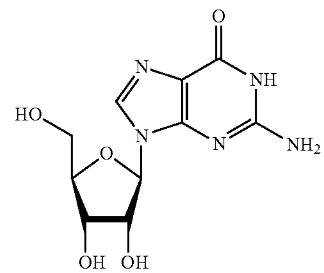 |
| 8-Aminoguanine | 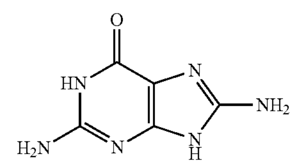 [SMILES: Nc1nc2[nH]c(N)nc2c(=O)[nH]1] |
| 8-Aminoguanosine | 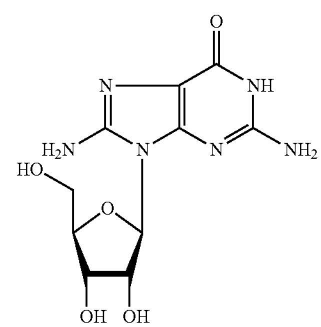 |
| 8-Hydroxyguanine | 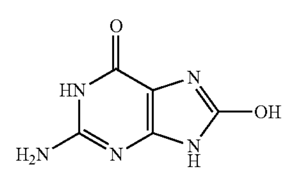 [SMILES: Nc1nc2[nH]c(O)nc2c(=O)[nH]1] |
| 8-Hydroxyguanosine | 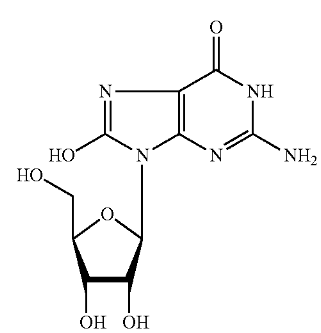 |

TABLE 2-continued

Chemical structures for compounds of use in the methods disclosed herein

| Name | Structure |
|---|---|
| 8-Nitroguanine | 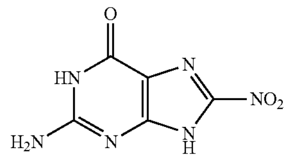 [SMILES: Nc1nc2[nH]c([N+](=O)[O-])nc2c(=O)[nH]1] |
| Amiloride | 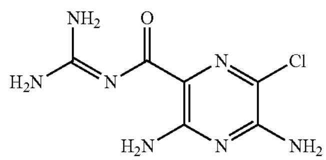 [SMILES: NC(N)=NC(=O)c1nc(Cl)c(N)nc1N] |
| Inosine | 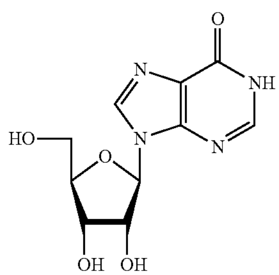 |
| Hypoxanthine | 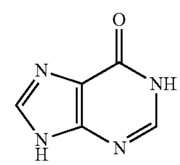 |
| Adenosine | 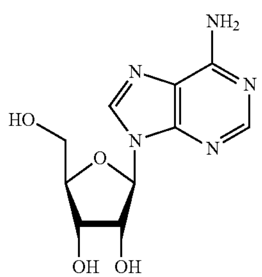 |

Any of these compounds can be included in pharmaceutical compositions and used in the methods disclosed herein.

III. PHARMACEUTICAL COMPOSITIONS AND METHODS OF ADMINISTRATION

Pharmaceutical compositions that include 8-substituted guanine, 8-substituted guanosine, 8-substituted inosine, 8-substituted hypoxanthine, 8-substituted adenosine, inosine, and/or guanosine can be formulated with an appropriate pharmaceutically acceptable carrier. The dosage form of the pharmaceutical composition will be determined by the mode of administration chosen. For instance, in addition to injectable fluids, topical, inhalation, oral, and suppository formulations can be employed. Inhalation preparations can be liquid (e.g., solutions or suspensions) and include mists, sprays, and the like. Oral formulations can be liquid (e.g., syrups, solutions, or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The amount of 8-substituted guanine, 8-substituted guanosine, 8-substituted inosine, 8-substituted hypoxanthine, 8-substituted adenosine, inosine, and/or guanosine administered will be dependent on the subject being treated, the severity of the affliction, and the manner of administration and is best left to the judgment of the prescribing clinician. Within these bounds, the formulation to be administered will contain a quantity of the active component(s) in amounts effective to achieve the desired effect in the subject being treated. A therapeutically effective amount of 8-substituted guanine, 8-substituted guanosine, 8-substituted inosine, 8-substituted hypoxanthine, 8-substituted adenosine, inosine, and/or guanosine can be the amount of 8-substituted guanine, 8-substituted guanosine, 8-substituted inosine, 8-substituted hypoxanthine, 8-substituted adenosine, inosine, and/or guanosine that is necessary to treat or lower the risk of a subject for a particular disease condition (see below).

The pharmaceutical compositions that include 8-substituted guanine, 8-substituted guanosine, 8-substituted inosine, 8-substituted hypoxanthine, 8-substituted adenosine, guanosine, or inosine can be formulated in unit dosage form, suitable for individual administration of precise dosages. In one specific, non-limiting example, a unit dosage can contain about 1-50 µmoles/kg, such as about 1-5, 5-10, 10-20, 20-30, 30-40, or 40-50 µmoles/kg or about 33.5 µmoles/kg of 8-substituted guanine, 8-substituted guanosine, 8-substituted inosine, 8-substituted hypoxanthine, 8-substituted adenosine, guanosine, or inosine. In other examples, a therapeutically effective amount of 8-substituted guanine, 8-substituted guanosine, 8-substituted inosine, 8-substituted hypoxanthine, 8-substituted adenosine, guanosine, or inosine is about 0.1-50 mg/kg, such as about 0.1-1, 1-5, 5-10, 10-20, 20-30, 30-40, or 40-50 mg/kg or about 5, 10, or 30 mg/kg.

Treatment with a therapeutically effective amount can be a single administration or multiple administrations. Treatment can involve daily or multi-daily or less than daily (such as weekly or monthly etc.) doses over a period of a few days to weeks or months, or even years. In a particular non-limiting example, treatment involves once daily dose or twice daily dose. The particular mode/manner of administration and the dosage regimen will be selected by the attending clinician, taking into account the particulars of the case (e.g., the subject, the disease, the disease state/severity involved, the particular treatment, and whether the treatment is prophylactic).

The dosage form of the pharmaceutical composition will be determined by the mode of administration chosen. The pharmaceutically acceptable carriers and excipients useful in this disclosure are conventional (see, e.g., Remington: The Science and Practice of Pharmacy, The University of the Sciences in Philadelphia, Editor, Lippincott, Williams, & Wilkins, Philadelphia, Pa., 21st Edition (2005)). For instance, parenteral formulations usually comprise injectable fluids that are pharmaceutically and physiologically acceptable fluid vehicles, such as water, physiological saline, other balanced salt solutions, aqueous dextrose, glycerol, or the like. In addition to injectable fluids, inhalational and oral formulations can be employed. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example, sodium acetate or sorbitan monolaurate. Excipients that can be included are, for instance, other proteins, such as human serum albumin or plasma preparations. Actual methods of preparing such dosage forms are known, or will be apparent, to those skilled in the art.

The compositions of this disclosure that include 8-substituted guanine, 8-substituted guanosine, 8-substituted inosine, 8-substituted hypoxanthine, 8-substituted adenosine, inosine, and/or guanosine can be administered to humans or other animals by any means, including orally, intravenously, intramuscularly, intraperitoneally (i.p.), intranasally, intradermally, intrathecally, subcutaneously, via inhalation, or via suppository. In one non-limiting example, the composition is administered orally. In further examples, site-specific administration of the composition can be used, for example, by administering 8-substituted guanine, 8-substituted guanosine, 8-substituted inosine, 8-substituted hypoxanthine, 8-substituted adenosine, inosine, and/or guanosine intravenously or subcutaneously.

For oral administration, the pharmaceutical compositions can take the form of, for example, tablets or capsules prepared by conventional means with pharmaceutically acceptable excipients, such as binding agents (for example, pregelatinized maize starch, polyvinylpyrrolidone, or hydroxypropyl methylcellulose); fillers (for example, lactose, microcrystalline cellulose, or calcium hydrogen phosphate); lubricants (for example, magnesium stearate, talc, or silica); disintegrants (for example, potato starch or sodium starch glycolate); or wetting agents (for example, sodium lauryl sulfate). The tablets can be coated by methods well known in the art. Solid dosage forms for oral administration include, but are not limited to, capsules, tablets, pills, powders, and granules. In such solid dosage forms, the active compounds are mixed with at least one pharmaceutically acceptable excipient or carrier such as, but not limited to, sodium citrate or dicalcium phosphate. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations can also contain buffer salts, flavoring, coloring, and sweetening agents as appropriate. For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art. Oral administration includes buccal or "sub-lingual" administration via membranes of the mouth. This can be accomplished using lozenges or a chewable gum.

Pharmaceutical compositions suitable for oral administration can be presented in discrete units each containing a predetermined amount of at least one therapeutic compound useful in the present methods; as a powder or granules; as a solution or a suspension in an aqueous or non-aqueous liquid; or as an oil-in-water or water-in-oil emulsion. As indicated, such compositions can be prepared by any suitable method of pharmacy, which includes the step of bringing into association the active compound(s) and the carrier (which can constitute one or more accessory ingredients). In general, the compositions are prepared by uniformly and intimately admixing the active compound with a liquid or finely divided solid carrier, or both, and then, if necessary, shaping the product.

For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binder, lubricant, inert diluent, and/or surface active/dispersing agent(s). Molded tablets can be made by molding, in a suitable machine, the powdered compound moistened with an inert liquid diluent.

Solid compositions of a similar type can also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) in a certain part of the intestinal tract, optionally, in a delayed manner. Examples of embedding compositions which can be used include polymeric substances and waxes. The active compounds can also be in micro-encapsulated form, if appropriate, with one or more of the above mentioned excipients.

Liquid dosage forms for oral administration include, but are not limited to, pharmaceutically acceptable emulsions, solutions, suspensions, syrups, teas, and elixirs. In addition to the active compounds, the liquid dosage forms can contain inert diluents commonly used in the art such as, for example, water or other solvents, solubilizing agents, and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In some embodiments, suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

A drinkable tea can also be used in the present methods. A drinkable tea may be taken in a liquid form or in a once pulverized or granulated form together with water or hot water. When it is in a powdery or granular form, the drinkable tea may be contained in a cavity of mouth before taking hot water or water like the conventional powdery or granular drinkable tea, or it may be taken after once dissolving in hot water or water. One or more components, such as a sugar, mint, or other flavor, can be added to improve taste and easiness as a drinkable drug. Teas, syrups, and elixirs can be formulated with sweetening agents, for example glycerol, sorbitol, or sucrose. Such compositions can also contain a demulcent, a preservative, and flavoring and coloring agents.

Optionally, the pharmaceutical composition includes a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

In some embodiments, 8-substituted guanine, 8-substituted guanosine, 8-substituted inosine, 8-substituted hypoxanthine, 8-substituted adenosine, inosine, and/or guanosine is included in a controlled release formulation, for example, a microencapsulated formulation. Various types of biodegradable and biocompatible polymers, methods can be used, and methods of encapsulating a variety of synthetic compounds, proteins and nucleic acids, have been well described in the art (see, for example, U.S. Patent Publication Nos. 2007/0148074; 2007/0092575; and 2006/0246139; U.S. Pat. Nos. 4,522,811; 5,753,234; and 7,081,489; PCT Publication No. WO/2006/052285; Benita, Microencapsulation: Methods and Industrial Applications, 2nd ed., CRC Press, 2006).

In other embodiments, 8-substituted guanine, 8-substituted guanosine, 8-substituted inosine, 8-substituted hypoxanthine, 8-substituted adenosine, inosine, and/or guanosine is included in a nanodispersion system. Nanodispersion systems and methods for producing such nanodispersions are well known to one of skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly(ethylene glycol). Exemplary low molecular weight surfactants include sodium dodecyl sulfate, hexadecyl pyridinium chloride, polysorbates, sorbitans, poly(oxyethylene) alkyl ethers, poly(oxyethylene) alkyl esters, and combinations thereof. In one example, the nanodispersion system includes PVP and 8-substituted guanine, 8-substituted guanosine, 8-substituted inosine, 8-substituted hypoxanthine, 8-substituted adenosine, inosine, and/or guanosine (such as 80/20 w/w). In some examples, the nanodispersion is prepared using the solvent evaporation method, see, for example, Kanaze et al., Drug Dev. Indus. Pharm. 36:292-301, 2010; Kanaze et al., J. Appl. Polymer Sci. 102:460-471, 2006.

Many types of release delivery systems are available and known to those of ordinary skill in the art. They include polymer based systems, such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids, including sterols such as cholesterol, cholesterol esters and fatty acids or neutral fats, such as mono-, di-, and tri-glycerides; hydrogel release systems; silastic systems; peptide-based systems; wax coatings; compressed tablets using conventional binders and excipients; partially fused implants; and the like. Specific examples include, but are not limited to: (a) erosional systems in which 8-substituted guanine, 8-substituted guanosine, 8-substituted inosine, 8-substituted hypoxanthine, 8-substituted adenosine, inosine, and/or guanosine is contained in a form within a matrix such as those described in U.S. Pat. Nos. 4,452,775; 4,667, 014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as diabetes. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

IV. METHODS OF TREATMENT

It is disclosed herein that 8-substituted guanine and/or 8-substituted guanosine compounds exert diuretic/natriuretic activity equal or superior to the diuretic amiloride. The 8-substituted guanine and/or 8-substituted guanosine are also potassium-sparing, which can decrease the likelihood of the side effect of hypokalemia, associated with most currently available diuretics. In addition, the 8-substituted guanine and/or 8-substituted guanosine decrease the likelihood of stroke and mean arterial blood pressure (MABP). The 8-substituted guanine and/or 8-substituted guanosine is also shown to increase lifespan in hypertensive subjects. Further, the 8-substituted guanine and/or 8-substituted guanosine also either maintain or increase glucose excretion, which is in contrast to many current diuretics, such as amiloride, thus decreasing the concerns for diabetics in need of a diuretic. Additionally, the 8-substituted guanine and/or 8-substituted guanosine lowers glycated hemoglobin (HbA1C) levels (elevated in diabetes). Other 8-substituted compounds can also be used, including 8-substituted inosine, 8-substituted hypoxanthine, and/or 8-substituted adenosine. In further embodiments, any prodrug (i.e., a medication or compound that, after administration, is metabolized into a pharmacologically active drug) of the compounds could be used (e.g., the prodrugs 8-substituted 3',5'-cGMP; 8-substituted GTP; 8-substituted GDP; and 8-substituted GMP, such as 8-amino-3',5'-cGMP; 8-amino-GTP; 8-amino-GDP; and 8-amino-GMP, can be used therapeutically in the same way as 8-substituted guanosine).

In some non-limiting examples, 8-aminoguanine, 8-aminoguanosine, 8-hydroxyguanine, 8-hydroxyguanosine, and 8-nitroguanine can be used to treat and/or reduce the likelihood of stroke. In other non-limiting examples, 8-aminoguanine, 8-aminoguanosine, 8-hydroxyguanine, 8-hydroxyguanosine, and 8-nitroguanine can be used to treat and/or reduce the likelihood of hypertension, including systemic hypertension and pulmonary hypertension. In still other non-limiting examples, 8-aminoguanine and 8-aminoguanosine can be used to treat and/or reduce the likelihood of diabetes. In other examples, a therapeutically effective amount of a purine nucleoside phosphorylase (PNPase) purine nucleoside substrate may also be provided. In some examples, the substrate can be inosine or guanosine. In still further examples, other 8-substituted compounds can also be used to treat or reduce the likelihood of stroke, to treat and/or reduce the likelihood of hypertension, and/or to treat and/or reduce the likelihood of diabetes, including 8-substituted inosine, 8-substituted hypoxanthine, and/or 8-substituted adenosine.

It is further disclosed herein that PNPase inhibitors (e.g., 8-substituted guanine and/or 8-substituted guanosine) and purine nucleoside substrates (e.g., inosine and/or guanosine) can be used to treat a subject (e.g., a human or mammalian subject) with pulmonary hypertension (PH) and/or reduce the risk of PH in a subject at risk therefor. Other 8-substituted compounds can also be used, including 8-substituted inosine, 8-substituted hypoxanthine, and/or 8-substituted adenosine. In further embodiments, any prodrug (i.e., a medication or compound that, after administration, is metabolized into a pharmacologically active drug) of the compounds could be used (e.g., the prodrugs 8-substituted 3',5'-cGMP; 8-substituted GTP; 8-substituted GDP; and 8-substituted GMP, such as 8-amino-3',5'-cGMP; 8-amino-GTP; 8-amino-GDP; and 8-amino-GMP, can be used therapeutically in the same way as 8-substituted guanosine).

In some non-limiting examples, the subject is exposed to hypoxic conditions (e.g., where the subject lives at high elevations). In additional examples, the subject has a condition associated with PH (e.g., sickle cell disease, human immunodeficiency syndrome, or simian immunodeficiency syndrome). In other examples, the subject has one or more physiological characteristics associated with PH (e.g., body fluids with an increased ratio of guanine to guanosine, body fluids with an increased ratio of inosine to hypoxanthine, elevated right ventricular peak systolic pressure, elevated right ventricular end diastolic pressure, reduced contractility of the right cardiac ventricle, necrotizing arteritis, plexiform lesions in the lung, and/or occlusive lesions in the lung).

It is additionally disclosed herein that PNPase inhibitors (e.g., 8-substituted guanine and/or 8-substituted guanosine) and purine nucleoside substrates (e.g., inosine and/or guanosine) can be used to treat a subject (e.g., a human or mammalian subject) with sickle cell disease (SCD) and/or reduce the sickling of red blood cells (RBCs) in a subject at risk therefor. Other 8-substituted compounds can also be used, including 8-substituted inosine, 8-substituted hypoxanthine, and/or 8-substituted adenosine. In further embodiments, any prodrug (i.e., a medication or compound that, after administration, is metabolized into a pharmacologically active drug) of the compounds could be used (e.g., the prodrugs 8-substituted 3',5'-cGMP; 8-substituted GTP; 8-substituted GDP; and 8-substituted GMP, such as 8-amino-3',5'-cGMP; 8-amino-GTP; 8-amino-GDP; and 8-amino-GMP, can be used therapeutically in the same way as 8-substituted guanosine). In some non-limiting examples, the subject is exposed to hypoxic and/or hypoxemic conditions (e.g., where the subject lives or works at high elevations or is under conditions that limit airflow).

A. 8-Substituted Guanine and/or 8-Substituted Guanosine to Promote Natriuresis.

Methods are disclosed herein for promoting natriuresis, such as the use of 8-substituted guanine and/or 8-substituted guanosine to promote natriuresis. In some non-limiting examples, the methods include administering 8-nitroguanosine, 8-nitroguanine, 8-hydroxyguanosine, 8-hydroxyguanine, 8-aminoguanosine, and/or 8-aminoguanine. Other 8-substituted compounds can be used, including 8-substituted inosine, 8-substituted hypoxanthine, and/or 8-substituted adenosine. Any prodrug (i.e., a medication or compound that, after administration, is metabolized into a pharmacologically active drug) of the compounds could be used (e.g., the prodrugs 8-substituted 3',5'-cGMP; 8-substituted GTP; 8-substituted GDP; and 8-substituted GMP, such as 8-amino-3',5'-cGMP; 8-amino-GTP; 8-amino-GDP; and 8-amino-GMP, can be used therapeutically in the same way as 8-substituted guanosine). In some, embodiments, the method includes selecting a subject in need of a natriuretic. The subject can be a veterinary subject or a human subject.

In these embodiments, the subject may be provided a therapeutically effective amount pharmaceutical composition that includes 8-substituted guanine and/or 8-substituted guanosine, and/or the subject can be provided 8-substituted inosine, 8-substituted hypoxanthine, and/or 8-substituted adenosine. These uses include administration of any one of the pharmaceutical compositions and methods of administration described above for 8-substituted guanine and/or 8-substituted guanosine and/or for 8-substituted inosine, 8-substituted hypoxanthine, and/or 8-substituted adenosine.

Further, additional therapeutic agents, such as agents to promote natriuresis or for the treatment of hypertension (including systemic and/or pulmonary hypertension), diabetes, and/or stroke can be administered and/or included in the disclosed compositions. Thus, the pharmaceutical compositions can include a therapeutically effective amount of another agent, such as a diuretic and/or a purine nucleoside phosphorylase (PNPase) substrate. In other embodiments, the pharmaceutical compositions do not include any other diuretic.

In other embodiments, the disclosed methods include determining whether the treatment is successful by comparing one or more indicator of natriuresis (such as relative sodium levels in urine) in a treated subject to a control, wherein an increase or decrease in the particular indicator relative to the control (as discussed above) indicates effective natriuresis. The control can be any suitable control against which to compare the indicator of natriuresis in a subject. In some embodiments, the control is a sample obtained from a healthy subject. In some embodiments, the control is a historical control or standard reference value or range of values (such as a previously tested control sample). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

B. 8-Substituted Guanine and/or 8-Substituted Guanosine in Elevated Arterial Blood Pressure, Hypertension, and/or Stroke.

In some embodiments, methods are disclosed to treat a subject with elevated arterial blood pressure, hypertension (e.g., systemic and/or pulmonary hypertension), and/or stroke, or to reduce the risk of developing elevated arterial blood pressure, hypertension and/or stroke, such as the use of 8-substituted guanine and/or 8-substituted guanosine to treat a subject with elevated arterial blood pressure, hypertension, and/or stroke or to reduce the risk of developing elevated arterial blood pressure, hypertension and/or stroke in a subject. In some non-limiting examples, the methods include administering 8-nitroguanosine, 8-nitroguanine, 8-hydroxyguanosine, 8-hydroxyguanine, 8-aminoguanosine, and/or 8-aminoguanine. Other 8-substituted compounds can be used, including 8-substituted inosine, 8-substituted hypoxanthine, and/or 8-substituted adenosine. Any prodrug (i.e., a medication or compound that, after administration, is metabolized into a pharmacologically active drug) of the compounds could be used (e.g., the prodrugs 8-substituted 3',5'-cGMP; 8-substituted GTP; 8-substituted GDP; and 8-substituted GMP, such as 8-amino-3',5'-cGMP; 8-amino-GTP; 8-amino-GDP; and 8-amino-GMP, can be used therapeutically in the same way as 8-substituted guanosine).

The methods can include selecting a subject with or at risk of elevated arterial blood pressure, hypertension, and/or stroke, such as a subject with hypertension or prehypertension or a subject with elevated arterial blood pressure as compared with a control subject without elevated blood pressure. In some embodiments, the subject can have a resting systolic arterial blood pressure of at least about 120-130, 130-139, 140-150, 150-159, 160-170, 170-179, or 180 mmHg, or greater than about 120, 140, 160, or 180 mmHg. In some embodiments, the subject can have a resting diastolic arterial blood pressure of at least about 80-89, 90-99, 100-109, or 110 mmHg, or greater than about 80, 90, 100, or 110 mmHg. In other embodiments, the subject can have arterial blood pressure that is elevated compared with a control subject (e.g., a control subject with an arterial systolic blood pressure of about 90-100 or 100-110 mmHg and/or with a diastolic blood pressure of about 60-70 or 70-79 mmHg). In additional embodiments, the elevated arterial blood pressure can be chronic (i.e., hypertension). In still further embodiments, the subject can have one or more risk factors for stroke (e.g., hypertension, diabetes, obesity and/or, high blood cholesterol levels). The subject can be a human or a veterinary subject. Methods are also disclosed for decreasing the likelihood that a subject develops elevated arterial blood pressure, hypertension, and/or has a stroke.

In some non-limiting examples, a subject may be diagnosed with hypertension or prehypertension by methods well known in the art. A subject may be diagnosed with any type of hypertension, such as essential/primary hypertension, secondary hypertension, systemic hypertension, and/or pulmonary hypertension, can be selected for treatment. Essential (or primary) hypertension refers to hypertension for which no specific medical cause can be found to explain a patient's condition. Secondary hypertension indicates that the high blood pressure is a result of (i.e., secondary to) another condition, such as kidney disease or tumors. More than 95% of individual diagnosed with hypertension have essential hypertension. A significant number of essential hypertension is renin-dependent hypertension. Hypertensive individuals whose plasma renin activity (PRA) is not inhibited are considered to have an inappropriate amount of renin and thus to have renin-dependent hypertension. Systemic hypertension refers to hypertension that affects the systemic circulation, which is the part of the cardiovascular system that carries oxygenated blood away from the heart to the body and returns deoxygenated blood back to the heart. Pulmonary hypertension is hypertension that affects the pulmonary circulation, which is the portion of the circulatory system that carries deoxygenated blood away from the right ventricle of the heart to the lungs and returns oxygenated blood to the left atrium and ventricle of the heart.

Hypertension is also a risk factor for stroke, and stroke is typically diagnosed with medical imaging, such as a computerized axial tomography (CT) scan or magnetic resonance imaging (MRI) scan, along with a physical exam.

In other non-limiting examples, the subject may be provided pharmaceutical compositions that include an effective amount of any one of the pharmaceutical compositions disclosed above. In addition any of the methods of administration disclosed above can be utilized.

Further, additional therapeutic agents, such as agents to promote natriuresis and/or diuresis or for the treatment of hypertension and/or stroke can be administered and/or included in the disclosed compositions. Thus, the pharmaceutical compositions can include a therapeutically effective amount of another agent. Non-limiting examples of such agents include antihypertensive agents. Antihypertensive agents include angiotensin-converting enzyme (ACE) inhibitors, angiotensin receptor blockers (ARBs), diuretics, beta blockers, calcium channel blockers, renin inhibitors, alpha blockers, alpha-beta blockers, central-acting agents, vasodilators, and aldosterone antagonists. Additional examples of therapeutic agents that can be administered and/or included in the disclosed compositions to treat or prevent stroke include lipid lowering drugs (e.g., statins), anti-diabetic drugs (e.g., metformin), antiplatelet drugs (e.g., aspirin, clopidogrel, and ticlopidine), and anticoagulants (e.g., warfarin, rivaroxaban, and many others). Any of these agents can also be used in the methods disclosed herein.

Administration of 8-substituted guanine, 8-substituted guanosine, 8-substituted inosine, 8-substituted hypoxanthine, and/or 8-substituted adenosine may also be in combination with lifestyle modifications, such as increased physical activity, low salt diet, limiting the amount of alcohol consumed, maintaining a healthy weight, smoking cessation, stress reduction, and/or reducing salt, sugar, and/or fat intake.

In other embodiments, the disclosed methods include determining whether the treatment is successful by comparing one or more indicator of risk of stroke or hypertension (such as blood pressure levels) in a treated subject to a control, wherein an increase or decrease in the particular indicator relative to the control (as discussed above) indicates effective treatment of hypertension, such as systemic and/or pulmonary hypertension. The control can be any suitable control against which to compare the indicator of hypertension, such as systemic and/or pulmonary hypertension, or stroke risk in a subject. In some embodiments, the control is a sample obtained from a healthy subject (such as a subject without hypertension). In some embodiments, the control is a historical control or standard reference value or range of values (such as a previously tested control sample, such as a group of subjects with hypertension, or group of samples from subjects that do not have hypertension). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

C. 8-Substituted Guanine and/or 8-Substituted Guanosine in Diabetes and/or Prediabetes.

Methods are disclosed herein for treating a subject with type 2 diabetes or at risk of developing diabetes (e.g., a subject with prediabetes), such as the use of 8-substituted guanine and/or 8-substituted guanosine to treat a subject with diabetes or to reduce the risk of developing diabetes in a subject. Other 8-substituted compounds can be used, including 8-substituted inosine, 8-substituted hypoxanthine, and/or 8-substituted adenosine. Any prodrug (i.e., a medication or compound that, after administration, is metabolized into a pharmacologically active drug) of the compounds could be used (e.g., the prodrugs 8-substituted 3',5'-cGMP; 8-substituted GTP; 8-substituted GDP; and 8-substituted GMP, such as 8-amino-3',5'-cGMP; 8-amino-GTP; 8-amino-GDP; and 8-amino-GMP, can be used therapeutically in the same way as 8-substituted guanosine). In some non-limiting examples, the methods include administering 8-nitroguanosine, 8-nitroguanine, 8-hydroxyguanosine, 8-hydroxyguanine, 8-aminoguanosine, and/or 8-aminoguanine. In certain non-limiting examples, the methods include administering 8-aminoguanosine, and/or 8-aminoguanine. In some examples, the methods include selecting a subject with or at risk of diabetes, such as a subject with prediabetes. The subject can be a human subject or a veterinary subject. Methods are also disclosed for decreasing the likelihood that a subject develops diabetes. In some embodiments, the subject has pre-diabetes.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in Standards of Medical Care in Diabetes—2010 (American Diabetes Association, Diabetes Care 33:S11-61, 2010, incorporated herein by reference).

In other examples, the subject may be provided pharmaceutical compositions that include 8-substituted guanine and/or 8-substituted guanosine using any one of the pharmaceutical compositions and methods of administration described above.

Additional therapeutic agents, such as agents to promote diuresis or for the treatment of metabolic disorder, diabetes and/or prediabetes, can be administered and/or included in the disclosed compositions. Anti-diabetic agents are generally categorized into six classes: biguanides; thiazolidinediones; sulfonylureas; inhibitors of carbohydrate absorption; fatty acid oxidase inhibitors and anti-lipolytic drugs; and weight-loss agents. Any of these agents can also be used in the methods disclosed herein. The anti-diabetic agents include those agents disclosed in Diabetes Care, 22(4):623-634, herein incorporated by reference. One class of anti-diabetic agents of use is the sulfonylureas, which are believed to increase secretion of insulin, decrease hepatic glucogenesis, and increase insulin receptor sensitivity. Another class of anti-diabetic agents of use the biguanide antihyperglycemics, which decrease hepatic glucose production and intestinal absorption, and increase peripheral glucose uptake and utilization, without inducing hyperinsulinemia. Additional agents of use include, without limitation, anti-apoptotic substances such as the Nemo-Binding Domain and compounds that induce proliferation such as cyclin dependent kinase (CDK)-6, CDK-4, and Cyclin D1.

Administration of 8-substituted guanine, 8-substituted guanosine, 8-substituted inosine, 8-substituted hypoxanthine, and/or 8-substituted adenosine may also be in combination with lifestyle modifications, such as increased physical activity, low fat diet, low sugar diet, and smoking cessation.

Without being bound by theory, administration of guanine and/or guanosine comprising a substituent at the 8 position treats diabetes or pre-diabetes by increasing glucose tolerance, for example, by decreasing blood glucose levels (such as two-hour plasma glucose in an OGTT or FPG) in a subject. In some examples, the method includes increasing glucose excretion by at least 2-fold (such as at least 5-fold, 10-fold, 12-fold, or more) as compared with a control. In particular examples, a decrease in blood glucose level is determined relative to the starting blood glucose level of the subject (for example, prior to treatment with 8-substituted guanine and/or 8-substituted guanosine). Methods to measure blood glucose levels in a subject (for example, in a blood sample from a subject) are routine.

In other embodiments, the disclosed methods include comparing one or more indicator of diabetes (such as HbA1c levels) to a control, wherein an increase or decrease in the particular indicator relative to the control (as discussed above) indicates effective treatment of diabetes. The control can be any suitable control against which to compare the indicator of diabetes in a subject. In some embodiments, the control is a sample obtained from a healthy subject (such as a subject without diabetes). In some embodiments, the control is a historical control or standard reference value or range of values (such as a previously tested control sample, such as a group of subjects with diabetes, or group of samples from subjects that do not have diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

D. 8-Substituted Guanine and/or 8-Substituted Guanosine in Other Diseases.

In additional examples, 8-substituted guanine, 8-substituted guanosine, 8-substituted inosine, 8-substituted hypoxanthine, and/or 8-substituted adenosine may be used to treat heart, kidney, lung, brain, and/or liver disease. In these embodiments, the subject with heart, kidney, lung, brain, and/or liver disease can be selected for treatment. The subject can be a human subject or a veterinary subject. Subjects may be selected using routine clinical methods for detecting diseases of the heart, kidney, lung, brain, or liver such as patient history, tests for assessment of organ function, imaging modalities to examine the macroscopic structure of the affected organ, histological methods to assess the microscopic structure of the affected organ, and blood and urine biomarkers that are released by the injured or diseased organ. In other examples, the subject may be provided pharmaceutical compositions that include 8-substituted guanine and/or guanosine through any one of the pharmaceutical compositions and methods of administration described above for 8-substituted guanine and/or 8-substituted guanosine. These compositions can be used to treat and/or decrease the likelihood of diseases or pathological conditions of the heart (e.g., coronary artery disease, enlarged heart, heart attack, irregular heart rhythm, atrial fibrillation, heart valve disease, sudden cardiac death, congenital heart disease, any type of cardiomyopathy, pericarditis, pericardial effusion, marfan syndrome, and/or heart murmurs), kidney (e.g., acute prerenal kidney failure, acute intrinsic kidney failure, chronic prerenal kidney failure, chronic intrinsic kidney failure, and/or chronic post renal failure), lung (e.g., obstructive or restrictive lung diseases as well as pulmonary hypertension, diaphragm disorders, chest wall restriction, and/or recovery from lung surgery), brain (brain injuries, brain tumors, and/or neurodegenerative diseases), or liver (e.g., alcohol-related liver disease, non-alcoholic fatty liver disease, hepatitis, haemochromatosis, and/or primary biliary cirrhosis).

E. PNPase Substrates and Inhibitors in Pulmonary Hypertension.

Disclosed herein are methods of treating a subject (e.g., a human or veterinary subject) with pulmonary hypertension (PH) or reducing the risk of PH in a subject, such as using a purine nucleoside phosphorylase (PNPase) inhibitor and/or a PNPase purine nucleoside substrate. The methods can include administering to the subject a therapeutically effective amount of a PNPase inhibitor and/or PNPase purine nucleoside substrate, thereby treating the PH or reducing the risk of PH. In some non-limiting examples, both PNPase inhibitor(s) and PNPase purine nucleoside substrate(s) and/ or substrate precursor are administered.

In some examples, the PNPase inhibitor can be 8-substituted guanine and/or 8-substituted guanosine. In other examples, the PNPase inhibitor is an 8-substituted inosine and/or 8-substituted hypoxanthine. In still further examples, an 8-substituted precursor to the PNPase inhibitor can be used, such as 8-substituted adenosine. In additional examples, a prodrug of the 8-substituted PNPase inhibitor can be used (e.g., the prodrugs 8-substituted 3',5'-cyclic guanosine monophosphate (cGMP); 8-substituted guanosine-5'-triphosphate (GTP); 8-substituted guanosine-5'-triphosphate (GDP); and 8-substituted GMP, such as 8-amino-3',5'-cGMP; 8-amino-GTP; 8-amino-GDP; and 8-amino-GMP, can be used therapeutically in the same way as 8-substituted guanosine). In some non-limiting examples, the substituent (e.g., the substituent on the guanine, guanosine, inosine, and/or hypoxanthine can be amine, hydroxyl, nitro, nitroso, alkoxy, carbonyl, halogen, carboxyl, ester, carbonate, amide, or haloaliphatic. In other non-limiting examples, the 8-substituted guanine can include 8-aminoguanine and/or the 8-substituted guanosine can include 8-aminoguanosine. In additional examples, a PNPase purine nucleoside substrate is administered. In some non-limiting examples, the substrate can be inosine or guanosine.

The methods disclosed herein include selecting a subject with PH or at risk of developing PH. The subject can have any type of PH, such as Group 1, 2, 3, or 4 PH. The subject can have PH that is any level of severity, such as mild, moderate, or severe PH (e.g., Class I, II, III, or IV, as measured using the World Health Organization classification system, see Patent Pub. No. US20160346280 A1, incorporated herein by reference). In some examples, the subject can have limitations of physical activity, dyspnea, fatigue, chest pain, and/or near syncope (see id., incorporated herein by reference).

The methods can include selecting a subject with PH or at risk of developing PH that is exposed to conditions associated with PH. In certain examples, the subject can be exposed to hypoxic conditions. For example, the subject can live at or have an occupation at a high elevation. In some examples where the subject lives or works at a high elevation, the subject can live or work at altitudes greater than 2,100 meters above sea level. In some examples, the elevation can be 2,100-2,500, 2,500-3,000, 3,000-4,000, 4,000-5,000, 6,000-7,000, or 7,000-8,000 meters above sea level.

In other examples, the methods can include selecting a subject with PH or at risk of developing PH that has body fluid levels associated with PH. In some non-limiting examples, the subject can have body fluids with an increased ratio of guanine to guanosine, such as at least about a 5-10%, 10-20%, 20-30%, 30-40%, 40-50%, 50-60%, 60-70%, 80-90%, or 90-100% or at least about a 1- to 2-fold, 2- to 3-fold, 3- to 4-fold, 4- to 5-fold, 5- to 6-fold, 6- to 7-fold, 7- to 8-fold, 8- to 9-fold, 9- to 10-fold increase in the ratio guanine to guanosine compared with a control subject without PH or that is not at risk of PH (e.g., a control subject with about a 2:1, 3:1, 4:1, 5:1, or 6:1 ratio of guanine to guanosine). In other examples, the subject can have body fluids with an increased ratio of hypoxanthine to inosine such as at least about a 5-10%, 10-20%, 20-30%, 30-40%, 40-50%, 50-60%, 60-70%, 80-90%, or 90-100% or at least about a 1- to 2-fold, 2- to 3-fold, 3- to 4-fold, 4- to 5-fold, 5- to 6-fold, 6- to 7-fold, 7- to 8-fold, 8- to 9-fold, 9- to 10-fold increase in the ratio hypoxanthine to inosine compared with a control subject without PH or that is not at risk of PH (e.g., a control subject with about a 3:1, 4:1, 5:1, 6:1, 7:1, 8:1, 9:1, 10:1, 11:1, or 12:1 ratio of hypoxanthine to inosine). In still other examples, the subject can have body fluids with reduced levels of endogenous PNPase inhibitors, such as 8-substituted guanosine and/or 8-substituted guanine (e.g., 8-aminoguanosine and/or 8-aminoguanine) compared with a control subject without PH or that is not at risk of PH. For example, the subject can have body fluids with at least about 1- to 2-fold, 2- to 3-fold, 3- to 4-fold, 4- to 5-fold, 5- to 6-fold, 6- to 7-fold, 7- to 8-fold, 8- to 9-fold, 9- to 10-fold or about 2-fold, 3-fold, or 4-fold less 8-aminoguanosine and/or 8-aminoguanine compared with a control subject without PH or that is not at risk of PH (e.g., a control subject with about 8-9, 9-10, 10-11, 11-12, 12-13, 13-14, 14-15, 15-16, 16-17, 17-18, 18-19, 19-20, 21-22, or 22-23 ng/mL 8-aminoguanosine and/or 8-aminoguanine or about 15, 16, 17, 18, 19, or 20 ng/mL 8-aminoguanosine and/or about 8, 9, 10, 11, 12, or 13 ng/mL 8-aminoguanine).

In other examples, the methods can include selecting a subject with PH or at risk of developing PH that has physiological characteristics associated with PH. Methods for assessing physiology characteristics are known to those skilled in the art (see Bellofiore et al., Ann Biomed Eng, 41(7):1384-1398, 2013, incorporated herein by reference). In some examples, the subject can have elevated right ventricular peak systolic pressure (RVPSP), such as at least about a 2- to 2.5-fold, 2.5- to 3-fold, 3- to 3.5-fold, 3.5- to 4-fold, 4- to 4.5-fold, or 4.5- to 5-fold elevation or about a 3-fold, 3.5-fold, or 4-fold elevation in RVPSP compared with a control subject without PH or that is not at risk of PH (e.g., a control subject with an RVPSP of about 11, 12, 13, 14, 15, 16, 17, or 18 mmHg). Methods for measuring RVPSP are known for those skilled in the art (see Barst et al., JACC 43(12):Suppl S, pages 40S-47S, incorporated herein by reference). In additional examples, the subject can have elevated right ventricular end diastolic pressure (RV EDP), such as at least about an RV EDP elevated by 2-3, 3-4, 4-5, 5-6, 6-7, 7-8, 8-9, or 9-10 mmHg or by about 3, 4, or 5 mmHg compared with a control subject without PH or that is not at risk of PH (e.g., a control subject with an RV EDP of about 0 mmHg or a negative mmHg). Methods for measuring EDP are known for those skilled in the art (see id., incorporated herein by reference). In some other examples, the subject can have reduced contractility of the right cardiac ventricle, such as a contractility index reduced by at least about 5-10%, 10-20%, 20-30%, 30-40%, 40-50%, or 50-60% or by about 25%, 30%, or 35% compared with a control subject without PH or that is not at risk of PH (e.g., a control subject with a contractility index of about 140, 150, 160, or 170). Methods for measuring contractility index are known for those skilled in the art (see Bombardini, Cardiovascular Ultrasound, 3:27, 22 page, 2005, incorporated herein by reference). In other non-limiting examples, the subject can have occlusive, partially occlusive, and/or plexiform lesions and/or necrotizing arteritis. Methods for observing occlusive, partially occlusive, and/or plexiform lesions and/or necrotizing arteritis are known for those skilled in the art (see Pietra et al., JACC 43(12):Suppl S, pages 25S-32S, 2004, incorporated herein by reference).

In some examples, the methods herein can include selecting a subject with PH or at risk of developing PH that has a disease associated with PH. In some non-limiting examples, the subject can be infected with a human immunodeficiency virus (HIV) or a simian immunodeficiency virus (SIV) or can have sickle cell disease (SCD). Methods for diagnosing HIV, SIV, and SCD are known to those skilled in the art (see Zulfiqar et al., Frontiers in Public Health, 5(32), 16 pages, 2017; Yee et al., J Med Primatol. 2016 April; 45(2): 55-78, 2017; Chakravorty et al., Arch Dis Child, 100:48-53, 2015, all of which are incorporated herein by reference). In other examples, the subject can have mixed connective-tissue disease, congenital heart disease (CHD), chronic obstructive pulmonary disease (COPD), hereditary hemorrhagic telangiectasia (HHT), recurrent pulmonary embolism, sleep apnea, liver disease, or lupus. In certain other examples, the subject can have an infection associated with PH. In some non-limiting examples, the subject can have Schistosomiasis. In still further examples, the subject can use a drug or toxin associated with PH. In some non-limiting examples, the subject can use fenfluramine, dexfenfluramine, and methamphetamines.

In some non-limiting examples, the subject has PH or is at risk of developing PH and has SCD. In some examples, the subject can have increased sickling of blood cells. Methods for measuring blood cell sickling are known by those skilled in the art (see Patent Pub. No. US20170219559, incorporated herein by reference). In other examples, the subject can have an increase in the ratio guanine to guanosine compared with a control subject without PH or that is not at risk of PH, such as an increase of at least about 5%, 10%, 20%, 30%, 40%, or 50% in the ratio guanine to guanosine. In certain examples, the subject can have an increase in the ratio hypoxanthine to inosine compared with a control subject without PH or that is not at risk of PH, such as an increase of at least about 40%, 50%, 60%, 70%, or 80% increase in the ratio hypoxanthine to inosine. In additional examples, the subject can have lower levels of the endogenous PNPase inhibitors 8-aminoguanosine and/or 8-aminoguanine, such as about 1-2, 2-3, 3-4, 4-5, 5-6, or 6-7 ng/mL of 8-aminoguanosine and/or 8-aminoguanine.

In other non-limiting examples, the subject has PH or is at risk of developing PH and has HIV or SIV. In other examples, the subject can have an increase in the ratio guanine to guanosine compared with a control subject without PH or that is not at risk of PH, such as an increase of at least about 3-fold, 4-fold, 5-fold, 6-fold, 7-fold, 8-fold, 9-fold, or 10-fold in the ratio guanine to guanosine. In certain examples, the subject can have an increase in the ratio hypoxanthine to inosine compared with a control subject without PH or that is not at risk of PH, such as an increase of at least about 3-fold, 4-fold, 5-fold, 6-fold, 7-fold, 8-fold, 9-fold, or 10-fold increase in the ratio hypoxanthine to inosine.

The methods disclosed herein can treat or attenuate PH or can reduce the risk of PH in a subject with PH or at risk of PH, respectively. For example, the methods can be used to reduce or prevent pathophysiological characteristics associated with PH or a risk of PH in a subject that has received treatment using the methods described herein. Pathological characteristics of subjects with PH or at risk of PH and methods of measuring such pathological characteristics are known by those skilled in the art (see Patent Pub. Nos. US20160346280 and US20170088897; Barst et al., JACC 43(12):Suppl S, pages 40S-47S, all of which are incorporated herein by reference). In some examples, the methods can be used to decrease elevated right ventricular peak systolic pressure (RVPSP) in a subject, such as at least by about a 5-10, 10-15, 15-20, 20-25, 25-30, 30-35, 04 35-40 mmHg or about 15, 20, or 25 mmHg in RVPSP compared with a subject with elevated RVPSP that does not receive treatment using the methods disclosed herein (e.g., a subject with an RVPSP of about 65, 70, 75, 80, 85, 90, or 95 mmHg). In additional examples, the methods can be used to decrease elevated right ventricular end diastolic pressure (RV EDP) in a subject, such as at least by about 1, 2, 3, 4, 5, or 6 mmHg or by about 3, 4, or 5 mmHg compared to a subject with elevated RV EDP that does not receive treatment using the methods disclosed herein (e.g., a subject with an RV EDP of about 1, 2, 3, 4, 5, or 6 mmHg, incorporated herein by reference). In some other examples, the methods can be used to increase contractility of the right cardiac ventricle, such as a contractility index increased by at least about 5-10%, 10-20%, 20-30%, 30-40%, 40-50%, 50-60%, or 60-70% or by about 40%, 50%, or 60% compared to a subject with PH or is at risk of PH that does not receive treatment using the methods disclosed herein (e.g., a subject with a contractility index of about 95, 100, 105, or 110). In other non-limiting examples, the methods can be used to decrease or decreased the risk of developing occlusive, partially occlusive, and/or plexiform lesions and/or necrotizing arteritis. In further examples, the methods can be used to decrease or decreased the risk of developing In some non-limiting examples, where the subject has PH or is at risk of PH and has SCD, the methods can be used to reduce the sickling of red blood cells. For example, the methods can be used to reduce red blood cell sickling in the subject at least by about 20-25%, 25-30%, 30-35%, 35-40%, 40-45%, 45-50%, 50-60%, or 60-70% or about 30%, 35%, or 45%. In some non-limiting examples where a PNPase inhibitor (e.g., 8-aminoguanosine and/or 8-aminoguanine) is used in the methods, the methods can be used to reduce sickling at least by about 30%, 35%, or 40%. In other non-limiting examples where a PNPase purine nucleoside substrate (e.g., guanosine and/or inosine) is used in the methods, the methods can be used to reduce sickling at least by about 25%, 30%, or 35%. In still further examples where a PNPase purine nucleoside substrate (e.g., guanosine and/or inosine) is used in combination with a PNPase inhibitor (e.g., 8-aminoguanosine and/or 8-aminoguanine) in the methods, the methods can be used to reduce sickling at least by about 40%, 45%, and 50%.

Additional therapies, such as therapies to treat PH, HIV, SIV, and/or SCD, can be administered and/or included with the disclosed compositions. Therapies to treat PH are known by those skilled in the art (see Galiè et al, European Heart Journal, 37:67-119, 2016, incorporated herein by reference). In some examples, administration of additional therapies in combination with those in the disclosed compositions include general measures (e.g., physical activity and supervised rehabilitation, pregnancy, birth control and post-menopausal hormonal therapy, elective surgery, infection prevention, psychosocial support, adherence to treatments, genetic counseling, and/or travel), supportive therapy (oral anticoagulants, diuretics, $O_2$, and/or digoxin), calcium channel blocker therapy, iron substitution, endothelin receptor antagonists, phosphodiesterase type 5 inhibitors, guanylate cyclase stimulators, prostacyclin analogs, prostacyclin receptor agonists, rho kinase inhibitors, vascular endothelial growth factor receptor inhibitors, angiopoietin-1 inhibitors, elastase inhibitors, balloon atrial septostomy, transplantation or any combination thereof (see id., incorporated herein by reference).

Additional therapies to treat HIV and SIV are also known by those skilled in the art (see Zulfiqar et al., Frontiers in Public Health, 5(32), 16 pages, 2017; Daar, F1000Research, 6(F1000 Faculty Rev):759, 7 pages, 2017, both of which are incorporated herein by reference). In some examples administration of additional therapies to treat HIV and SIV in combination with those in the disclosed compositions include antiretroviral drugs (e.g., nucleoside or nucleoside reverse transcriptase inhibitors (NRTIs), non-nucleoside reverse transcriptase inhibitors (NNRTIs), protease inhibitors (PIs), entry inhibitors (co-receptor antagonists and fusion inhibitors), and/or integrase inhibitors (INSTIs)), bone marrow transplants, and/or gene editing (e.g., gene editing using zinc finger nucleases, transcription activator-like effector nucleases, and/or CRISPR/CAS9 (clustered regularly interspersed palindromic repeats-CRISPR associated 9)) (see Zulfiqar et al., Frontiers in Public Health, 5(32), 16 pages, 2017, incorporated herein by reference).

Additional therapies to treat SCD are further known by those skilled in the art (see Chaturvedi et al., American Journal of Hematology, 91:1, 5-14, 2016; Telen, F1000Research, 4(F1000 Faculty Rev):1050 L, 12 pages, 2015, both of which are incorporated herein by reference). In some examples, administration of additional therapies to treat SCD in combination with those in the disclosed compositions include hydroxyurea therapy, stroke prevention in sickle cell anemia (SCA), penicillin prophylaxis, hematopoietic stem cell transplantation, gene transfer or correction (gene editing), nutritional supplements, anti-inflammatory therapy, anti-adhesive therapy, anti-sickling therapy, altered hemoglobin expression therapy, anti-coagulant and anti-platelet therapy, NO therapy, ICA-17043 (senicapoc), losartan, 6R-BH4 (sapropterin dihydrochloride), magnesium sulfate, varespladib (A-001), atorvastatin, simvastatin, bosentan, and/or clotrimazole (see Chaturvedi et al., American Journal of Hematology, 91:1, 5-14, 2016; Telen, F1000Research, 4(F1000 Faculty Rev):1050 L, 12 pages, 2015, both of which are incorporated herein by reference).

F. Purine Nucleoside Phosphorylase (PNPase) Inhibitors and/or PNPase Purine Nucleoside Substrates to Treat Sickle Cell Disease.

Disclosed herein are methods of treating a subject with sickle cell disease (SCD), such as using PNPase inhibitors and/or PNPase purine nucleoside substrates. The methods can include administering to the subject a therapeutically effective amount of a PNPase inhibitor and/or PNPase purine nucleoside substrate, thereby treating the SCD and/or reducing the sickling of RBCs. In some non-limiting examples, both PNPase inhibitor(s) and purine nucleoside substrate(s) are administered.

Sickle cell disease can take multiple forms, including hemoglobin SS disease (HbSS), hemoglobin SC disease (HbSC), hemoglobin S$\beta^+$ thalassemia (HbS$\beta^+$; also known as HbSB+ and Hb$\beta^S\beta^+$), hemoglobin S$\beta^\circ$ thalassemia (HbS$\beta^\circ$; also known as HbSB0 and Hb$\beta^S\beta^\circ$), hemoglobin SD (HbSD), hemoglobin SE (HbSE), hemoglobin SO (HbSO), and sickle cell trait (SCT; also known as HbAS). A subject with any of these forms of sickle cells disease can be treated using the methods disclosed herein. In some embodiments, the disclosed methods reduce the sickling of RBCs in these subjects.

Sickle cell disease can be diagnosed with a simple genetic or blood test (e.g., blood counts can reveal an abnormal Hb level, blood films may show RBCs that appear as irregularly contracted cells, and/or sickle solubility tests look for the presence of HbS). Hb electrophoresis confirms the diagnosis of sickle cell disease. It measures the different types of hemoglobin in the blood. It most often is found at birth during routine newborn screening tests at the hospital. In addition, SCD can be diagnosed before birth. Clinical features of SCD include infants with spontaneous painful swelling of the hands and feet, recurrent episodes of severe pain with no other identified etiology, unexplained anemia not related to iron deficiency, pallor, jaundice, pneumococcal sepsis or meningitis, severe anemia with splenic enlargement, and stroke, especially in a child. Laboratory features include normocytic anemia; sickle cells, nucleated red blood cells, target cells, and other abnormal red blood cells on peripheral blood smear; Howell-Jolly bodies indicate hyposplenism; presence of hemoglobin S (HbS) on a hemoglobin assay (e.g., high-performance liquid chromatography [HPLC], isoelectric focusing, cellulose acetate electrophoresis, citrate agar electrophoresis) with an absence or diminished amount of HbA. Clinical manifestations include vaso-occlusive events (such as determined by a higher white blood cell count, lower HbF levels, older age, co-existing alpha-thalassemia trait, iron overload, vessel flow resistance related to deoxygenation), chronic hemolysis (such as determined by elevated plasma levels of lactate dehydrogenase, and high reticulocyte count). A subject with SCD, that is either an adult, child or infant, can be treated using the methods disclosed herein.

Sickle cell disease commonly causes chronic anemia (i.e., on-going, low red blood cell counts), a reduced ability to fight off infections, and damage to the organs (such as the lungs and kidneys), in addition to acute and chronic pain. Complications can occur as a result of extreme conditions, such as being at high altitude, being dehydrated (i.e., having too little water in the body), or having too little oxygen in the body after intense exercise. In some embodiments, the subject has anemia.

The methods include administering to the subject a therapeutically effective amount of a PNPase inhibitor and/or PNPase purine nucleoside substrate, thereby treating the SCD and/or reducing the sickling of RBCs. In some non-limiting examples, both PNPase inhibitor(s) and purine nucleoside substrate(s) are administered. In some examples, the PNPase inhibitor can be 8-substituted guanine and/or 8-substituted guanosine. Other 8-substituted PNPase inhibitor compounds can be used, including 8-substituted inosine, 8-substituted hypoxanthine, and/or 8-substituted adenosine. Any prodrug (i.e., a medication or compound that, after administration, is metabolized into a pharmacologically active drug) of the compounds could be used (e.g., the prodrugs 8-substituted 3',5'-cGMP; 8-substituted GTP; 8-substituted GDP; and 8-substituted GMP, such as 8-amino-3',5'-cGMP; 8-amino-GTP; 8-amino-GDP; and 8-amino-GMP, can be used therapeutically in the same way as 8-substituted guanosine). In certain examples, the substituent on the compound (e.g., the substituent at the 8 position of the guanine, guanosine, inosine, hypoxanthine, and/or, adenosine) can be amine, hydroxyl, nitro, nitroso, alkoxy, carbonyl, halogen, carboxyl, ester, carbonate, amide, or haloaliphatic. In some non-limiting examples, the 8-substituted guanine can include 8-aminoguanine. In other non-limiting examples, the 8-substituted guanosine can include 8-aminoguanine. In additional examples, a PNPase purine nucleoside substrate is administered. In some non-limiting examples, the substrate can be inosine or guanosine.

In some examples, the methods can include selecting a subject with SCD. The subject can have any type of SCD, including hemoglobin SS disease (HbSS), hemoglobin SC disease (HbSC), hemoglobin S$\beta^+$ thalassemia (HbS$\beta^+$; also known as HbSB+ and Hb$\beta^S\beta^+$), hemoglobin S$\beta^0$ thalassemia (HbS$\beta^0$; also known as HbSB0 and Hb$\beta^S\beta^0$), hemoglobin SD (HbSD), hemoglobin SE (HbSE), hemoglobin SO (HbSO), and sickle cell trait (SCT; also known as HbAS). Methods of detecting SCD are known in the art (see Bender, GeneReviews: Sickle Cell Disease, 2017, https://www.ncbi.nlm.nih.gov/books/NBK1377/; Kotila, Annals of Ibadan Postgraduate Medicine. 8(1): 25-29, 2010; Figueiredo, Rev Bras Hematol Hemoter, 37(3):150-152, 2015; Chaturvedi et al., American Journal of Hematology, 91:1, 5-14, 2016; Telen, F1000Research, 4(F1000 Faculty Rev):1050 L, 12 pages, 2015, all of which incorporated herein by reference).

In some embodiments, a subject can be selected based on a genetic test and/or a blood test, such as a hemoglobin assay (e.g., high-performance liquid chromatography [HPLC], isoelectric focusing, cellulose acetate electrophoresis, and/or citrate agar electrophoresis). In some examples, the subject is selected using a genetic test, such as genetic test that shows the subject has one or two HbS alleles (i.e., a subject with HbS or HbSS, respectively), an HbS allele and an Hb$\beta$ thalassemia variant (i.e., a subject with Hb$\beta^S\beta^+$ or Hb$\beta^S\beta^0$), an HbS allele and an HbC variant (i.e., a subject with HbS/C), an HbS allele and an HbD variant (i.e., a subject with HbS/D), an HbS allele and an HbO variant (i.e., a subject with HbS/O), or an HbS allele and an HbE variant (i.e., a subject with HbS/E).

In other examples, the subject is selected using a blood test, such as a blood test that shows the subject has the presence of hemoglobin S (HbS), for example a subject that has about 10-20%, 20-30%, 30-40%, and/or 40-50% or about 35-40% HbS (i.e., a subject with HbS) and/or a subject that has about 60-70%, 70-80%, 80-90%, and or 90-100% or about 80-90% HbS (i.e., a subject that has HbSS). In additional examples, a subject is selected using a blood test, such as a blood test that shows the subject has decreased mean corpuscular volume (i.e., the average volume of RBCs) compared with a control subject, such as a subject with at least as low as about 50-60, 60-70, or 70-80 fL or about less than 81 fL (i.e., a subject with Hb$\beta^S\beta^+$ or Hb$\beta^S\beta^0$) compared with a control subject with at least about 81 fL. In other examples, a subject is selected using a blood test, such as a blood test that shows the subject has increased HbA$_2$ levels compared with a control subject, such as a subject with at least about 3.6-4%, 4-5%, 5-6%, and/or 6-6.5% HbA$_2$ or about 4-6% HbA$_2$ (i.e., a subject with Hb$\beta^S\beta^+$ or Hb$\beta^S\beta^0$) compared with a control subject with about less than 3.6%, 3%, and/or 2.5% HbA$_2$ or about 2.5% HbA$_2$. In still further examples, a subject is selected using a blood test, such as a blood test that shows that a subject with an HbS allele also has the presence of an HbC, HbO, and/or HbE variant, such as detected using an electrophoretic or HPLC assay.

In other embodiments, a subject can be selected based on clinical features, such as subjects with spontaneous painful swelling of the hands and feet, recurrent episodes of severe pain with no other identified etiology, unexplained anemia not related to iron deficiency, pallor, jaundice, pneumococcal sepsis or meningitis, severe anemia with splenic enlargement, and/or stroke. In still further embodiments, a subject can be selected based on additional laboratory features, such as a subject with normocytic anemia; sickle cells, nucleated red blood cells (RBCs), target cells, and/or other abnormal RBCs on peripheral blood smear; and/or hyposplenism (e.g., as indicated by Howell-Jolly bodies). In additional embodiments, a subject can be selected based on clinical manifestations, such as vaso-occlusive events (e.g., as determined by a higher white blood cell count, lower HbF levels, older age, co-existing alpha-thalassemia trait, iron overload, and/or vessel flow resistance related to deoxygenation) and/or chronic hemolysis (such as determined by elevated plasma levels of lactate dehydrogenase and/or high reticulocyte count).

In further embodiments, the methods can include selecting a subject with SCD and at risk for RBC sickling, such as a subject under conditions that decrease oxygen availability and/or that decrease oxygen tension (e.g., hypoxic and/or hypoxemic conditions, respectively). In certain examples, the subject can have a lower oxygen tension than a control subject that is not under hypoxemic conditions. For example, a subject can have an oxygen tension of at least less than 20, 30, 40, 50, 60, 70, or 80 mmHg or about 20-30, 30-40, 40-50, 50-60, 60-70, or 70-80 mmHg compared with a control subject that that is not under hypoxemic conditions (i.e., a control subject with at least about 80-90 or 90-100 mmHg). In some examples, a subject is under conditions that limit airflow, such as suffocation (e.g., as associated with sleep apnea or sleeping conditions that interfere with breathing, such as in infants, structural deformities of the chest (e.g., scoliosis and kyphosis), muscle weakness that limits diaphragm function (such as associated with a motor neuron disease or chronic obstructive pulmonary disease, COPD). In other examples, the subject is at a high altitude (e.g., in areas of high altitude or when flying); for example, the subject can live at or have an occupation at a high elevation. In some examples where the subject lives or works at a high elevation, the subject can live or work at altitudes greater than 2,100 meters above sea level. In some examples, the elevation can be 2,100-2,500, 2,500-3,000, 3,000-4,000, 4,000-5,000, 6,000-7,000, or 7,000-8,000 meters above sea level. In still further examples, the subject can be under additional hypoxic and/or hypoxemic conditions, such as diving, switching from inhaled anesthesia to atmospheric air (i.e., diffusion hypoxia), or excessive exercise (i.e., exercise-induced arterial hypoxemia). The disclosed methods can improve one or more of these parameters.

In additional embodiments, the methods can include administering additional therapies to treat SCD. Additional therapies to treat SCD are further known by those skilled in the art (see Bender, Gene Reviews: Sickle Cell Disease, 2017, https://www.ncbi.nlm.nih.gov/books/NBK1377/; Kotila, Annals of Ibadan Postgraduate Medicine. 8(1): 25-29, 2010; Figueiredo, Rev Bras Hematol Hemoter, 37(3): 150-152, 2015; Chaturvedi et al., American Journal of Hematology, 91:1, 5-14, 2016; Telen, F1000Research, 4(F1000 Faculty Rev):1050 L, 12 pages, 2015, all of which incorporated herein by reference). Treatment options differ for SCD, depending on the symptoms, and include rehydration with intravenous fluids, treating underlying or associated infections, blood transfusions, supplemental oxygen provided through a mask, pain medication, hydroxyurea (e.g., Droxia® and Hydrea), and immunizations to prevent infections. SCD can be cured using a bone marrow or stem cell transplant. Generally, bone marrow or stem cell transplants are typically only used for severe SCD in children with minimal organ damage. Patients can also take measures to help their SCD symptoms, such as using heating pads for pain relief; consuming vitamin supplements; consuming an adequate amount of nutrients and water; and regular exercise. Any of these treatment options can be combined with the presently disclosed methods.

In some examples, administration of additional therapies to treat SCD in combination with those in the disclosed compositions include rehydration with intravenous fluids, hydroxyurea therapy (e.g., DROXIA® and/or HYDREA®), treating underlying or associated infections (e.g., using antibiotics, such as with penicillin prophylaxis therapy), gene transfer or correction (gene editing), nutritional supplements (e.g., folic acid, L-glutamine, niacin, alpha-lipoic acid, acetyle-L-carnatine, arginine, and/or vitamin B12 supplements), immunizations to prevent infection (e.g., pneumococcus, influenza, and/or meningococcus), pain medication and/or management (e.g., administering non-steroidal anti-inflammatory drugs (NSAIDs), such as ibuprofen; duloxetine; gabapentin; amitriptyline; and/or strong pain medicines, such as opiates and/or massage, heat, or acupuncture), blood transfusions (including chronic blood transfusions), stem cell or bone marrow transplant, anti-inflammatory therapy (e.g., regadenoson, $NKTT_{120}$, zileuton, montelukast, and/or intravenous immunoglobulin), anti-adhesive therapy (e.g., propranolol, crizanlizumab, PF-04447943, and/or rivipansel), anti-sickling therapy (e.g., $MP_4CO$, SCD-101, SANGUINATE®, and/or AES-103), altered hemoglobin expression therapy (e.g., vorinostat, hydroxyurea with magnesium pidolate, HQK-1001, panibostat, decitabine, and/or pomalidomide), anti-coagulant and anti-platelet therapy (ticagrelor, prasugrel, N-acetyl cysteine, aspirin, and/or eptifibatide), nitric oxide (NO) therapy, ICA-17043 (senicapoc), losartan, 6R-BH4 (sapropterin dihydrochloride), magnesium sulfate, varespladib (A-001), atorvastatin, simvastatin, bosentan, clotrimazole, and/or patient measures to relieve SCD symptoms (e.g., using heating pads for pain relief; consuming an adequate amount of nutrients and water; and regular exercise).

V. COMPOSITIONS COMPRISING 8-SUBSTITUTED GUANINE AND/OR 8-SUBSTITUTED GUANOSINE IN A BEVERAGES

8-Substituted guanine and/or 8-substituted guanosine can be added to any type of beverage, including juice and fermented beverages, such as wine. In some examples, exogenous 8-substituted guanine and/or 8-substituted guanosine can be added to wine at levels greater than are found endogenously to produce a therapeutic effect, such as amounts greater than 500 ng/ml or amounts at about 500- 2,000 ng/ml, 2,000-10,000 ng/ml, 10,000-20,000 ng/ml, 20,000-30,000 ng/ml, 30,000-40,000 ng/ml, and 40,000-50,000 ng/ml.

In some examples, a fermented beverage, such as wine, can be produced by selecting, harvesting and preparing grapes for primary fermentation (see U.S. Patent Application No. US20140302201A1, which is incorporated herein by reference, for information on wine additives). The pulp of the grapes can be fermented with the grape skins to a greater or lesser degree depending on the desired color of the wine. Primary fermentation may occur naturally from the yeast present on the exterior of the grapes, but cultured yeast can be added to the pulp. The temperature applied during fermentation may vary depending the type of wine being produced. The time for primary fermentation can range from between one and two weeks.

After fermentation, the wine can be pumped into tanks to undergo bacterial fermentation, and the skins can be pressed to extract the remaining wine. In some cases, the pressing can precede fermentation. Specially cultivated strains of lactic acid bacteria can be introduced to the wine to convert malic acid into lactic acid. If the pH rises above the desired range, the acidity can be increased by adding tartaric acid. The tanks can be constructed of oak, which imparts oak aromas and tannins to the wine. The wine can be aged in these tanks over a period of weeks up to several months. During this time, the wine can be maintained under an airlock or topped with similar wine to protect it from oxidation. In addition, the remaining yeast cells and other fine particles and proteins from the grapes can be allowed to settle, which clarifies the wine. For some types of wine, a "heat stabilization" step can be included in the process to remove unstable proteins by absorption onto bentonite, preventing them from precipitating in bottled wine.

After fermentation, the wine can be cold stabilized to remove excess tartrates that can form sediment in bottled wine. During the cold stabilization, the temperature of the wine is decreased to just above freezing for one to two weeks. Thereafter, the wine can be drained from the tank. The 8-substituted guanine or 8-substituted guanosine can be added after fermentation, and/or after cold stabilization. In some embodiments, the 8-substituted guanine or 8-substituted guanosine can be added prior to bottling.

The disclosure is illustrated by the following non-limiting Examples.

VI. EXAMPLES

8-Substituted guanine and/or 8-substituted guanosine compounds are used in methods to treat hypertension, stroke, diabetes, and/or patients in need of a diuretic. 8-Substituted guanine and/or 8-substituted guanosine compounds are also included in a beverage composition, which can be a fermented beverage, such as wine. The following examples are provided to illustrate particular features of certain embodiments, but the scope of the claims should not be limited to those features exemplified.

Example 1

This example describes the cardiovascular and renal effects of endogenous 8-substituted guanine and/or 8-substituted guanosine.

Materials. Amiloride, guanosine, guanine, and deoxycorticosterone acetate were purchased from Sigma-Aldrich (St. Louis, Mo.). 8-Nitroguanosine, 8-nitroguanine, 8-aminoguanosine, and 8-aminoguanine were purchased from Toronto Research Chemicals (Toronto, Ontario, Canada). 8-Hydroxyguanosine, 8-hydroxyguanine, and 8-hydroxy-2-deoxyguanosine were purchased from Cayman Chemical (Ann Arbor, Mich.).

Animals. This study employed male Sprague-Dawley rats (Charles River; Wilmington, Mass.) that were approximately 16 weeks old. The Institutional Animal Care and Use Committee approved all procedures. The investigation conforms to the Guide for the Care and Use of Laboratory Animals published by the US National Institutes of Health (NIH Publication No. 85-23, revised 1996).

The rats were anesthetized with Inactin (90 mg/kg, i.p.) and placed on an isothermal pad, and body temperature was monitored with a rectal probe thermometer and maintained at 37° C. with a heat lamp. In each rat, the trachea was cannulated with polyethylene (PE)-240 to facilitate respiration, and a PE-50 cannula was inserted into the carotid artery and connected to a digital blood pressure analyzer (Micro-Med, Inc., Louisville, Ky.) for continuous measurement of mean arterial blood pressure (MABP) and heart rate (HR). A PE-50 cannula was inserted into the jugular vein, and an infusion of 0.9% saline at 25 µl/min was initiated. A PE-10 tubing was placed in the left ureter for urine collection. Non-cannulating, transit-time flow probes (Transonic Systems, Inc, Ithaca, N.Y.) were placed on the left renal (1 mm) and mesenteric (2 mm) arteries and were connected to a 2-channel small animal transit-time flow meter (model T-206; Transonic Systems, Inc) for measurement of renal blood flow (RBF) and mesenteric blood flow (MBF). After a one-hour stabilization period, urine was collected for 30 minutes while MABP and HR were time-averaged (Period 1: 0-30 minutes into protocol). Next, the test compounds dissolved in the vehicle (0.9% saline containing 0.03 N HCl) and were administered as an intravenous bolus at 33.5 µmoles/kg. The dose was selected based on preliminary experiments with 8-aminoguanosine. One group received vehicle only to confirm that the vehicle did not affect any of the measured variables and to confirm that our model was stable for the 115 minute observation period. Each group of rats (n of at least 6) received only one treatment. Ten minutes after the test agents were administered, urine was collected for another 30 minutes (Period 2: 30-70 minutes into the protocol). After a 15-minute waiting period, urine was again collected for 30 minutes (Period 3: 85-115 minutes into the protocol). During each urine collection period, MABP and HR were continuously recorded, and RBF and MBF were recorded at 10, 20, and 30 minutes into the urine collection period. The sodium and potassium in the urine was measured by flame photometry (Model IL-943; Instrumentations Laboratory Inc., Lexington, Mass.), and the glucose in the urine was measured using a glucose colorimetric assay kit (Cayman Chemical).

Statistics. Absolute values are presented as the mean±SEM. Fold-increases were calculated as follows: Period 3 value÷Period 1 value. Statistical analyses were performed using analysis of variance (ANOVA) followed by Fisher's Least Significant Difference (LSD) test if the overall effects or interactions in the ANOVA were significant. P<0.05 was considered statistically significant.

Results. To ensure the reliability of our results, we conducted two experimental series to confirm that our animal preparation was both stable and responsive. In the first quality-control series, in 6 rats, baseline urine was collected during Period 1; the vehicle for the test compounds was then injected intravenously, and urine was collected post-injection during Periods 2 and 3. As shown in FIGS. 2A-2H, urine volume, sodium excretion, potassium excretion, glucose excretion, MABP, HR, MBF, and RBF were not affected by time or the vehicle. These experiments indicate that our preparation was stable. In the second quality-control series, in another 6 rats, baseline urine was collected during Period 1; the diuretic amiloride (33.5 µmoles/kg, which is the same dose used for the guanine and guanosine analogue experiments) was then injected intravenously, and urine was collected post-injection during Periods 2 and 3. As illustrated in FIGS. 3A-3H, amiloride caused robust diuresis and natriuresis, while suppressing potassium excretion. Compared to Period 1 (baseline period), during Period 3 (85-115 minute urine collection), urine volume and sodium excretion increased by 4.5-fold and 13.6-fold, respectively, whereas potassium excretion decreased by 96.5%. Amiloride did not change glucose excretion, but it modestly decreased the MABP, HR, MBF, and RBF. These experiments indicate that our preparation was responsive to a known diuretic.

The most efficacious 8-substituted guanosine compound was 8-aminoguanosine (FIGS. 4A-4H), which, like amiloride, markedly increased the urine volume and sodium excretion while suppressing potassium excretion. In this regard, compared with Period 1, during Period 3, 8-aminoguanosine increased the urine volume and sodium excretion by 4.2-fold and 26.6-fold, respectively, whereas 8-aminoguanosine decreased potassium excretion by 69.1%. Unlike amiloride, 8-aminoguanosine induced a striking increase in glucose excretion during Period 3 (12.1-fold). 8-Aminoguanosine did not affect MABP or HR but modestly increased MBF and decreased RBF.

The most efficacious 8-substituted guanine compound was 8-aminoguanine (FIGS. 5A-5H), which, like amiloride and 8-aminoguanosine, robustly increased the urine volume and sodium excretion while attenuating potassium excretion. Compared with Period 1, during Period 3, 8-aminoguanine increased the urine volume and sodium excretion by 3.6-fold and 17.2-fold, respectively, whereas 8-aminoguanine decreased potassium excretion by 71.0%. Unlike amiloride, but similar to 8-aminoguanosine, 8-aminoguaine increased glucose excretion 12.2-fold during Period 3. During Period 3, 8-aminoguanine did not affect the MABP, HR, MBF, or RBF.

The other compounds tested in this series can be grouped into compounds with moderate efficacy and compounds with little or no efficacy. The compounds with moderate efficacy include guanine (FIGS. 6A-6H), 8-nitroguanine (FIGS. 7A-7H), 8-hydroxyguanosine (FIGS. 8A-8H), and 8-hydroxyguanine (FIGS. 9A-9H). With regard to sodium excretion, these compounds induced 9.4-fold, 7.8-fold, 7.1-fold, and 8.6-fold increases, respectively (Period 3 compared with Period 1). These compounds exerted no or small and variable effects on potassium and glucose excretion. The compounds with little or no efficacy include guanosine, 8-nitroguanosine, and 8-hydroxy-2-deoxyguanosine.

Example 2

This example describes the effects of 8-aminoguanosine and 8-aminoguanine on DOCA-salt hypertension. Rats were instrumented for long-term and continuous measurement of arterial blood pressure by radiotelemetry as recently described (Jackson E K et al., Hypertension, 65:238-249, 2015). After at least 20 days of from the time of radiotransmitter implantation, hypertension was induced in the animals by removing one kidney, subcutaneously administering deoxycorticosterone acetate (30 mg/kg twice weekly), and providing 1% NaCl as drinking water (i.e., DOCA-salt hypertension). At this time, some animals were also randomized to receive either drinking water without 8-aminoguanosine or drinking water containing 8-aminoguanosine (10 mg/kg/day). In two other experiments, 8-aminoguanosine (5 mg/kg/min) or 8-aminoguanine (5 mg/kg/day) was administered 13 days before DOCA-salt hypertension was induced.

Results. Three studies were conducted to assess the effects of 8-aminoguanosine and 8-aminoguanine on DOCA-salt hypertension. In one study, DOCA-salt hypertension was induced at the same time that treatment with 8-aminoguanosine (10 mg/kg/day) was initiated. In two other studies, treatment with 8-aminoguanosine (5 mg/kg/day) or 8-aminoguanine (5 mg/kg/day) was initiated 13 days before inducing DOCA-salt hypertension. Treatments were maintained for the duration of the studies, and the MABP was continuously monitored by radiotelemetry. As shown in FIGS. 10A-10C, 8-aminoguanosine at 10 mg/kg/day prevented DOCA-salt hypertension. Pretreatment of rats with 8-aminoguanosine (5 mg/kg/day) or 8-aminoguaine (5 mg/kg/day) did not affect the basal MABP but markedly attenuated the development of DOCA-salt hypertension.

Example 3

Figure 11A:
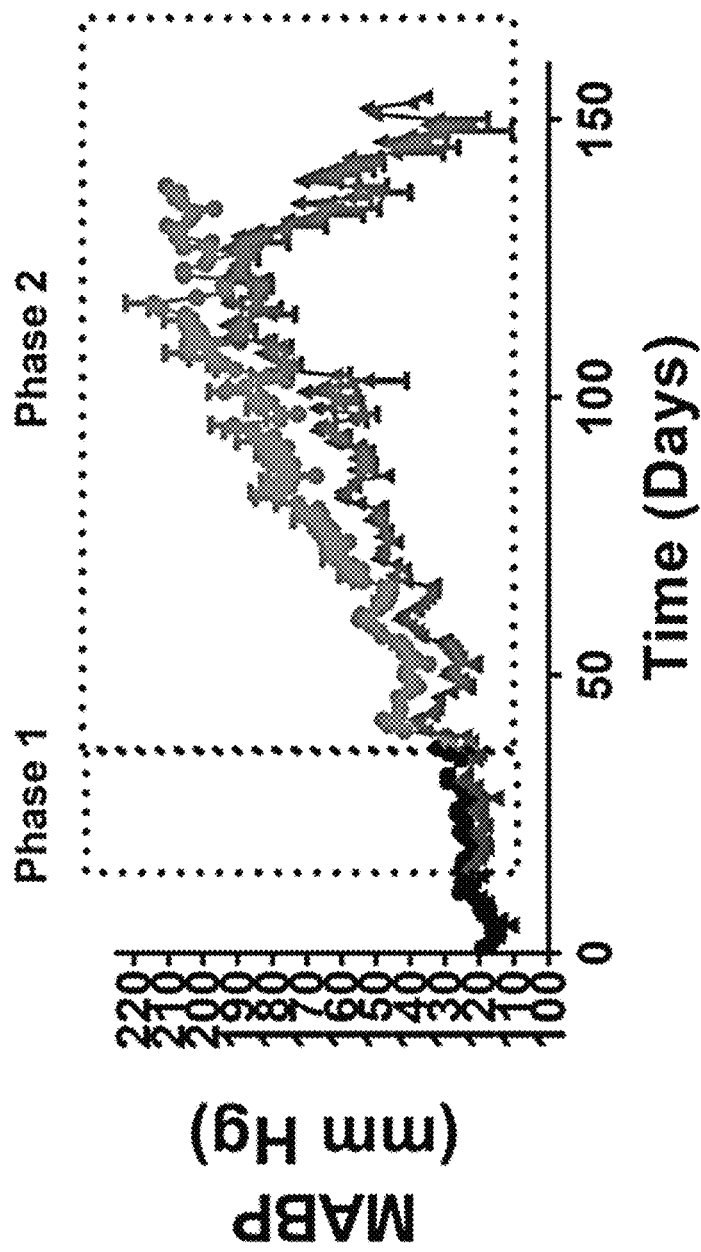
FIGS. 11A-11B: Line graphs depict the long-term effects on mean arterial blood pressure (MABP) of (A) 8-aminoguanine and (B) 8-aminoguanosine on Dahl salt-sensitive rats (Dahl SS). During phase 1, all rats received a low-salt (0.3% NaCl) diet. During phase 2, all animals received a high-salt (8% NaCl) diet.
Figure 11B:
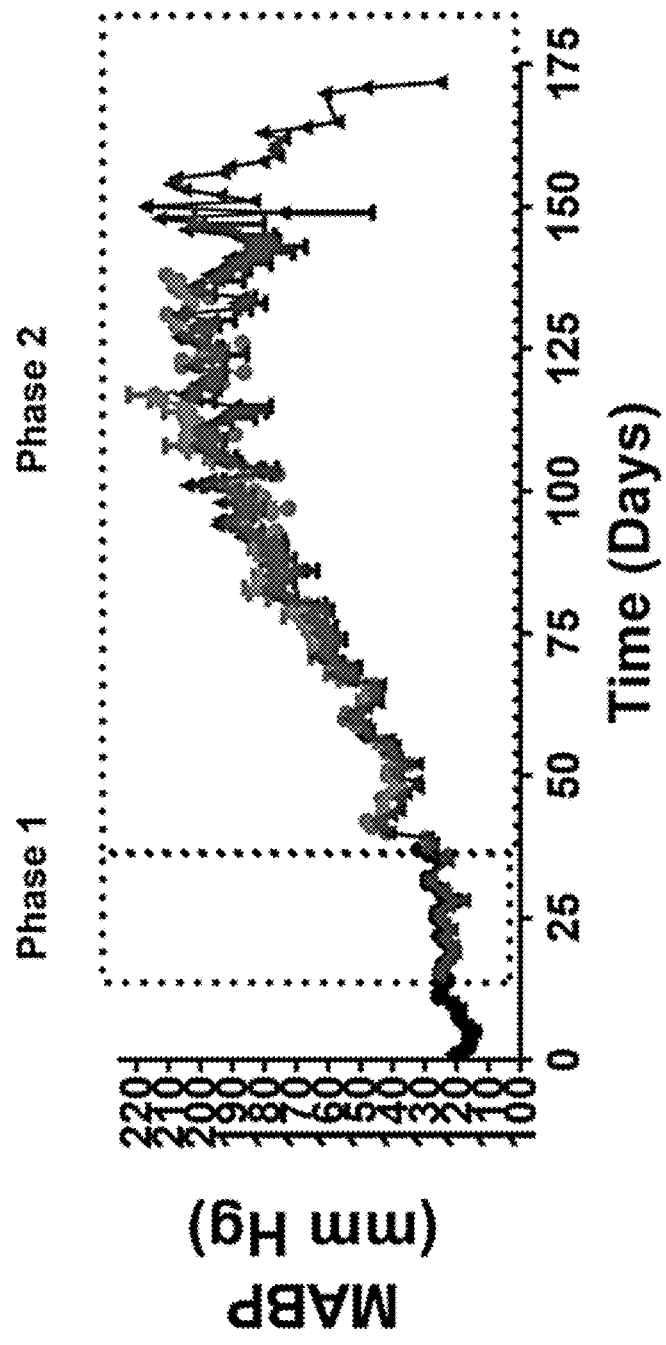

This example describes the long-term effects of 8-aminoguanine (FIG. 11A) and 8-aminoguanosine (FIG. 11B) on mean arterial blood pressure (MABP) in Dahl salt-sensitive rats (Dahl SS). Dahl SS are a well-established model of salt-sensitive hypertension. All animals were instrumented for long-term measurement of MABP by radiotelemetry as previously described (Jackson E K et al., *Hypertension*, 65:238-249, 2015). Group 1 Dahl SS received only normal drinking water, whereas Group 2 received normal drinking water for 7 days and then were provided drinking water containing either 8-aminoguanine or 8-aminoguanosine (10 mg/kg/day) for the remainder of the study. The experiment was divided into two phases (indicated by the boxes). During phase 1, all rats received a low-salt (0.3% NaCl) diet. During phase 2, all animals received a high-salt (8% NaCl) diet. The study was continued until all animals expired, so the sample size decreases with time. The blood pressures of the 8-aminoguanine- and 8-aminoguanosine-treated rats were obtainable for a longer period of time because they survived longer. These results show that 8-aminoguanine decreases MABP in Dahl SS on a high-salt diet. Unlike 8-aminoguanine, 8-aminoguanosine did not alter MABP in Dahl SS on a high-salt diet. Therefore, any stroke and survival benefit for 8-aminoguanosine cannot be attributed to changes in MABP. Why 8-aminoguaine, but not 8-aminoguanosine, lowers MABP in Dahl SS on a high-salt diet is currently unknown, but may be due to different pharmacokinetics of the compounds in this rat strain.

Example 4

Figure 12A:
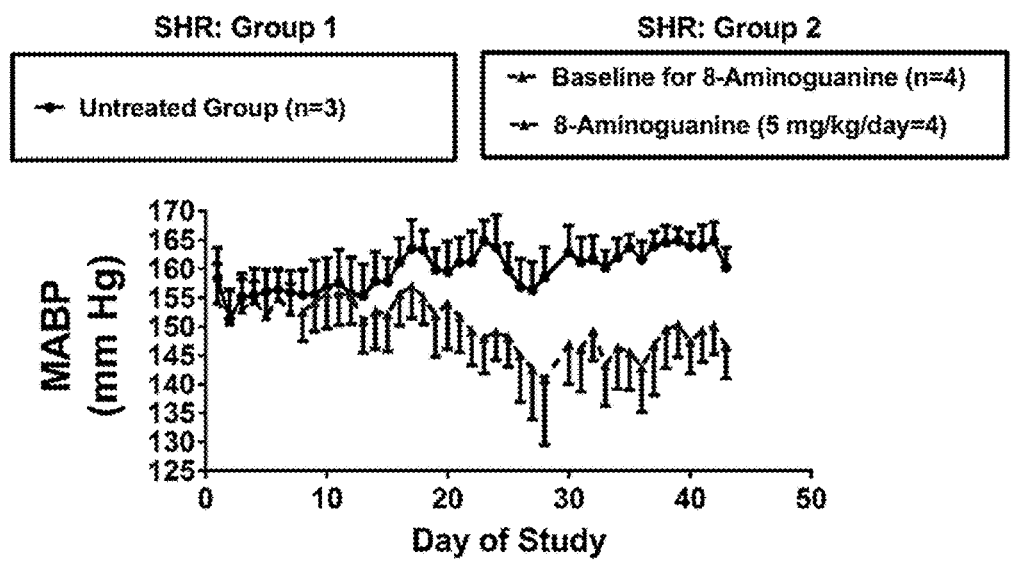
FIGS. 12A-12B: The long-term effects of 8-aminoguanine on mean arterial blood pressure (MABP) in spontaneously hypertensive rats (SHR). (A): The day-to-day average levels of MABP in the two groups; (B): the change in MABP from the baseline in Group 1 versus Group 2. Two-factor analysis of variance and post-hoc tests were performed.
Figure 12B:
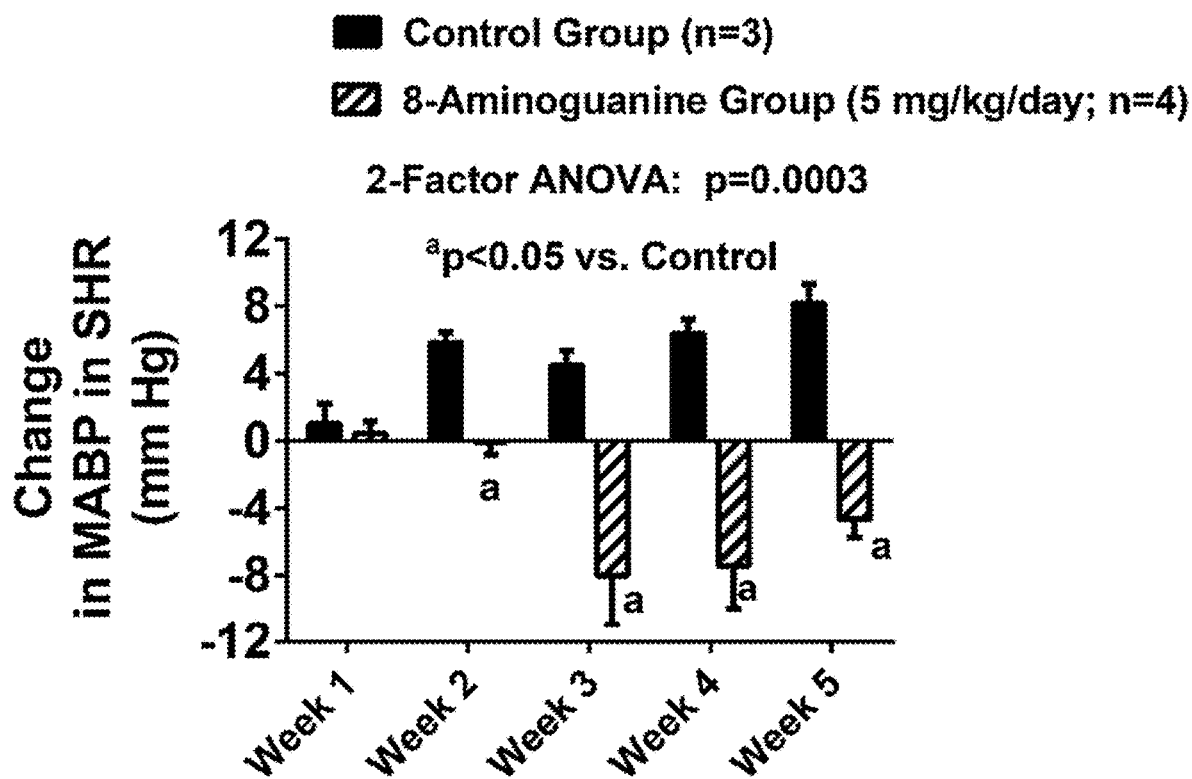
Figure 13A:
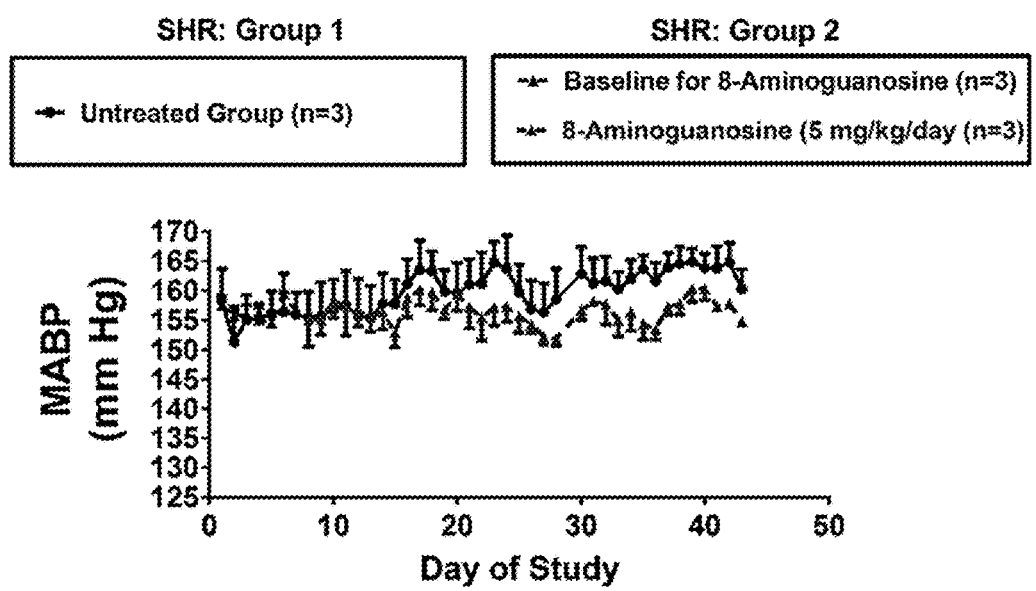
FIGS. 13A-13B: The long-term effects of 8-aminoguanosine on mean arterial blood pressure (MABP) in spontaneously hypertensive rats (SHR). (A): The day-to-day average levels of MABP in the two groups; (B): the change in MABP from the baseline in Group 1 versus Group 2.
Figure 13B:
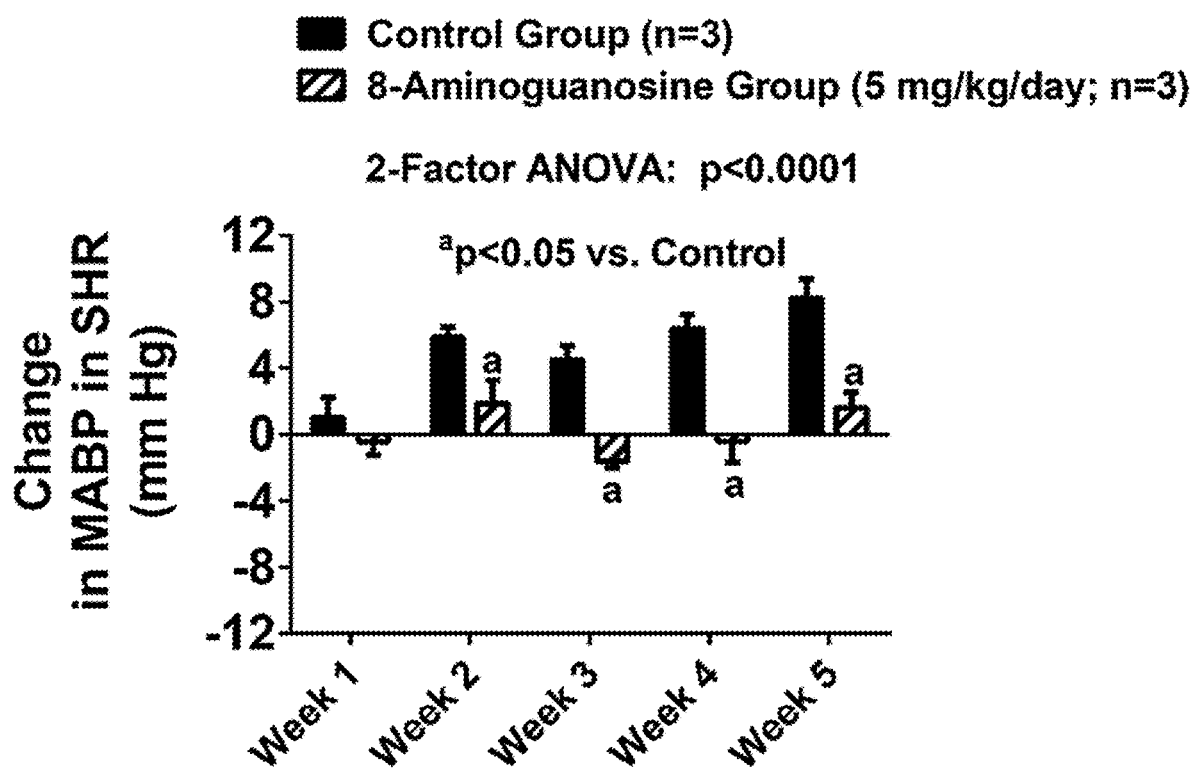

This example describes the long-term effects of 8-aminoguanine (FIGS. 12A-12B) and 8-aminoguanosine (FIGS. 13A-13B) on mean arterial blood pressure (MABP) in spontaneously hypertensive rats (SHR). SHR are a well-established animal model of genetic hypertension that is not salt sensitive. All animals were instrumented for long-term measurement of MABP by radiotelemetry as previously described (Jackson E K et al., *Hypertension*, 65:238-249, 2015). Group 1 SHR received only normal drinking water; whereas Group 2 received normal drinking water for 7 days and then were provided drinking water containing 8-aminoguanine or 8-aminoguanosine (5 mg/kg/day) for the remainder of the study. Two-factor analysis of variance revealed significant (p<0.0001) effects from 8-aminoguanine and 8-aminoguanosine on MABP, and post-hoc tests (a) indicated a significant difference during weeks 2, 3, 4, and 5 after initiating 8-aminoguanine and 8-aminoguanosine. These results indicate that 8-aminoguanine and 8-aminoguanosine are antihypertensive even in a model of genetic hypertension.

Example 5

This example describes the long-term effects of 8-aminoguanine (FIG. 14A) and 8-aminoguanosine (FIG. 14B) on mean arterial blood pressure (MABP) in obese Zucker Diabetic Sprague Dawley rats (ZDSD). Obese ZDSD are a recently developed model (developed by PreClinOmics) of metabolic syndrome that have a mild elevation of MABP and have dyslipidemia, diabetes, and obesity. All animals were instrumented for long-term measurement of MABP by radiotelemetry as previously described (Jackson E K et al., *Hypertension*, 65:238-249, 2015). Group 1 ZDSD received only normal drinking water, whereas Group 2 received normal drinking water for 7 days and then were provided drinking water containing 8-aminoguanine or 8-aminoguanosine (10 mg/kg/day) for the remainder of the study. The experiment was divided into three phases (indicated by the boxes). During phase 1, no other treatments were provided. During phase 2, all animals received 1% salt (NaCl) in their drinking water. During phase 3, all animals were provided (in addition to 1% salt in the drinking water) a diabetogenic diet to worsen diabetes. The numbers in each box are the average MABP in Group 2 versus Group 1 during the time period indicated by the box. P-values comparing Group 2 versus Group 1 during each phase of the experiment are also provided. These results indicate that 8-aminoguanine and 8-aminoguanosine decrease MABP in metabolic syndrome, even when salt intake is increased and a diabetogenic diet is consumed.

Example 6

Figure 15A:
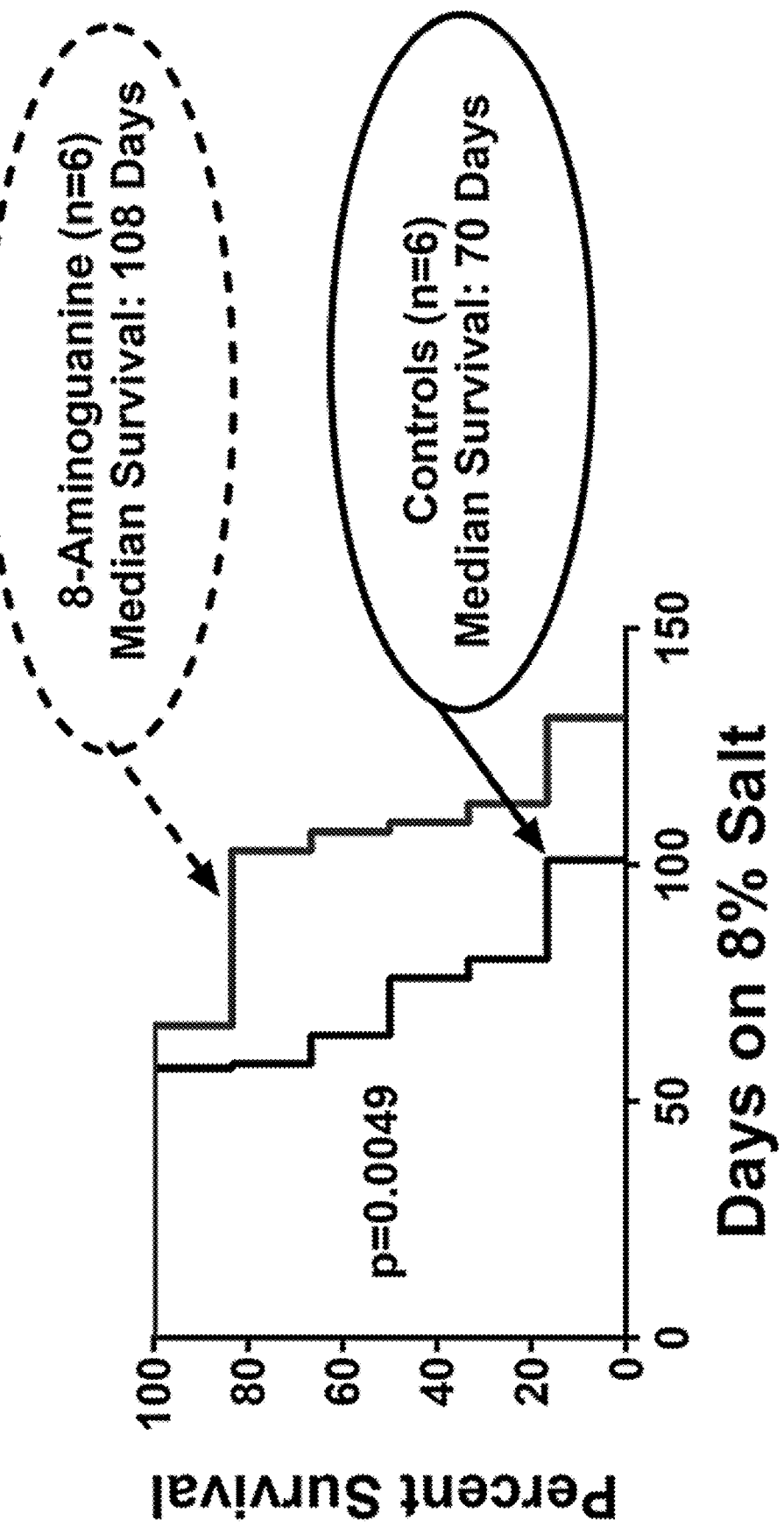
FIGS. 15A-15B: The long-term effects of 8-aminoguanine (A) and 8-aminoguanosine (B) on survival in Dahl SS. The control group was also provided a high-salt diet at the same time as the treated group.
Figure 15B:
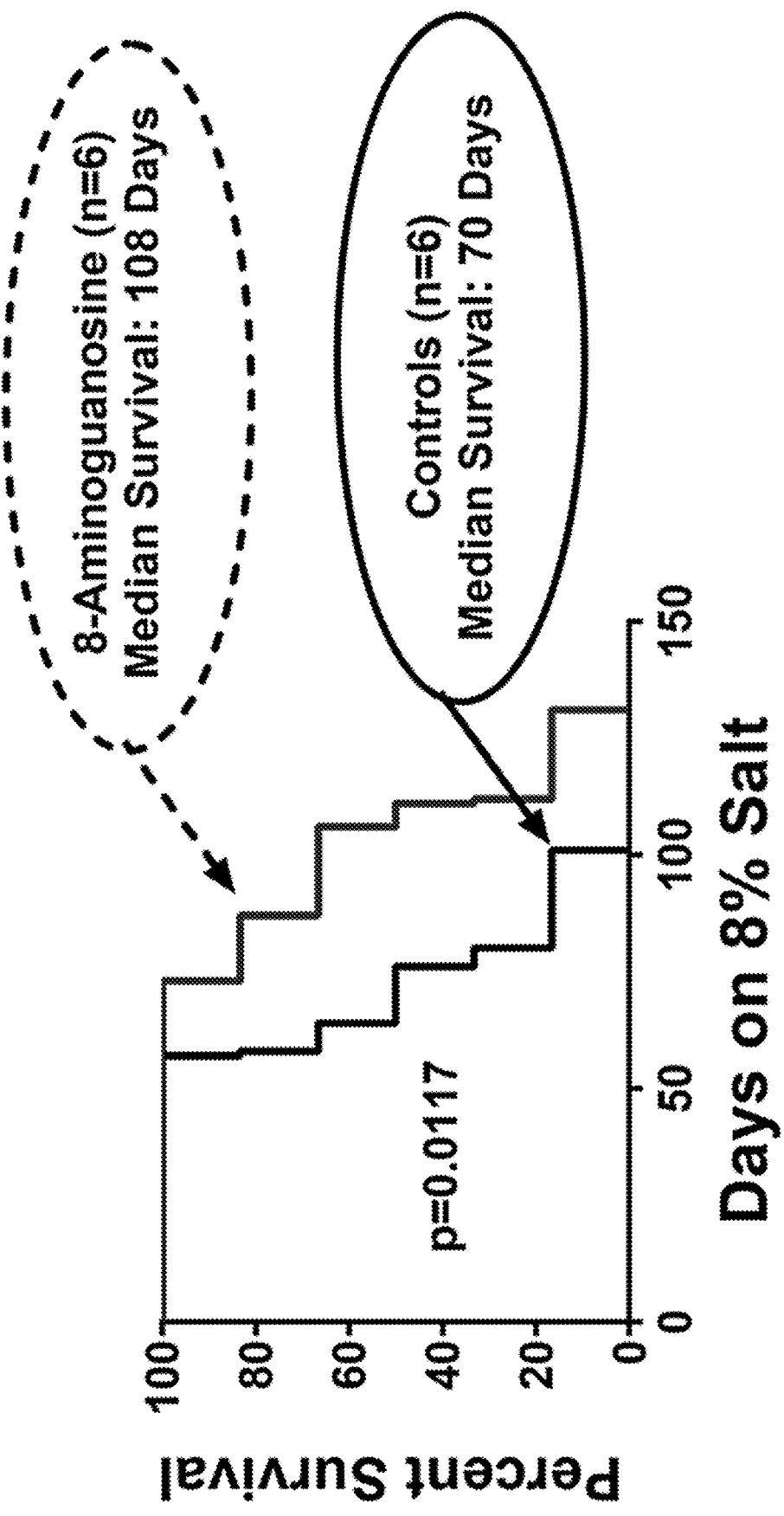

This example describes the long-term effects of 8-aminoguanine (FIG. 15A) and 8-aminoguanosine (FIG. 15B) on survival in Dahl salt-sensitive rats (Dahl SS). Dahl SS are a well-established model of salt-sensitive hypertension. The control group of Dahl SS received only normal drinking water; whereas the treatment group received 8-aminoguanine or 8-aminoguanosine (10 mg/kg/day) beginning 23 days before starting a high-salt (8% NaCl) diet and continuing until all animals expired. The control group was also provided a high-salt diet at the same time as the treated group. FIGS. 15A-15B show survival curves for the control group versus the 8-aminoguanine-treated group or 8-aminoguanosine-treated group.

The median survival time in the control group was 70 days and the median survival time in the 8-aminoguanine- and aminoguanosine-treated groups was 108 days (p=0.0049 and p=0.0117, respectively). Thus, 8-aminoguanine and 8-aminoguanosine each afforded a 54% increase in lifespan. The control group's blood pressure remained high until the moment of death and death was sudden (as assessed by continuous radiotelemetry monitoring). Some control animals had hemiparalysis before expiring, and infarction of the brain was observed in a control rat by MRI (see FIG. 16). Thus, it appears that all of the control rats died of massive strokes. In contrast, the 8-aminoguanine- and 8-aminoguanosine-treated animals did not exhibit hemiparalysis, and death was preceded by a gradual decrease in blood pressure over several days. Most likely, the Dahl SS in the 8-aminoguanine- and 8-aminoguanosine-treated groups died of congestive heart failure due to the long exposure of the heart to extremely high levels of hypertension. In other words, because the treated animals were protected against strokes, they lived longer and eventually succumbed to hypertension-induced heart failure. The stroke and mortality benefit of 8-aminoguanosine was not due to blood pressure lowering because 8-aminoguanosine (unlike 8-aminoguanine) did not decrease MABP in Dahl SS on a high-salt diet (see FIGS. 11A-11B).

Example 7

This example describes an MRI analysis of strokes in Dahl SS (FIG. 16). Six-week-old Dahl SS were purchased from Charles River. When animals arrived, they were divided into 4 groups. Group A is the normal control group in which the Dahl SS were maintained on a 0.3% salt diet for the entire study. Group B is the positive control group in which the Dahl SS were maintained on an 8% salt diet for the entire study. Group C is the 8-aminoguanosine group in which Dahl SS were maintained on an 8% salt diet with 10 mg/kg/day of 8-aminoguanosine in their drinking water for the entire study. Group D is the 8-aminoguanine group in which the Dahl SS were maintained on an 8% salt diet with 10 mg/kg/day of 8-aminoguanine in their drinking water for the entire study. After 40 days of treatment, the rats were transported to an MRI facility for T2-weighted MRI of the brain. Stroke was detected in the Dahl SS maintained on an 8% salt diet, but not in any of the other groups, which indicates that 8-aminoguanosine and 8-aminoguanine protect against strokes.

Example 8

This example describes the presence and quantity of 8-aminoguanine (FIG. 17A) and 8-aminoguanosine (FIG. 17B) in red wine. Kendall Jackson Vintner's Reserve Zinfandel 2012 was purchased from a liquor store in Pittsburgh, Pa., and 10 µl was diluted 1:1000 with water. The sample was analyzed using ultra-performance liquid chromatograph-tandem mass spectrometry as follows. The sample was spiked with a heavy-isotope internal standards ($^{13}$C-guanine and $^{13}$C-guanosine). 8-Aminoguanine and 8-aminoguanosine were resolved by reversed-phase ultra-performance liquid chromatography (Waters UPLC BEH C18 column, 1.7 µm beads; 2.1×150 mm; Milford, Mass.) and quantified using a triple quadrupole mass spectrometer (TSQ Quantum-Ultra; ThermoFisher Scientific, San Jose, Calif.) operating in the selected reaction monitoring mode with a heated electrospray ionization source. The mobile phases were delivered with a Waters Acquity ultra pressure liquid chromatographic system and consisted of linear gradient changes involving two mobile phases: Mobile Phase A, 1% acetic acid in water; and Mobile Phase B, methanol. The mobile phase flow rate was 300 µL/min. The mobile phase gradient (A/B) is shown in Table 1.

TABLE 3

Mobile phase gradient.

| Time (min) | %A | %B |
|---|---|---|
| 0 | 99.6 | 0.4 |
| 2.0 | 99.6 | 0.4 |

TABLE 3-continued

Mobile phase gradient.

| Time (min) | %A | %B |
|---|---|---|
| 3.0 | 98.0 | 2.0 |
| 4.0 | 85.0 | 15.0 |
| 6.5 | 99.6 | 0.4 |

The instrument settings were as follows:
Sample tray temperature: 10° C.
Column temperature: 50° C.
Ion Spray Voltage: 4.0 kilovolts
Ion Transfer Tube Temperature: 350° C.
Source Vaporization Temperature: 320° C.
Q2 CID Gas: Argon at 1.5 mTorr
Sheath Gas: Nitrogen at 60 psi
Auxillary Gas: Nitrogen at 35 psi
Q1/Q3 Width: 0.7/0.7 u full-width half-maximum
Scan Width, 0.6 u
Scan Time, 0.01 seconds.

8-Aminoguanosine was detected using the selected reaction monitoring transition of 299 m/z (parent ion) to 167 m/z (daughter ion) and identified by matching retention time to authentic 8-aminoguanosine. 8-Aminoguanine was detected using the selected reaction monitoring transition of 167 m/z (parent ion) to 150 m/z (daughter ion) and identified by the matching retention time to authentic 8-aminoguanine. The concentrations in the sample were calculated by determining the ratio of 8-aminoguanosine to $^{13}$C-guanosine and 8-aminoguanine to $^{13}$C-guanine and then applying those ratios to standard curves.

Figure 17A:
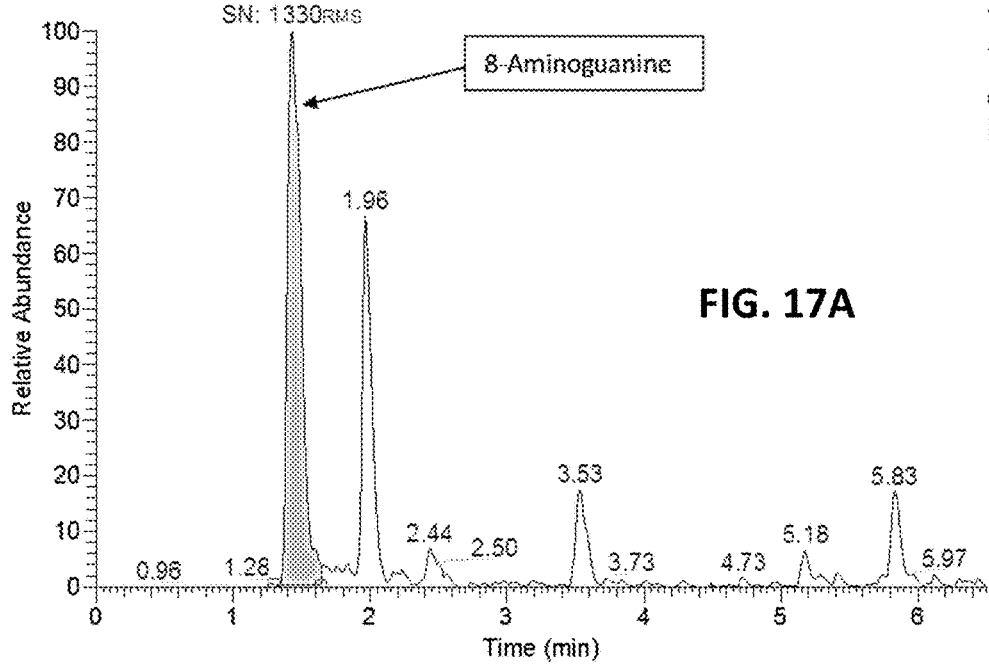
FIGS. 17A-17B: The presence and quantity of 8-aminoguanine and 8-aminoguanosine in red wine.
Figure 17B:
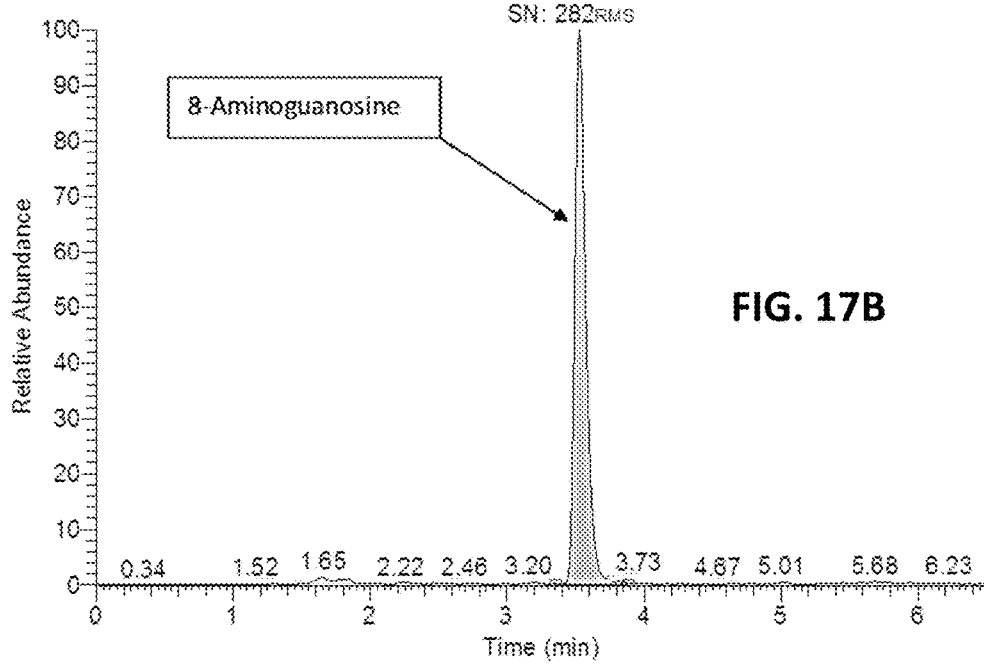

FIGS. 17A-17B show the detection of 8-aminoguanine (retention time of 1.43 minutes; (FIG. 17A) and 8-aminoguanosine (retention time of 3.53 minutes; (FIG. 17B). The concentrations in this wine sample (adjusted for dilution factor) were the following for Kendall Jackson Vintner's Reserve Zinfandel 2012: 8-aminoguanine=82 ng/ml, 8-aminoguanosine=385 ng/ml. In addition to this wine sample, we also measured concentrations of 8-aminoguanine and 8-aminoguanosine in 5 other wines as shown in Table 2.

TABLE 4

Concentrations of 8-aminoguanine and 8-aminoguanosine in red wines.

| Wine | 8-aminoguanine | 8-aminoguanosine |
|---|---|---|
| Kendall Jackson Vintner's Reserve Zinfandel 2012 | 82 ng/ml | 385 ng/ml |
| Dreaming Tree North Coast Cabernet Savignon 2010 | 8 ng/ml | 84 ng/ml |
| Frei Brothers Cabernet Savignon Sonmoma County 2011 | 14 ng/ml | 137 ng/ml |
| Goose Bay East Coast New Zealand Pinot Noir 2012 | 16 ng/ml | 211 ng/ml |
| Michael David Winery The Seven Deadly Zins Zinfandel 2012 | 19 ng/ml | 194 ng/ml |
| Ravenswood Zen of Zin Sonoma Zinfandel 2012 | 35 ng/ml | 155 ng/ml |

Example 9

Figure 18:
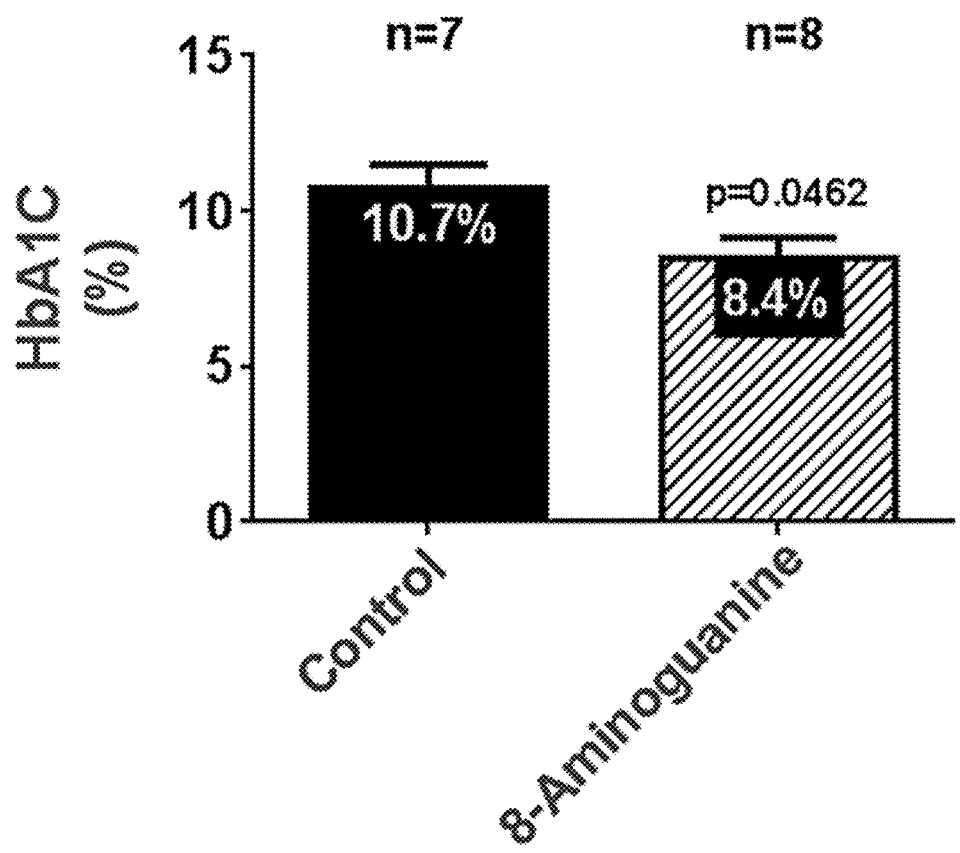
FIG. 18: Glycated hemoglobin HbA1C levels in blood from rats with the metabolic syndrome (i.e., obese ZDSD) at the end of a diabetogenic diet.

This example describes the long-term effects of 8-aminoguanine on (FIG. 18) on glycated hemoglobin (HbA1C) levels in blood from rats with the metabolic syndrome (i.e., obese ZDSD) at the end of a diabetogenic diet. Obese ZDSD are a recently developed model (developed by PreClinOmics) of metabolic syndrome that have a mild elevation of MABP and have dyslipidemia, diabetes, and obesity. Chronic treatment with 8-aminoguanosine (10 mg/kg/day) significantly lowered HbA1C levels. These data show that 8-aminoguanine has a dramatic anti-diabetic effect in the metabolic syndrome.

Example 10

The example describes methods and materials used in Examples 11-14.

Materials. 8-Aminoguanosine and 8-aminoguanine were purchased from Toronto Research Chemicals (Toronto, Ontario, Canada).

Animals. Male Sprague-Dawley rats (Charles River; Wilmington, Mass.) approximately 16 weeks old were employed. The Institutional Animal Care and Use Committee approved all procedures. The investigation conforms to National Institutes of Health Guide for the Care and Use of Laboratory Animals.

Protocol 1. After inducing anesthetization with Inactin® (90 mg/kg, i.p.), each rat was positioned on an isothermal pad. A thermometer probe was inserted into the rectum, and the rat's body temperature was continuously monitored and maintained at 37° C. by adjusting the distance of a heat lamp from the animal's body. Using polyethylene (PE)-240 tubing, the trachea was cannulated to aid respiration. Next, a PE-50 cannula was inserted into the carotid artery and connected to a digital blood pressure analyzer (Micro-Med, Inc., Louisville, Ky.) for continuous measurement of mean arterial blood pressure (MABP) and heart rate (HR). A PE-50 cannula was placed in the jugular vein, and infusion of 0.9% saline (50 µl/min) began. After a stabilization period of approximately one hour, urine was collected for 30 minutes, while MABP and HR were time-averaged (Period 1: 0-30 minutes into protocol). Next, 8-aminoguanosine (33.5 µmoles/kg; 1 ml/kg) or 8-aminoguanine (33.5 µmoles/kg; 1 ml/kg) or vehicle (0.9% saline containing 0.03 N HCl; 1 ml/kg) was administered intravenously as a bolus. The dose was selected based on Examples 1-7. Rats were randomized to treatment groups, and the rats in each group received only one treatment. Ten minutes after the treatments, urine was collected for another 30 minutes (Period 2: 30-70 minutes into protocol). After a 15-minute rest period, urine was again collected for 30 minutes (Period 3: 85-115 minutes into protocol). During each urine collection period, the MABP and HR were continuously recorded. Further, at the midpoint of each 30-minute urine collection period, a blood sample (0.5 ml) was obtained to measure plasma creatinine (Creatinine Colorimetric Assay Kit; catalogue number, 500701; Cayman Chemical; Ann Arbor, Mich.) and aldosterone (Aldosterone ELISA Kit; catalogue number, ADI-900-173; Enzo Life Sciences, Farmingdale, N.Y.) and to determine sodium and potassium by flame photometry (Model IL-943; Instrumentations Laboratory Inc., Lexington, Mass.). Sodium and potassium were also measured in urine (flame photometry) as was glucose (Glucose Colorimetric Assay Kit; catalogue number, 10009582; Cayman Chemical). Creatinine clearance was calculated as an estimate of glomerular filtration rate (GFR).

Protocol 2. Rats were prepared in a similar fashion to that described in Protocol 1, but with modifications. Specifically, microdialysis probes were inserted into the cortex and medulla of the right kidney and were perfused at 2 µl/min with 0.9% saline. The microdialysis probes used in this protocol were from Bioanalytical Systems (West Lafayette, Ind.; CMA/20 microdialysis probe 4 mm; outer diameter of 0.5 mm; 20,000 dalton membrane cut-off). After initiating the probe perfusions, the infusion rate of 0.9% saline via the jugular vein was reduced to 25 µl/min to avoid volume overload. The rats then stabilized for two hours for the kidney to recover from the trauma induced by the probe insertions.

Next, microdialysate from the renal cortex and medulla as well as urine were collected for 30 minutes, and MABP and HR were time averaged during this first (basal) period. Rats were then randomized to receive 8-aminoguanosine, 8-aminoguanine, or vehicle using the dose and manner described for Protocol 1. Ten minutes after the treatments, microdialysate from the renal cortex and medulla as well as urine were again collected for 30 minutes, and MABP and HR were time averaged during this treatment period. After 15 minutes, this procedure was repeated. 8-Aminoguanosine and 8-aminoguanine were measured in urine and microdialysate using ultra-performance liquid chromatography-tandem mass spectrometry (LC-MS/MS) as described below.

Protocol 3. Rats were prepared similar to the Protocol 1 description, but with a few additions. For this protocol, PE-10 cannulas were inserted into both the left and right ureters for simultaneous urine collection from both kidneys. A 1 mm transit-time flow probe was also positioned on the left renal artery and connected to a flowmeter (model T-206, Transonic Systems, Inc., Ithaca, N.Y.) to continuously measure renal blood flow (RBF). As placing a flow probe on left renal artery partially denervates the kidney, both kidneys were denervated to ensure similar conditions for both kidneys. Finally, a 30-gauge needle was inserted into the lumen of the left renal artery, and an infusion of 0.9% saline at 50 µl/min was initiated. The infusion rate of 0.9% saline via the jugular vein was reduced to 25 µl/min to avoid volume overload.

After stabilization for one hour, urine was collected from both kidneys for 15 minutes (for urine volume, sodium, potassium, and glucose), and MABP as well as HR were time averaged during this period. In addition, RBF was recorded 5, 10, and 15 minutes into the 15-minute urine collection period and averaged. Next, the rats received an infusion into the left renal artery of 8-aminoguanine or 8-aminoguanosine at 0.1 µmoles/kg/min and 50 µl/min or of vehicle at 50 µl/min. After 10 minutes, urine was again collected for 15 minutes, and all measurements were repeated. In rats receiving 8-aminoguanine or 8-aminoguanosine, the dose of these compounds was increased to 0.3 µmoles/kg/min. After 10 minutes, urine was again collected for 15 minutes, and all measurements were repeated. The procedure was repeated once more after the dose of 8-aminoguanosine or 8-aminoguanine was increased to 1 µmole/kg/min. Sodium, potassium, and glucose were measured in all urine samples as described in Protocol 1.

Assay for 8-Aminoguanosine and 8-Aminoguanine. The purines in the urine and microdialysate were measured by LC-MS/MS using a method similar to a previously described method (Jackson et al., J Biol Chem 284:33097-33106, 2009), but with modifications. Purines were separated using reversed-phase ultra-performance liquid chromatography (Waters UPLC BEH C18 column, 1.7 µm beads; 2.1×150 mm; Milford, Mass.) and quantified by selected reaction monitoring using a triple quadrupole mass spectrometer (TSQ Quantum-Ultra; ThermoFisher Scientific, San Jose, Calif.) with a heated electrospray ionization source. The mobile phase included a linear gradient flow rate (300 uL/min) of 1% acetic acid in water (pH, 3; mobile phase A) as well as 100% methanol (mobile phase B) and was delivered with a Waters Acquity ultra-performance liquid chromatographic system. The gradient (A/B) settings were as follows: from 0 to 2 minutes, 99.6%/0.4%; from 2 to 3 minutes, to 98.0%/2.0%; from 3 to 4 minutes, to 85.0%/15.0%; and from 4 to 6.5 minutes, to 99.6%/0.4%. The instrument parameters were as follows: sample tray temperature, 10° C.; column temperature, 50° C.; ion spray voltage, 4.0 kilovolts; ion transfer tube temperature, 350° C.; source vaporization temperature, 320° C.; Q2 CID gas, argon at 1.5 mTorr; sheath gas, nitrogen at 60 psi; auxillary gas, nitrogen at 35 psi; Q1/Q3 width, 0.7/0.7 units full-width half-maximum; scan width, 0.6 units; and scan time, 0.01 seconds. For 8-aminoguanosine, the parent ion was m/z=299, the daughter ion was m/z=167, and the retention time was 3.64 min. For 8-aminoguanine, the parent ion was m/z=167, the daughter ion was m/z=150, and the retention time was 1.50 min. The internal standard for 8-aminoguanosine was $^{13}C_{10},^{15}N_5$-guanosine (parent ion, m/z=299; daughter ion, m/z=162; retention time, 3.10 min). The internal standard for 8-aminoguanine was $^{13}C_2,^{15}N$-guanine (parent ion, m/z=155; daughter ion, m/z=138; retention time, 1.56 min).

Statistics. Statistical analysis was performed using 1- or 2-factor repeated measures analysis of variance (ANOVA) followed by a Fisher's Least Significant Difference (LSD) test if the effects in the ANOVA were significant. The criterion of significance was p<0.05. The values are presented as the mean±SEM.

Example 11

This examples describes effects of administering 8-substituted guanine and 8-substituted guanosine on MABP, plasma aldosterone concentrations, GFR, urinary potassium excretion, urine volume, urinary sodium excretion, and urinary glucose excretion.

Figure 19A:
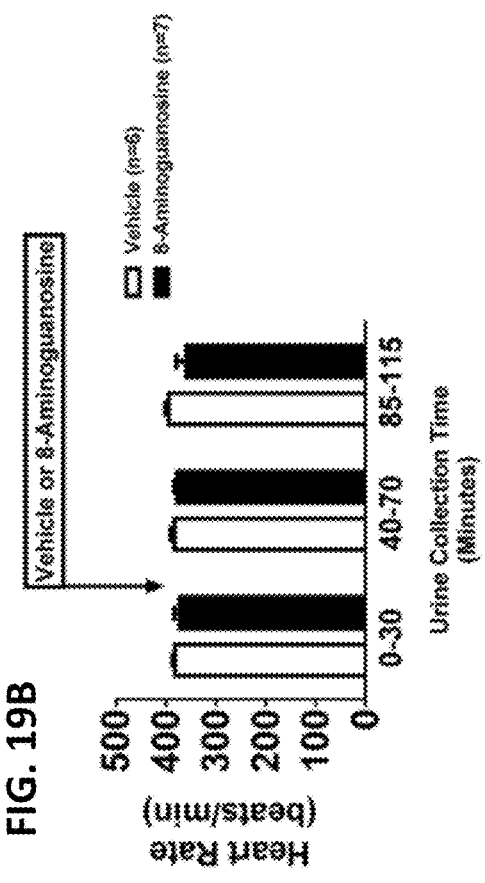
FIGS. 19A-19H: Bar graphs depict (FIG. 19A) mean arterial blood pressure (MABP), (FIG. 19B) heart rate, (FIG. 19C) plasma concentration of aldosterone, (FIG. 19D) glomerular filtration rate (GFR; estimated by creatinine clearance), (FIG. 19E) urine volume, (FIG. 19F) urinary sodium excretion, (FIG. 19G) urinary potassium excretion, and (FIG. 19H) urinary glucose excretion in rats administered either 8-aminoguanosine (33.5 µmoles/kg; 1 ml/kg) or its vehicle (1 ml/kg) intravenously. The p-value given for treatment×period is the interaction term in a repeated measures, 2-factor-ANOVA. $^{a}$: Significantly different from corresponding 0-30 min period. $^{b}$: Significantly different from corresponding vehicle period. Values are means and SEMs.
Figure 19B:
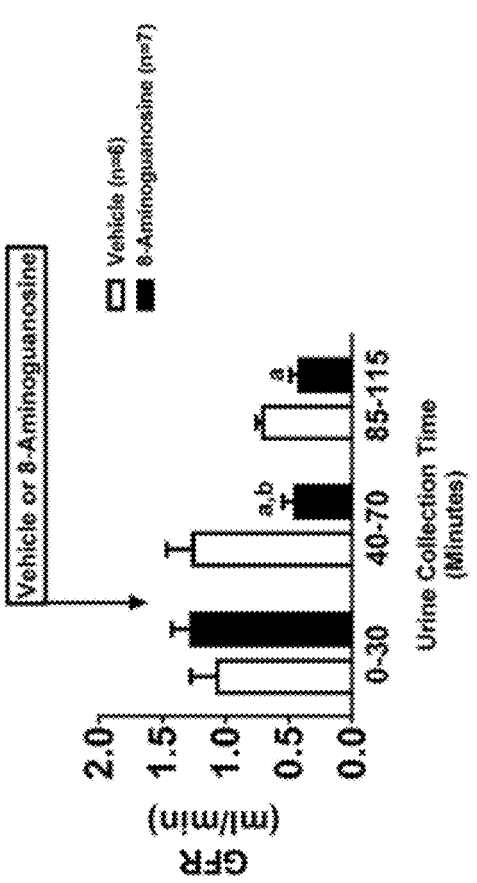
Figure 19C:
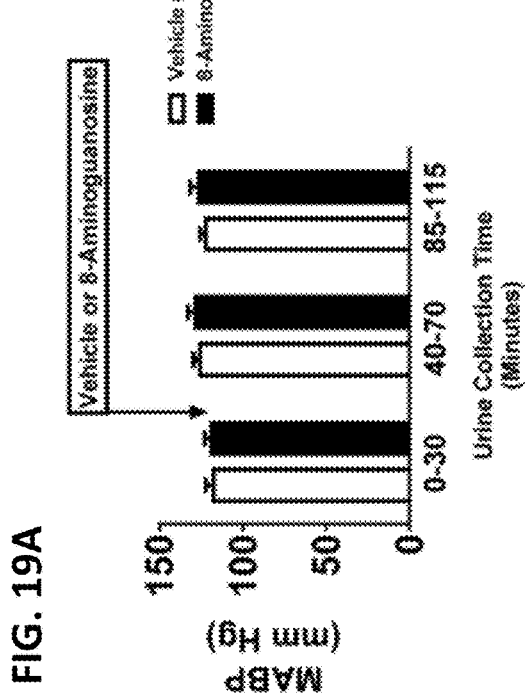
Figure 19D:
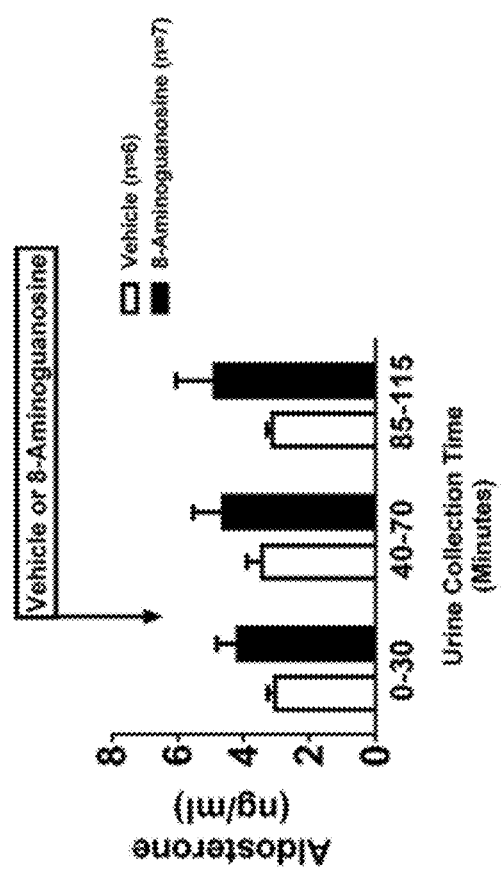
Figure 19E:
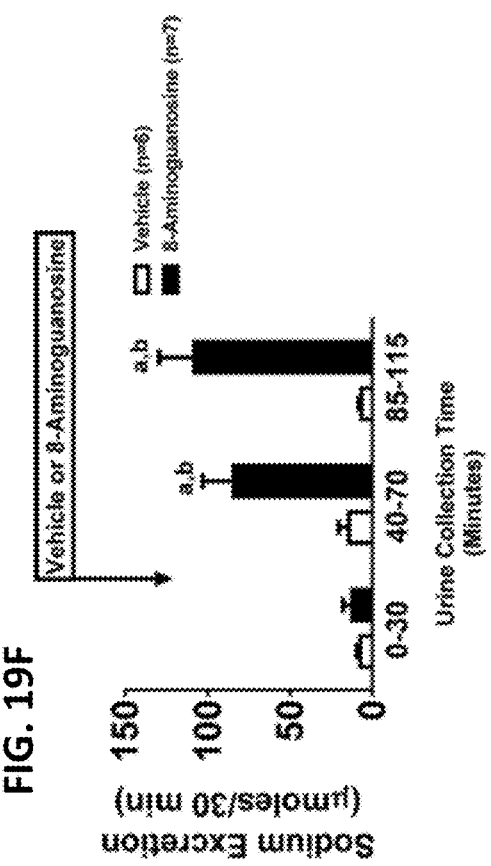
Figure 19F:
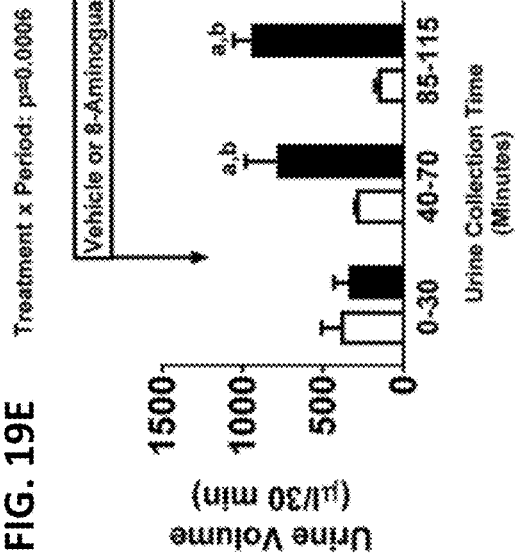
Figure 19G:
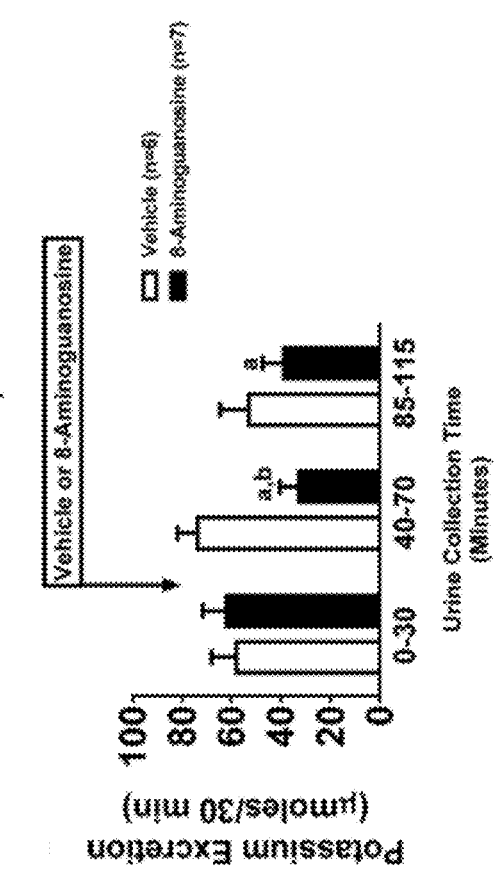
Figure 19H:
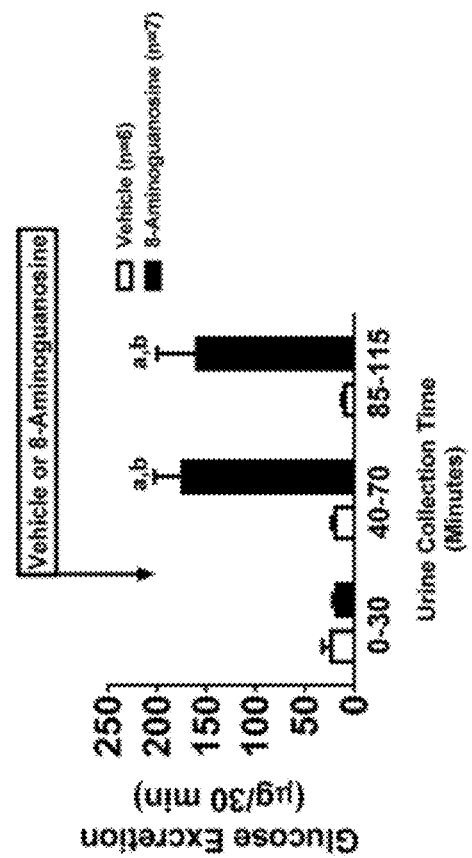
Figure 20B:
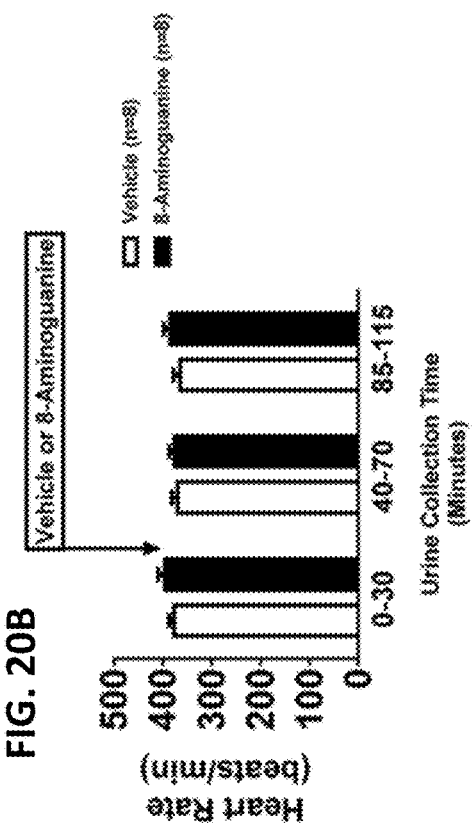
FIGS. 20A-20H: Bar graphs depict (FIG. 20A) mean arterial blood pressure (MABP), (FIG. 20B) heart rate, (FIG. 20C) plasma concentration of aldosterone, (FIG. 20D) glomerular filtration rate (GFR; estimated by creatinine clearance), (FIG. 20E) urine volume, (FIG. 20F) urinary sodium excretion, (FIG. 20G) urinary potassium excretion, and (FIG. 20H) urinary glucose excretion in rats administered either 8-aminoguanine (33.5 µmoles/kg; 1 ml/kg) or its vehicle (1 ml/kg) intravenously. The p-values given for treatment×period is the interaction term in a repeated measures, 2-factor-ANOVA. $^{a}$: Significantly different from corresponding 0-30 min period. $^{b}$: Significantly different from corresponding vehicle period. Values are means and SEMs (n=7-8).
Figure 20D:
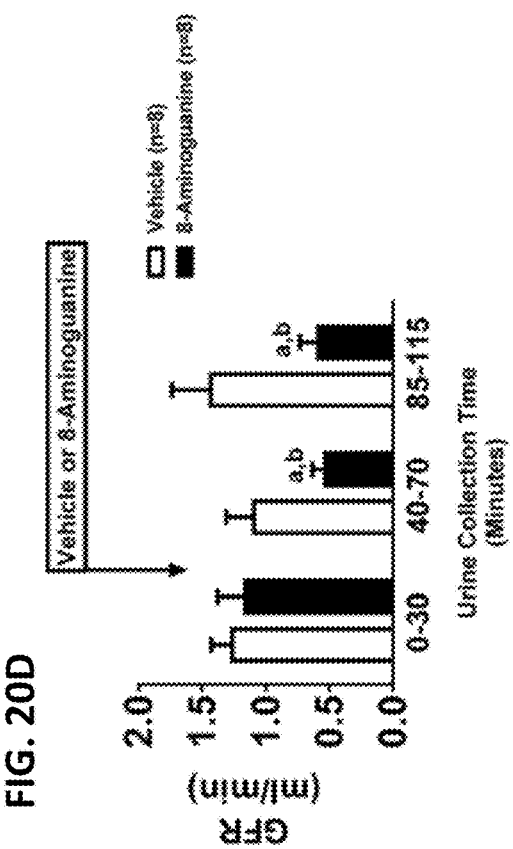
Figure 20A:
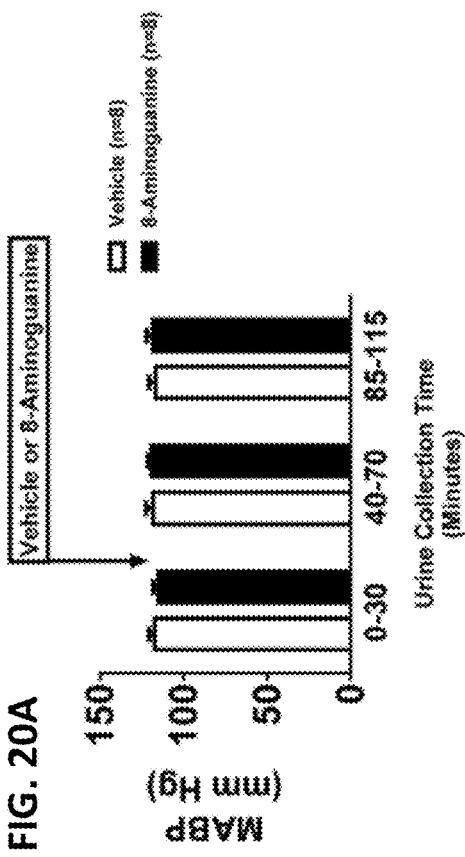
Figure 20C:
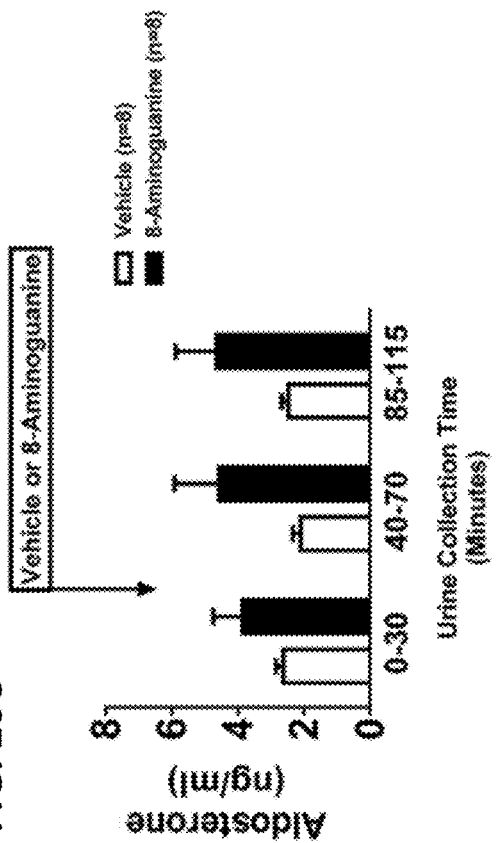
Figure 20F:
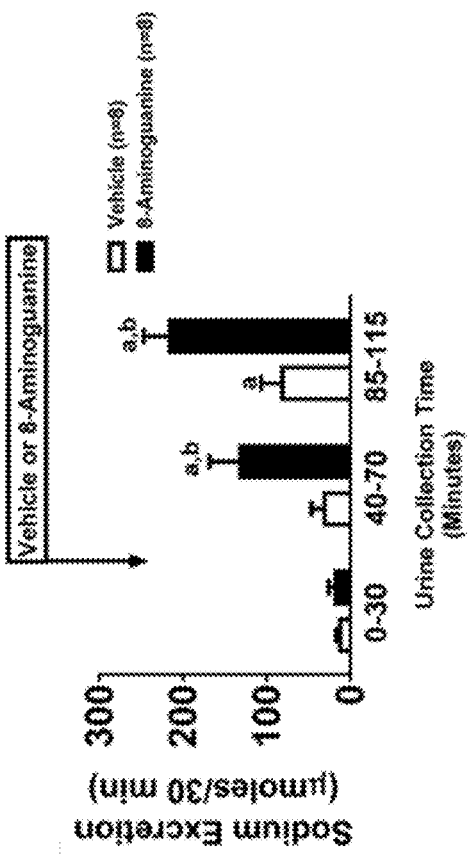
Figure 20H:
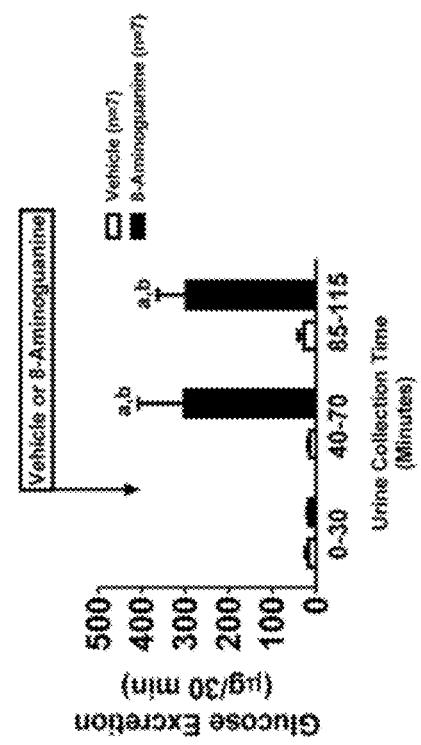
Figure 20E:
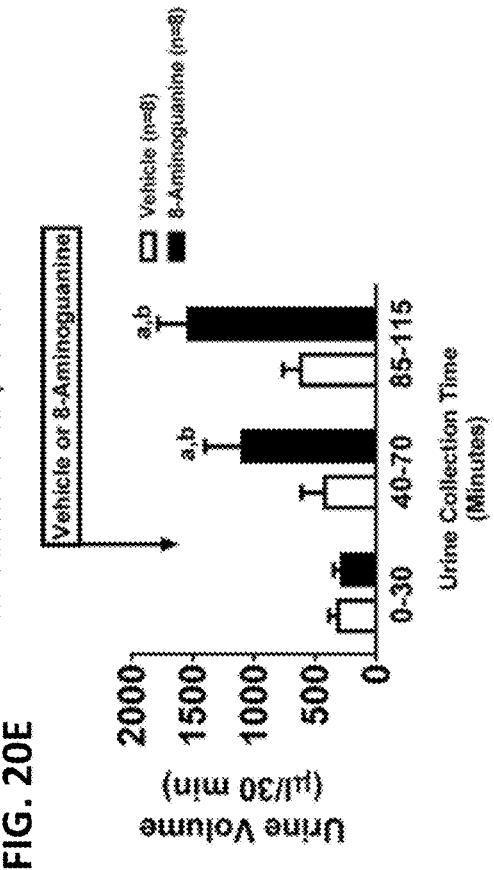
Figure 20G:
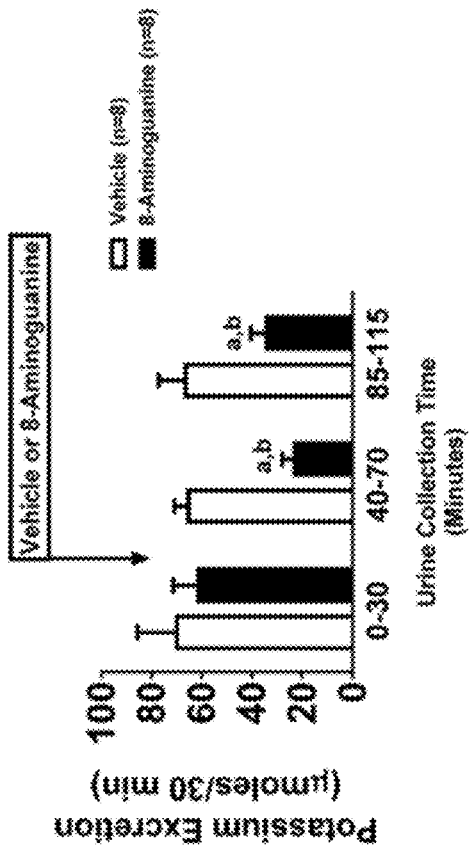

To assay the dosing paradigm, the effects of an intravenous bolus of vehicle (control group), 8-aminoguanosine (33.5 μmoles/kg), and 8-aminoguanine (33.5 μmoles/kg) were examined in anesthetized rats using a head-to-head study (with randomization of treatment groups). As shown in FIGS. 19A-19H and 20A-20H, respectively, neither 8-aminoguanosine nor 8-aminoguanine acutely affected MABP (FIGS. 19A and 20A), HR (FIGS. 19B and 20B), or plasma aldosterone concentrations (FIGS. 19C and 20C). However, both compounds exhibited significantly lower GFR (FIGS. 19D and 20D) and urinary potassium excretion (FIGS. 19G and 20G). Both compounds also exhibited significantly greater urine volume (FIGS. 19E and 20E), urinary sodium excretion (FIGS. 19F and 20F), and urinary glucose excretion (FIGS. 19H and 20H). These effects of intravenously administered 8-aminoguanine and 8-aminoguanosine were qualitatively the same and quantitatively similar.

Example 12

This example describes the effects of administering 8-substituted guanine and 8-substituted guanosine on the concentrations thereof in the renal cortex and medulla as well as in the urine.

Figure 22A:
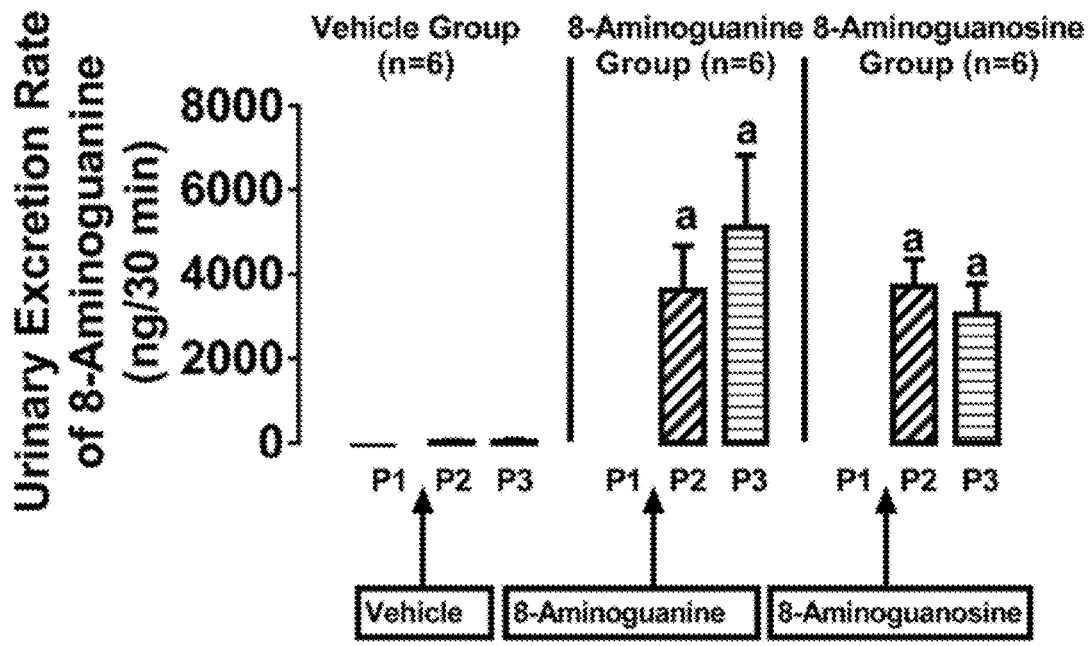
FIGS. 22A-22B: Bar graphs depict the concentrations of 8-aminoguanine (FIG. 22A) and 8-aminoguanosine (FIG. 22B) in the urine before treatments (P1) and after intravenous administration (P2 and P3) of either vehicle (1 ml/kg), 8-aminoguanine (33.5 µmoles/kg; 1 ml/kg) or 8-aminoguanosine (33.5 µmoles/kg; 1 ml/kg). $^{a}$: Significantly different from control (P1). Values are means and SEMs.
Figure 22B:
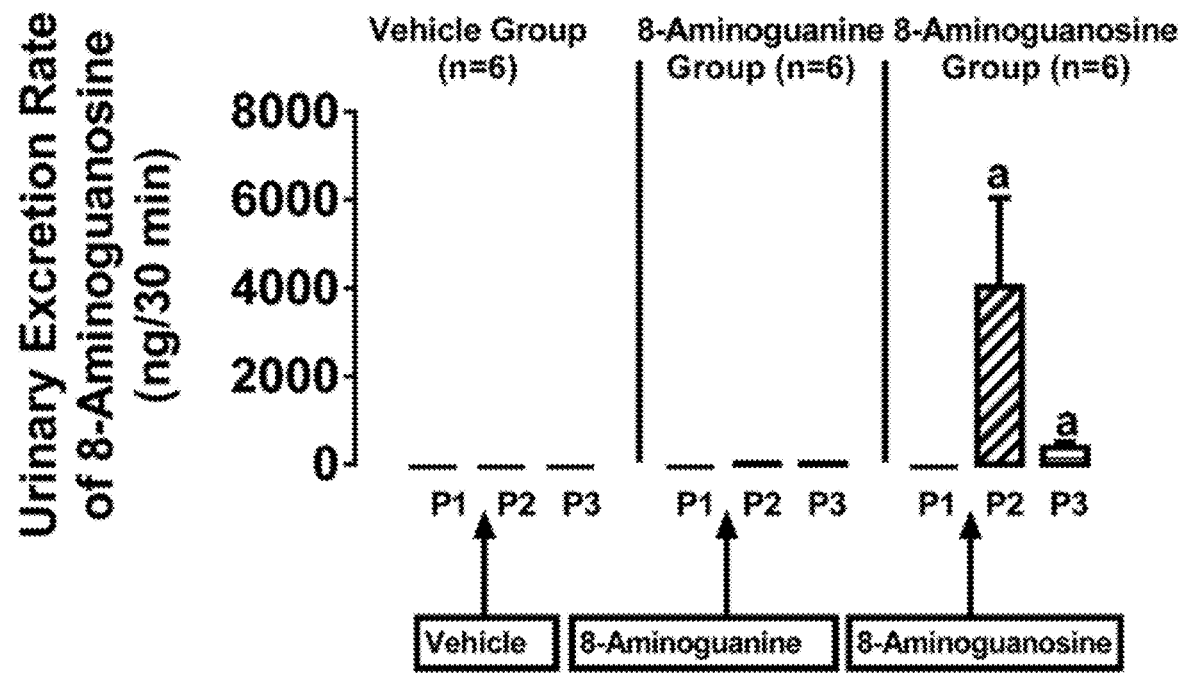

Microdialysis probes were inserted into the renal cortex and medulla of anesthetized rats; the rats stabilized for 2 hours and were then administered an intravenous bolus of vehicle (control group), 8-aminoguanosine (33.5 μmoles/kg), or 8-aminoguanine (33.5 μmoles/kg). The levels of these compounds were then measured in the renal cortex and medulla as well as in the urine using LC-MS/MS. As shown in FIGS. 21A-21D, administration of 8-aminoguanine and 8-aminoguanosine produced immediate, sustained, similar, and large increases in the interstitial levels of 8-aminoguanine in the renal cortex (FIG. 21A) and renal medulla (FIG. 21B). The vehicle alone had no effect. In contrast, neither 8-aminoguanine nor 8-aminoguanosine affected cortical (FIG. 21C) or medullary (FIG. 21D) interstitial levels of 8-aminoguanosine. In the urine (FIGS. 22A-22B), administration of 8-aminoguanine and 8-aminoguanosine also produced immediate, sustained, similar, and large increases in 8-aminoguanine (FIG. 22A). 8-Aminoguanine did not affect urinary levels of 8-aminoguanosine (FIG. 22B). 8-Aminoguanosine did produce an increase in urinary 8-aminoguanosine levels, but this response was variable and short-lived (FIG. 22B).

Example 13

This example describes the effects of administering 8-substituted guanine and 8-substituted guanosine on the ipsilateral and contralateral kidneys.

Increasing doses (0, 0.1, 0.3, and 1.0 μmoles/kg/min) of 8-aminoguanosine and 8-aminoguanine were infused into the left renal artery of anesthetized rats, while MABP and RBF were monitored. The urine volume and urinary excretion of sodium, potassium, and glucose were also measured from both the infused (treated; ipsilateral) and non-infused (within animal control; contralateral) kidneys. A control group was also included with the vehicle alone infused into the left kidney.

Figure 23A:
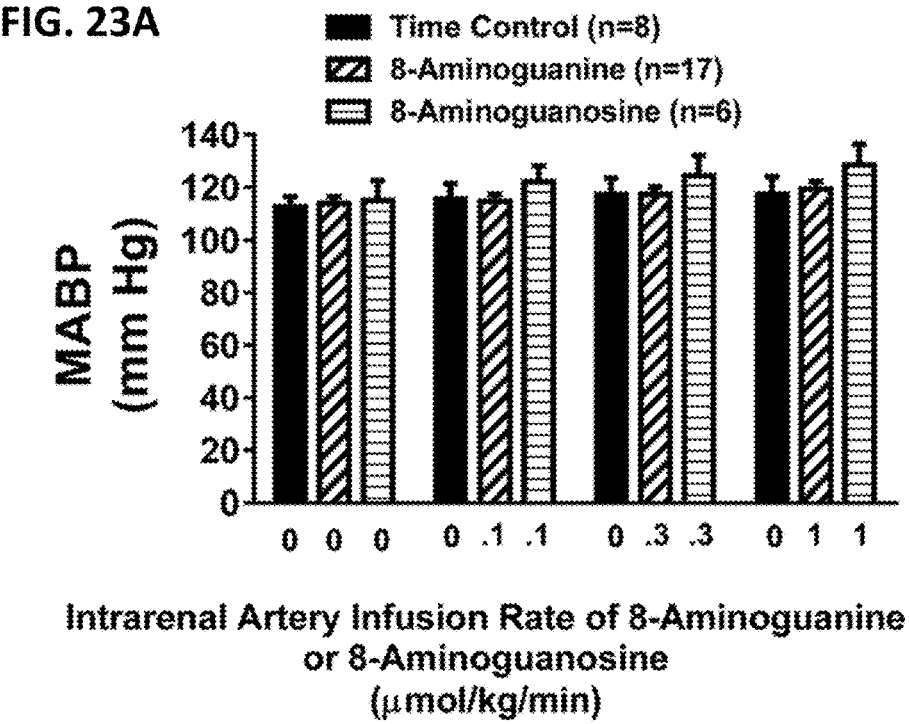
FIGS. 23A-23B: Bar graphs depict the (FIG. 23A) mean arterial blood pressure and (FIG. 23B) renal blood flow in rats receiving intrarenal artery infusions (left kidney) of either vehicle, 8-aminoguanine (0.1, 0.3, and 1 μmoles/kg/min), or 8-aminoguanosine (0.1, 0.3, and 1 μmoles/kg/min). Values are means and SEMs.
Figure 23B:
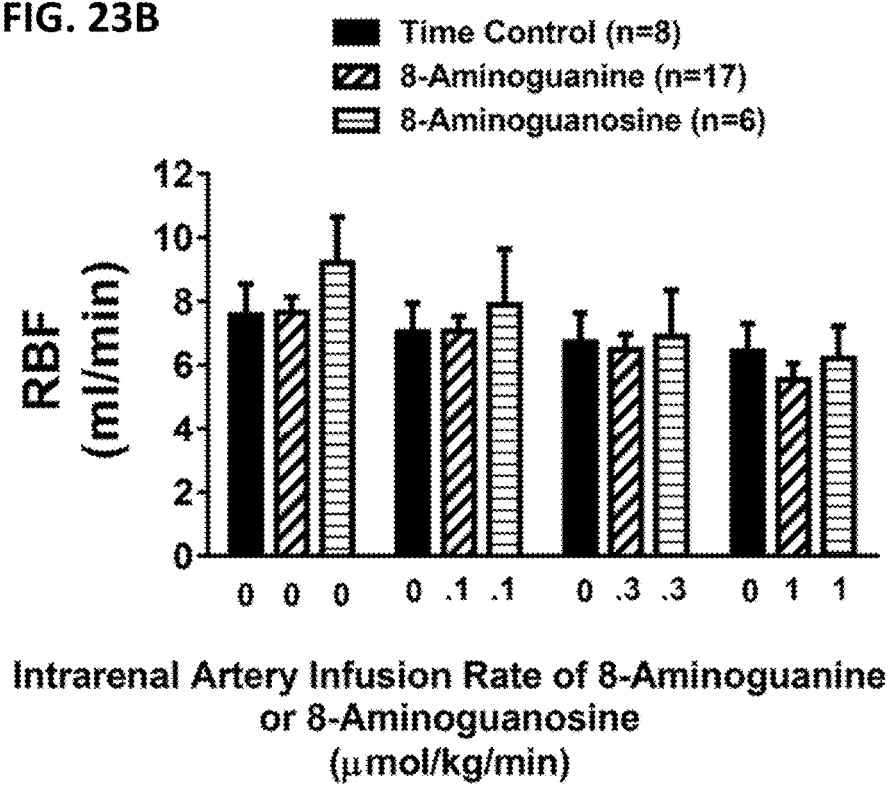

As illustrated in FIGS. 23A-23B, intrarenal artery infusions of vehicle, 8-aminoguanine, and 8-aminoguanosine did not affect MABP (FIG. 23A) or RBF (FIG. 23B). In the control group that received intrarenal artery infusions of the vehicle (FIGS. 24A-24D), no significant differences were observed between the ipsilateral versus the contralateral kidneys during the same period for either urine volume (FIG. 24A) or urinary excretion of sodium (FIG. 24B), potassium (FIG. 24C), or glucose (FIG. 24D).

As with the control group, the group that received an intrarenal artery infusion of 8-aminoguanosine (FIGS. 25A-25D) exhibited no significant differences between the ipsilateral versus the contralateral kidneys during the same time period for either urine volume (FIG. 25A) or urinary excretion of sodium (FIG. 25B) or glucose (FIG. 25D). However, for infusions of 8-aminoguanosine at 0.1, 0.3, and 1 μmoles/kg/min, urinary excretion of potassium by the ipsilateral kidney was significantly lower compared with the contralateral kidney for the corresponding time period (FIG. 25C).

Figure 26A:
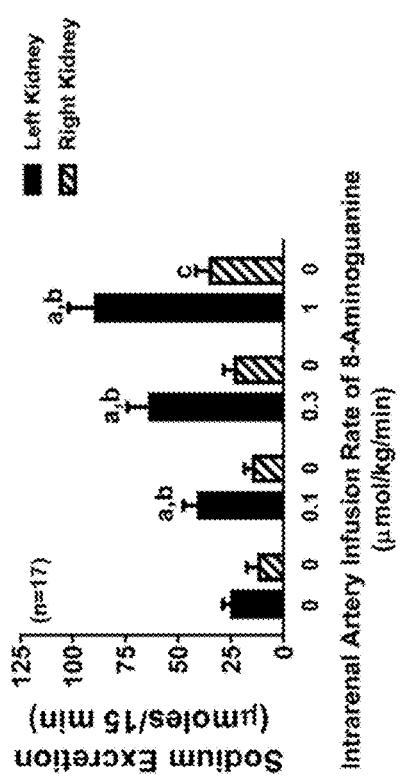
FIGS. 26A-26D: Bar graphs depict the (FIG. 26A) urine excretion, (FIG. 26B) urinary sodium excretion, (FIG. 26C) urinary potassium excretion, or (FIG. 26D) urinary glucose excretion from the left and right kidneys during direct infusions into the left renal artery of increasing doses of 8-aminoguanine (0.1, 0.3, and 1 μmoles/kg/min) during four 15-minute periods. The p-values given for treatment×period is the interaction term in a repeated measures, 2-factor-ANOVA. $^a$: Significantly different from control (0) period for left kidney. $^b$: Significantly different from corresponding period in right kidney. $^c$: Significantly different from control (0) period for right kidney. Values are means and SEMs.
Figure 26C:
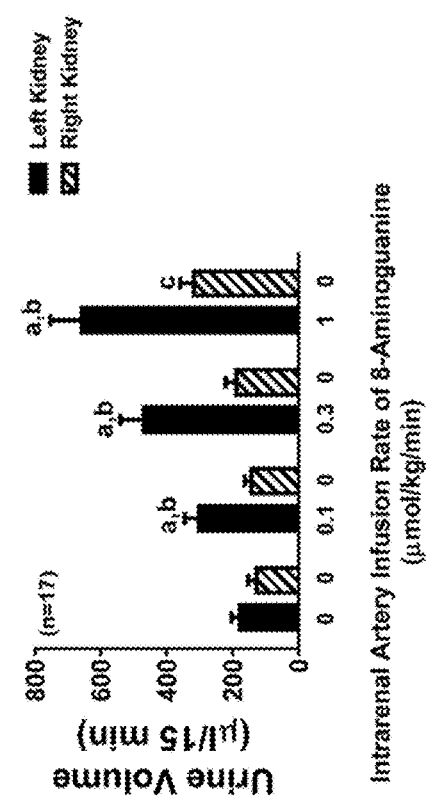
Figure 26B:
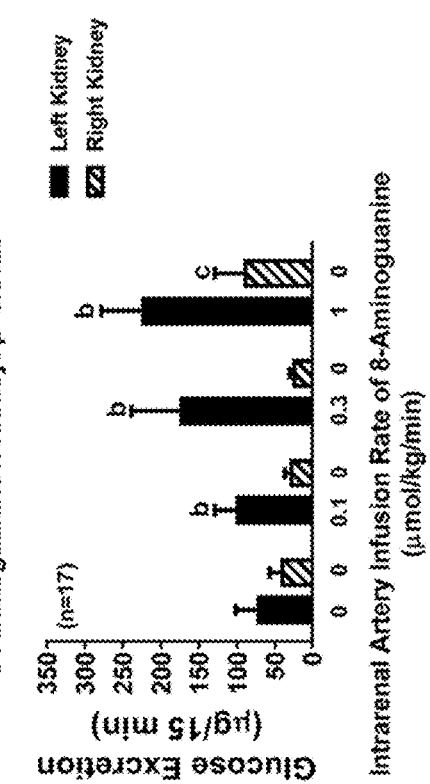
Figure 26D:
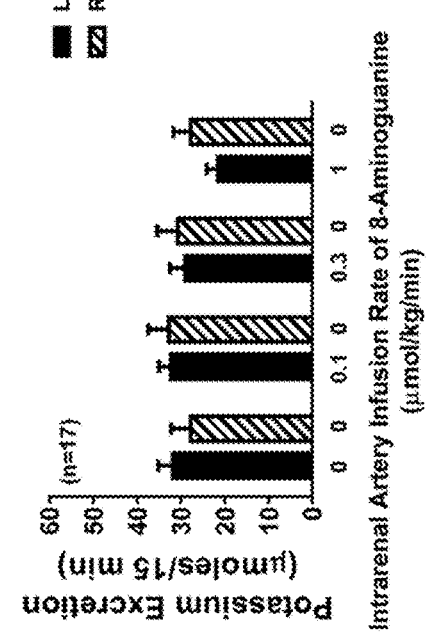

In the group receiving intrarenal administration of 8-aminoguanine (FIGS. 26A-26D) by infusions of 8-aminoguanine at 0.1, 0.3, and 1 μmoles/kg/min, urine (FIG. 26A), sodium (FIG. 26B), and glucose (FIG. 26D) excretion by the ipsilateral kidney were significantly higher compared with the contralateral kidney for the corresponding time period. At 0.1 and 0.3 μmoles/kg/min, 8-aminoguanine had no effect on the excretion of urine, sodium, or glucose by the contralateral kidney; however, compared with the basal level, 8-aminoguanine at 1 μmole/kg/min slightly increased urine, sodium, and glucose excretion by the contralateral kidney.

Further, urinary potassium excretion (FIG. 26C) between the ipsilateral and contralateral kidneys did not differ significantly at any 8-aminoguanine dose.

Example 14

This example discusses the results of Examples 11-13.

Guanosine and guanine derivative modifications at the 8 position of the purine ring are present in vivo. Examples include 8-nitroguanosine (Akaike et al., Proc Natl Acad Sci USA, 100:685-690, 2003), 8-aminoguanosine (Sodum et al., Chem Res Toxicol, 6:269-276, 1993), 8-hydroxyguanosine (Park et al., Proc Natl Acad Sci USA, 89:3375-3379, 1992), 8-nitroguanine (Ohshima et al., Antioxid Redox Signal, 8:1033-1045, 2006), 8-hydroxyguanine (Fraga et al., Proc Natl Acad Sci USA, 87:4533-4537, 1990), and 8-hydroxy-2'-deoxyguanosine (Lam et al., Free Radic Biol Med, 52:2057-2063, 2012).

Exogenous 8-aminoguanosine can be converted into 8-aminoguanine by purine nucleoside phosphorylase (Osborne and Barton, Immunology, 59:63-67, 1986). Thus, whether 8-aminoguanosine is a "pro-drug" or "pro-hormone" was assessed (depending upon whether the source of the 8-aminoguanosine is exogenous or endogenous), where the effects of 8-aminoguanosine on the kidneys are not direct, but are mediated by its metabolism to 8-aminoguanine.

The renal effects of intravenously administered 8-aminoguanosine and 8-aminoguanine were compared head-to-head. Both compounds increased urine volume and the urinary excretion of sodium and glucose, while decreasing the urinary excretion of potassium. Neither intravenous 8-aminoguanosine nor 8-aminoguanine significantly affected plasma aldosterone; thus, diuretic/natriuretic activity is not mediated by inhibiting aldosterone production. However, both intravenous 8-aminoguanosine and 8-aminoguanine decreased GFR. This decrease in GFR suggests 1) that the diuretic/natriuretic/glucosuric effects of 8-aminoguanosine and 8-aminoguanine are not mediated by increasing the filtered load of electrolytes or glucose and 2) that the increased sodium excretion produced by these compounds may activate tubuloglomerular feedback to reduce GFR. This experiment also shows that both compounds behave qualitatively the same and quantitatively similar when administered intravenously, which is consistent with 8-aminoguanosine as an 8-aminoguanine prodrug/prohormone.

Where 8-aminoguanosine is truly a prodrug/prohormone of 8-aminoguanine, systemic administration of pharmacologically active doses of 8-aminoguanosine will produce intrarenal levels of 8-aminoguanine generated by corresponding doses of 8-aminoguanine with similar pharmacological activity. To assess whether 8-aminoguanosine is a prodrug/prohormone of 8-aminoguanine, intrarenal levels of 8-aminoguanosine and 8-aminoguanine were measured by inserting microdialysis probes into the renal cortex and medulla. Next, a dose of 8-aminoguanosine and a corresponding dose of 8-aminoguanine was intravenously injected, which produced qualitatively the same and quantitatively similar renal responses, as confirmed in the first protocol. Intravenous administration of 8-aminoguanosine increased renal interstitial levels of 8-aminoguanine to the same degree as corresponding intravenous doses of 8-aminoguanine.

Moreover, 8-aminoguanosine did not increase renal interstitial levels of 8-aminoguanosine. These data confirm that 8-aminoguanosine is an 8-aminoguanine prodrug (if exogenous) or prohormone (if endogenous). This finding is corroborated by the finding that intravenous 8-aminoguanosine and 8-aminoguanine produce similar increases in urinary levels of 8-aminoguanine. Although intravenous 8-aminoguanosine did increase urinary levels of 8-aminoguanosine, this effect was variable and limited in time.

Low doses of 8-aminoguanosine and 8-aminoguanine were administered directly into the left renal artery while monitoring urine, sodium, potassium, and glucose excretion from both the ipsilateral (treated) and contralateral (control) kidneys. Where 8-aminoguanosine is an 8-aminoguanine prodrug and the conversion of arterial 8-aminoguanosine to 8-aminoguanine occurs largely in the systemic circulation, administration of 8-aminoguanosine into the renal artery will be inactive, but administration of corresponding 8-aminoguanine doses will induce diuresis and natriuresis.

Consistently, intrarenal artery infusions of 8-aminoguanosine did not affect urine volume or the urinary output of sodium or glucose at any of the doses examined. In contrast, administration of 8-aminoguanine into the renal artery markedly increased urine excretion, sodium excretion, and glucose excretion in the infused kidney at all doses examined. However, only the highest dose of 8-aminoguanine affected these parameters in the non-infused kidney, and even then, only slightly. These results are consistent with direct intrarenal actions by 8-aminoguanine causing diuresis, natriuresis, and glucosuria; however, 8-aminoguanosine does not have such a direct effect but requires metabolism to 8-aminoguanine.

8-Aminoguanine decreased potassium excretion when intravenously administered, but not when directly administered into the renal artery. At the doses employed, the increased presentation of sodium to the distal nephron likely offset the tendency for 8-aminoguanine to decrease potassium excretion such that the net effect of intrarenal 8-aminoguanine was "potassium-sparing," but potassium excretion overall did not decrease.

Although intrarenal artery administration of 8-aminoguanosine did not affect urine volume or sodium or glucose excretion, intrarenal artery infusions of 8-aminoguanosine did significantly reduce potassium excretion by the ipsilateral kidney. These data suggest that 8-aminoguanosine directly induces anti-kaliuresis and that this aspect of the 8-aminoguanosine pharmacology does not require conversion to 8-aminoguanine. Unlike 8-aminoguanine, intrarenal artery infusions of 8-aminoguanosine did not increase sodium excretion and, thus, the anti-kaliuretic effects of 8-aminoguanosine were observable (i.e., were not masked by increased sodium delivery to the distal nephron). Taken together, these findings show two distinct mechanisms of action for 8-aminoguanine and 8-aminoguanosine. One mechanism causes diuresis, natriuresis, and glucosuria and is directly mediated by 8-aminoguanine as well as indirectly mediated by 8-aminoguanosine; a separate mechanism causes anti-kaliuresis and is directly mediated by both 8-aminoguanine and 8-aminoguanosine.

Both 8-aminoguanosine and 8-aminoguanine inhibit PNPase. However, 8-aminoguanine is at least a 10-fold more potent PNPase inhibitor than 8-aminoguanosine (Kazmers et al., Science, 214:1137-1139, 1981; Gilbertsen and Dong, Ann NY Acad Sci, 451:313-314, 1985). Therefore, 8-aminoguanosine as an 8-aminoguanine prodrug is consistent with the diuretic/natriuretic/glucosuric activity of these compounds being related to 8-aminoguanine-induced inhibition of renal PNPase.

The results demonstrate that the diuretic, natriuretic, and glucosuric activity of 8-aminoguanosine is due to its conversion to 8-aminoguanine. As intrarenal artery administration of 8-aminoguanosine does not induce diuresis/natriuresis/glucosuria but intravenous administration does, our results show that arterial 8-aminoguanosine is processed to 8-aminoguanine primarily throughout the systemic circulation. These data do not preclude endogenous 8-aminoguanosine production within some non-vascular compartments within the kidney that may be locally metabolized to 8-aminoguanine in the kidney and, thus, exert effects on nephron function.

Thus, the diuretic, natriuretic, glucosuric, and anti-kaliuretic effects of systemically administered 8-aminoguanosine and 8-aminoguanine were confirmed. The renal effects of these compounds were not due to inhibition of aldosterone release. In addition, with respect to inducing diuresis, natriuresis, and glucosuria, 8-aminoguanosine is an 8-aminoguanine prodrug. Furthermore, the mechanism by which 8-aminoguanosine and 8-aminoguanine cause anti-kaliuresis is distinct from the mechanism by which the compounds induce diuresis, natriuresis, and glucosuria.

Example 15

This example describes increased purine nucleoside phosphorylase (PNPase) activity in patients with sickle cell disease (SCD).

Figure 27A:
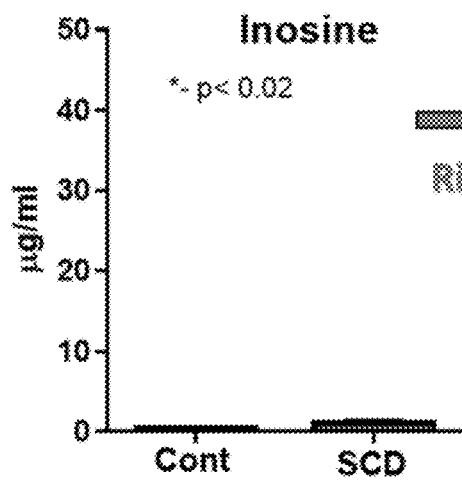
FIGS. 27A-27D: Increased purine nucleoside phosphorylase (PNPase) activity in adult patient with SCD. Control subjects and sickle cell disease (SCD) patients exhibited differences in urinary levels of inosine (FIG. 27A), hypoxanthine (FIG. 27B), guanosine (FIG. 27C), and guanine (FIG. 27D).
Figure 27B:
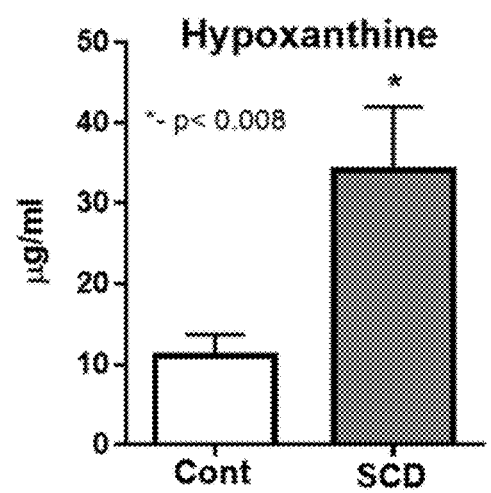
Figure 27C:
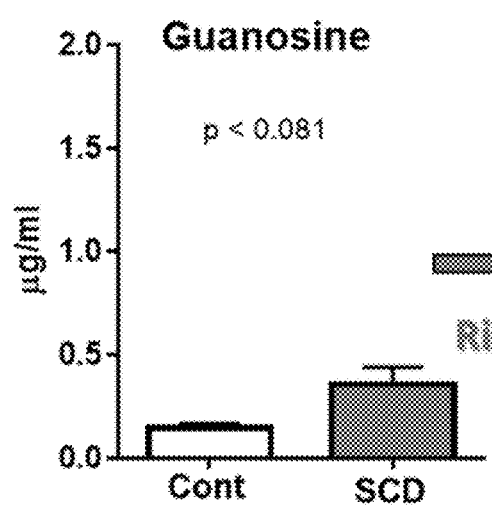
Figure 27D:
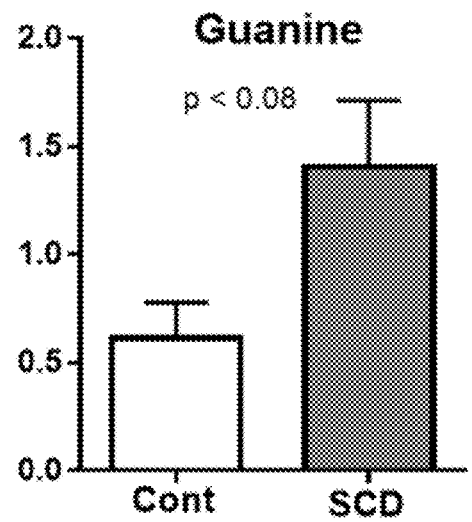

Sickle cell disease patients often suffer from pulmonary hypertension (PH). Urine samples from 11 adult asymptomatic SCD patients (8 male and 3 female; 25.6±1.8 y/o; Hb=9.96±0.64; Htc=29.7±0.6%; reticulocytes=8.2±1.4%; LDH=295±15 U/L) and 5 healthy controls at corresponding ages were obtained, and urinary purines levels were measured using ultra-performance-tandem mass spectrometry (UPLC-MS/MS) in the selected ion monitoring mode as previously described (Ren et al., J Pharmacol Exp Ther., 325:920-926, 2008). In adult SCD patients, significant increases in urine levels of hypoxanthine and guanine were observed, indicating increased release/activity of extracellular PNPase (FIGS. 27A-27B), which is an enzyme that metabolizes inosine to hypoxanthine and guanosine to guanine. Moreover, reduced levels of two potent endogenous PNPase inhibitors, 8-aminoguanosine and 8-aminoguanine, were observed in adult SCD patients (FIGS. 28A-28B). These data show that extracellular PNPase is overly active in SCD patients, partially due to reduced levels of the endogenous PNPase inhibitors 8-aminoguanosine and 8-aminoguanine. Thus, the increased activity of extracellular PNPase likely contributes to the pathophysiology of PH in SCD patients.

Example 16

This example describes increased PNPase activity in a primate model of HIV-related pulmonary hypertension (PH).

Where increased activity of extracellular PNPase contributes to the pathophysiology of PH in SCD patients, increased PNPase activity will occur in other disease states associated with PH. As with SCD, PH is a serious complication that often occurs in patients infected with the immunodeficiency virus (HIV) (Seoane et al., Southern Medical Journal, 94:635-639, 2001; Chi et al., Endothelium: Journal of Endothelial Cell Research, 7:223-242, 2000). Accordingly, the role of PNPase in a nonhuman-primate model of HIV infection (using simian immunodeficiency virus, SIV) that develops pulmonary vascular lesions and PH was examined (George et al., AIDS Research and Human Retroviruses, 27:103-111, 2011; George et al., American Journal Of Respiratory Cell And Molecular Biology, 48:374-381, 2013). The metabolic profile of urinary purines was examined as in Example 15, but SIV-infected macaques were used. Dramatically increased metabolism of purine nucleosides in SIV primates was detected (FIGS. 29A-29F), which was associated with increased production of inosine, hypoxanthine, and guanine. These data show that, similar to SCD patients (see above), primates with SIV and PH exhibit significantly increased PNPase release/activity. Taken together, these data show that PNPase underlies the pathophysiology of PH both in SCD and PH.

Example 17

This example describes inhibition of hypoxia-induced sickling by the PNPase inhibitor 8-aminoguanosine and inosine in red blood cells (RBCs) from SCD patients.

In addition to causing PH in SCD patients and HIV-infected patients, the contribution of PNPase to RBC sickling in SCD patients was assessed. Fresh RBCs were obtained from two adult SCD patients (HbSS); the RBCs were diluted in F-10 HAM buffer to a final hematocrit of 4%. Next, glucose was added for a final concentration of 5.5 mmol/L, and the samples were incubated at room air/ temperature in 12-well plates. The RBCs were then treated with either vehicle, 8-aminoguanosine (2 µmol/L), inosine (2 µmol/L), or an 8-aminoguanosine and inosine combination. After 1.5 hours, the RBCs were placed in a hypoxic glove box and maintained under hypoxia (5% O2) for 3 hours, while undergoing mild agitation. At the end of incubation, to prevent reoxygenation-derived morphological changes, the RBCs were fixed under hypoxic conditions in the hypoxic glove box. The samples were assayed for percent sickling.

Figure 30:
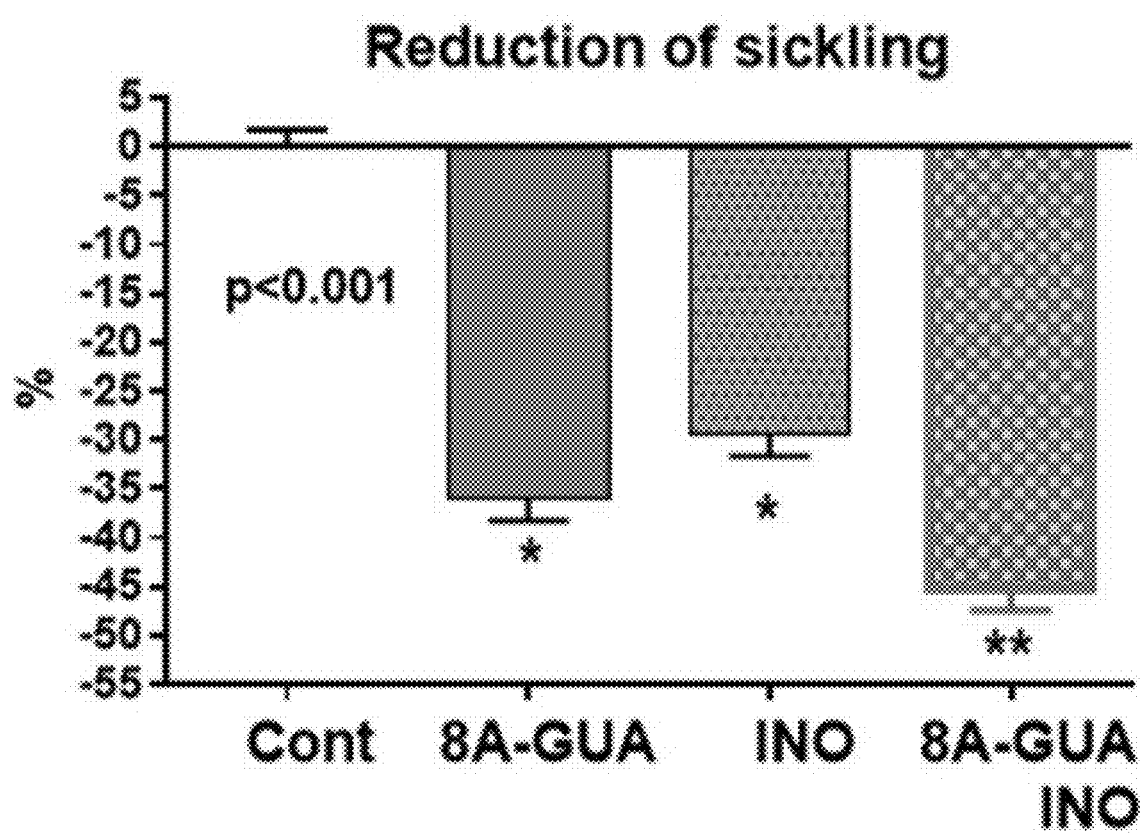
FIG. 30: Effects of the PNPase inhibitor 8-aminoguanosine (8A-GUA) and PNPase substrate inosine (INO) alone and combined (8A-GUA INO) on hypoxia-induced sickling in RBCs from SCD patients.
Figure 35H:
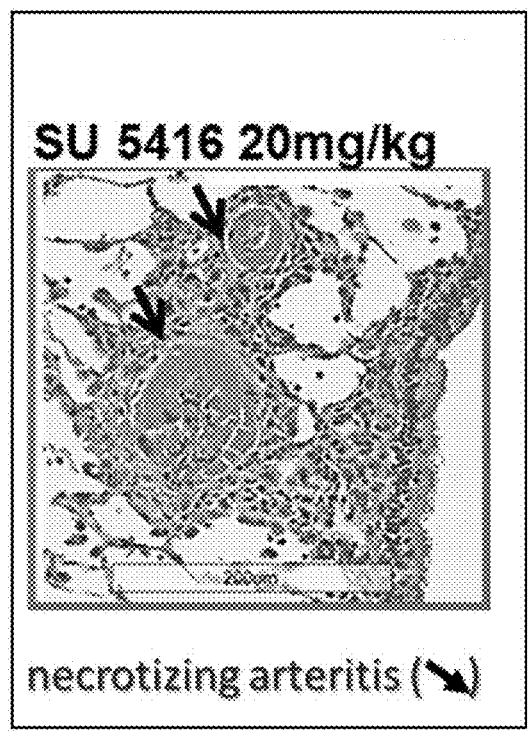

Both 8-aminoguanosine and inosine significantly reduced hypoxia-induced sickling of RBCs from patients with SCD. Notably, 8-aminoguanosine potentiated the inhibitory effects of inosine on hypoxia-induced sickling (FIG. 30). These data show that PNPase inhibitors, such as 8-substituted guanines and guanosines, not only protect against SCD and protect HIV patients from PH (Examples 15 and 16) but also provide protection against sickling events in SCD patients.

Example 18

This example describes guanosine attenuation of monocrotaline (MCT)-induced PH.

Because PNPase metabolizes guanosine to guanine, the mechanism by which PNPase activity is associated with PH likely includes guanosine protection against PH. A total of 24 male Sprague Dawley rats were used to determine whether administration of guanosine attenuates the development of PH in animals with MCT-induced PH. Animals were randomly assigned for intraperitoneal (i.p.) injection with either a mixture of 1 ml of 1N HCl neutralized with 1.0 N NaOH and diluted with distilled water (10 ml/kg, Control group; n=8) or MCT (60 mg/kg, n=18). The MCT (Sigma, St Louis, Mo.) was dissolved in 1N HCl at 100 mg/ml, which was neutralized with 1 N NaOH and diluted with distilled water to 6 mg/ml. Next, a subset of MCT rats (n=8) were assigned to receive guanosine (30 mg/kg/day). The rats were randomly assigned to the Control, MCT, or MCT+guanosine group.

In this PH model, three weeks after MCT administration, mortality rapidly increases (Ren et al., J Pharmacol Exp Ther., 325:920-926, 2008; Seoane et al., Southern Medical Journal, 94:635-639, 2001). Therefore, animals were monitored for four weeks, and acute measurements of right ventricular pressure and morphometric analyses were performed. Twenty-eight days after administration of MCT, the animals were anesthetized and instrumented for right ventricular peak systolic pressure (RVPSP) measurement. Briefly, a PE-240 polyethylene catheter was inserted into the trachea to facilitate breathing. An angled Milliar Micro-tip pressure transducer catheter SPR-513 (Millar Instruments) was inserted into the right jugular vein and advanced into the right ventricle (RV) for RVPSP measurement. After 30-minutes of stabilization, RVPSP was recorded over 20 minutes. The animals were euthanized by anesthetic overdose, and the heart and lungs were collected for morphometric analyses.

As shown in FIG. 31A, compared with the control group, MCT animals exhibited increased RVPSP. Further, MCT-treated animals exhibited significant RV dysfunction as indicated by increased RV end diastolic pressure (RV EDP), reduced RV contractility index, and increased RV mass (FIGS. 31B-31E). MCT also induced remodeling (thickening) of the pulmonary vasculature (FIGS. 32A-32F) and induced lung inflammation (i.e., infiltration of the lungs by inflammatory ED1+ cells; FIGS. 32G-32I).

Treatment with guanosine attenuated PH, prevented RV dysfunction, and attenuated RV hypertrophy (FIGS. 31A-31E). Guanosine also attenuated pulmonary vascular remodeling and reduced inflammatory cell infiltration into the lungs (FIGS. 32A-32I).

Example 19

The example describes PNPase inhibitor 8-aminoguanosine attenuation of Sugen 5416+hypoxia-induced angioproliferative PH.

Examples 15-18 show that guanosine (a substrate for PNPase) attenuates PH. Therefore, direct inhibition of PNPase should also attenuate PH. A total of 36 female Sprague Dawley rats were used to determine whether administration of the PNPase inhibitor 8-aminoguanosine attenuates development of angioproliferative PH in animals with Sugene5416+hypoxia-induced PH. The animals were randomly assigned to receive subcutaneous injection of vehicle [(control group; n=8; 0.5% (w/v) carboxymethylcellulose sodium, 0.9% (w/v) sodium chloride, 0.4% (v/v) polysorbate 80, and 0.9% (v/v) benzyl alcohol in deionized water] or subcutaneous injection of SU5416 20 mg/kg (n=16; SU+Hx group). A subset of the SU5416-treated animals received 8-aminoguanosine (30 mg/kg/day in drinking water (n=12; 8-amino-guanosine group). On day 0, all SU5416-treated animals (SU+Hx and 8-aminoguanosine groups) were exposed to chronic hypoxia for 3 weeks. The animals were placed into normobaric plexiglas chambers (BioSpherix, Redfield, N.J., USA). The chambers were continuously flushed with nitrogen to maintain 10% oxygen and low $CO_2$ concentrations (<0.5%) with the $O_2$ and $CO_2$ concentrations continuously monitored (PROOX110, BioSpherix oxygen controller and LB-2 $CO_2$ analyzer, Sensormedics). At day 21, the animals were returned to a normoxic environment. Three weeks later (day 42), the animals were anesthetized and instrumented for RVPSP measurements. A PE-240 polyethylene catheter was inserted into the trachea to facilitate breathing, and the SPR-513 catheter (Millar Instruments) was inserted into right jugular vein and advanced into RV for RVPSP measurements. After 20-30-minutes of stabilization, RVPSP was recorded over 20 minutes. The animals were euthanized by anesthetic overdose, and the heart and lungs were collected for morphometric analyses.

SU+Hx caused PH, as demonstrated by the increases in RVPSP, RV EDP, and the Fulton index and as further demonstrated by the decreases in RV contractility (FIGS. 33A-33D). Moreover, histopathological analysis revealed numerous occlusive and plexiform lesions in SU+Hx-induced PH (FIGS. 34A-34C); further, some female SU-Hx rats even developed grade 6 necrotizing arteritis (FIG. 34D). In the SU+Hx-treated animals, 8-aminoguanosine significantly reduced RVPSP, decreased RV EDP, improved RV contractility, and decreased the Fulton index (FIGS. 33A-33D). Moreover, in the SU+Hx-treated animals, 8-aminoguanosine reduced the number of occlusive vascular lesions and plexiform vascular lesions as well as prevented sporadic occurrence of grade 6 necrotizing arteritis lesions (FIGS. 35A-35G).

It will be apparent that the precise details of the methods or compositions described may be varied or modified without departing from the spirit of the described invention. We claim all such modifications and variations that fall within the scope and spirit of the claims below.

We claim:

1. A method of treating a subject with sickle cell disease, comprising:
administering to the subject a therapeutically effective amount of a purine nucleoside phosphorylase (PNPase) inhibitor, wherein the PNPase inhibitor is a guanine comprising a substituent at the 8-position and/or a guanosine comprising a substituent at the 8-position, wherein;
the substituent is amine, hydroxyl, nitro, nitroso, alkoxy, carbonyl, halogen, carboxyl, ester, carbonate, amide, or haloaliphatic,
thereby treating the sickle cell disease in the subject.

2. The method of claim 1, wherein the substituent is amine, hydroxyl, or nitro.

3. The method of claim 1, wherein the guanine comprising a substituent at the 8-position is 8-aminoguanine and/or the guanosine comprising a substituent at the 8-position is 8-aminoguanosine.

4. The methods of claim 1, further comprising administering PNPase substrate to the subject.

5. The method of claim 1, wherein the subject has increased sickling of red blood cells, and administering the composition decreases the sickling of red blood cells.

6. The method of claim 1, wherein the subject is exposed to hypoxic and/or hypoxemic conditions.

7. The method of claim 6, wherein the subject lives or works at high elevations.

8. The method of claim 1, further comprising administering an additional therapy to treat the subject.

9. The method of claim 8, wherein the additional therapy is at least one of hydroxyurea therapy, penicillin prophylaxis therapy, bone marrow transplantation, stem cell transplantation, immunization, pain medication, blood transfusion, anti-inflammatory therapy, anti-adhesive therapy, anti-sickling therapy, altered hemoglobin expression therapy, anticoagulant and anti-platelet therapy, and/or nitric oxide (NO) therapy.

10. The method of claim 1, wherein the therapeutically effective amount of the purine nucleoside phosphorylase (PNPase) inhibitor is administered orally to the subject.

11. A method of reducing sickling of red blood cells in a subject comprising:

selecting a subject with sickle cell disease; and administering to the subject a therapeutically effective amount of a purine nucleoside phosphorylase (PNPase) inhibitor and/or a PNPase purine nucleoside substrate, wherein the PNPase inhibitor is a guanine comprising a substituent at the 8-position and/or a guanosine comprising a substituent at the 8-position, wherein the substituent is amine, hydroxyl, nitro, nitroso, alkoxy, carbonyl, halogen, carboxyl, ester, carbonate, amide, or haloaliphatic; and thereby reducing sickling of red blood cells in the subject.

12. The method of claim 11, wherein the substituent is amine, hydroxyl, or nitro.

13. The method of claim 11, wherein the guanine comprising a substituent at the 8-position is 8-aminoguanine and/or the guanosine comprising a substituent at the 8-position is 8-aminoguanosine.

14. The method of claim 11, further comprising administering a PNPase substrate to the subject.

15. The method of claim 11, wherein the subject is exposed to hypoxic and/or hypoxemic conditions.

16. The method of claim 15, wherein the subject lives or works at high elevations.

17. The method of claim 11, further comprising administering an additional therapy to treat the subject.

18. The method of claim 17, wherein the additional therapy is at least one of hydroxyurea therapy, penicillin prophylaxis therapy, bone marrow transplantation, stem cell transplantation, immunization, pain medication, blood transfusion, anti-inflammatory therapy, anti-adhesive therapy, anti-sickling therapy, altered hemoglobin expression therapy, anti-coagulant and anti-platelet therapy, and/or nitric oxide (NO) therapy.

19. The method of claim 11, wherein the therapeutically effective amount of the purine nucleoside phosphorylase (PNPase) inhibitor is administered orally to the subject.

20. The method of claim 1, further comprising measuring inosine, hypoxanthine, guanosine, or guanine in a urine sample from the subject.

21. The method of claim 11, further comprising measuring inosine, hypoxanthine, guanosine, or guanine in a urine sample from the subject.

22. The method of claim 1, further comprising measuring 8-aminoguanosine or 8-aminoguanine in a urine sample from the subject.

23. The method of claim 11, further comprising measuring 8-aminoguanosine or 8-aminoguanine in a urine sample from the subject.

* * * * *